United States Patent
Di Ruscio et al.

(10) Patent No.: US 10,941,399 B2
(45) Date of Patent: Mar. 9, 2021

(54) METHODS AND COMPOSITIONS FOR GENE-SPECIFIC DEMETHYLATION BY DNA METHYLTRANSFERASE (DNMT)-RNA INTERACTION

(75) Inventors: Annalisa Di Ruscio, Brookline, MA (US); Alexander K. Ebralidze, Brookline, MA (US); Daniel G. Tenen, Jamaica Plain, MA (US); Giuseppe Leone, Rome (IT)

(73) Assignees: Beth Israel Deaconess Medical Center, Inc., Boston, MA (US); Università Cattolica del Sacro Cuore, Milan (IT)

( * ) Notice: Subject to any disclaimer, the term of this patent is extended or adjusted under 35 U.S.C. 154(b) by 0 days.

(21) Appl. No.: 14/111,971

(22) PCT Filed: Apr. 13, 2012

(86) PCT No.: PCT/US2012/033617
§ 371 (c)(1),
(2), (4) Date: Mar. 6, 2014

(87) PCT Pub. No.: WO2012/142480
PCT Pub. Date: Oct. 18, 2012

(65) Prior Publication Data
US 2014/0171492 A1    Jun. 19, 2014

Related U.S. Application Data

(60) Provisional application No. 61/475,566, filed on Apr. 14, 2011.

(51) Int. Cl.
*C12N 15/11*     (2006.01)
*C12N 15/113*    (2010.01)
*C12N 15/63*     (2006.01)

(52) U.S. Cl.
CPC ........ *C12N 15/113* (2013.01); *C12N 15/1137* (2013.01); *C12N 15/635* (2013.01); *C12N 2310/113* (2013.01); *C12N 2310/13* (2013.01); *C12N 2310/333* (2013.01); *C12N 2310/334* (2013.01); *C12N 2320/31* (2013.01); *C12Y 201/01037* (2013.01)

(58) Field of Classification Search
CPC .............. C12N 15/113; C12N 2310/11; C12N 9/1007; C12N 15/11; C12N 15/111; C12N 2310/334; C12N 2330/30; C12N 2500/40; C12N 15/8218
See application file for complete search history.

(56) References Cited

U.S. PATENT DOCUMENTS

| | | | |
|---|---|---|---|
| 6,214,806 B1* | 4/2001 | Krieg et al. | 514/44 A |
| 6,306,655 B1* | 10/2001 | Monia et al. | 435/375 |
| 6,525,191 B1* | 2/2003 | Ramasamy | C07H 19/056 435/6.1 |
| 7,691,997 B2* | 4/2010 | Khvorova | A61K 31/713 536/24.5 |
| 7,759,478 B1* | 7/2010 | Bentwich | 536/24.5 |
| 2003/0212026 A1* | 11/2003 | Krieg | A61K 31/7088 514/44 R |
| 2005/0191653 A1* | 9/2005 | Freier | C07H 21/04 435/6.11 |
| 2006/0003322 A1* | 1/2006 | Bentwich | 435/6 |
| 2007/0072796 A1* | 3/2007 | Phiasivongsa et al. | 514/12 |
| 2007/0129305 A1* | 6/2007 | Divita | C07K 14/00 514/130 |
| 2007/0134655 A1* | 6/2007 | Bentwich | 435/6 |
| 2008/0113351 A1* | 5/2008 | Naito | A61K 31/713 435/6.11 |
| 2009/0239815 A1* | 9/2009 | Litman | C07H 21/02 514/44 R |
| 2009/0298910 A1 | 12/2009 | Griffey et al. | |

FOREIGN PATENT DOCUMENTS

| | | | | |
|---|---|---|---|---|
| WO | WO 2006113246 A2 * | 10/2006 | | C12N 15/113 |
| WO | WO-2009/018303 A2 | 2/2009 | | |
| WO | WO-2010151755 A2 * | 12/2010 | | A61K 31/7105 |

OTHER PUBLICATIONS

Tada et al., Epigenetic modulation of tumor suppressor CCAAT/enhancer binding protein alpha activity in lung cancer, 2006, Journal of the National Cancer Institute, vol. 98, pp. 396-406.*
Wang et al., Induced ncRNAs allosterically modify RNA-binding proteins in cis to inhibit transcription, 2008, Nature, vol. 454, pp. 126-130.*
Di Ruscio et al., "DNMT1-interacting RNAs block gene-specific DNA methylation." Nature. 503(7476):1-25 (2013).
Schmitz, et al., "Interaction of noncoding RNA with the rDNA promoter mediates recruitment of DNMT3b and silencing of rRNA genes," Genes Dev. 24(20):2264-9 (2010).
International Search Report and Written Opinion for International Patent Application No. PCT/US12/33617, dated Aug. 22, 2012 (10 pages).

(Continued)

*Primary Examiner* — Dana H Shin
(74) *Attorney, Agent, or Firm* — Clark & Elbing LLP

(57) ABSTRACT

The present invention relates to chimeric RNA oligonucleotides that are single-stranded oligonucleotides. These compounds are capable of targeting particular genes and reducing DNA methyltransferase activity. Accordingly, these compounds are particularly useful in the treatment of disease associated with aberrant DNA methyltransferase activity, such as cancer or a genetic disorder.

10 Claims, 42 Drawing Sheets
Specification includes a Sequence Listing.

(56) References Cited

OTHER PUBLICATIONS

Trinklein et al., "Identification and functional analysis of human transcriptional promoters," Genome Res. 13(2):308-12 (2003).
"The Eukaryotic Promoter Database," <http://epd.vital-it.ch/index.php>, retrieved on Feb. 28, 2018 (2 pages).

* cited by examiner

Figure 1J

5' CCGGGACGCAGGCGGCGUCAGGCcucagcGCCAGUGGCGAGGGGCGGCGCGG 3'
Figure 4A
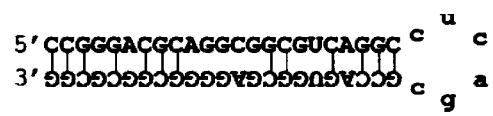
Figure 4B
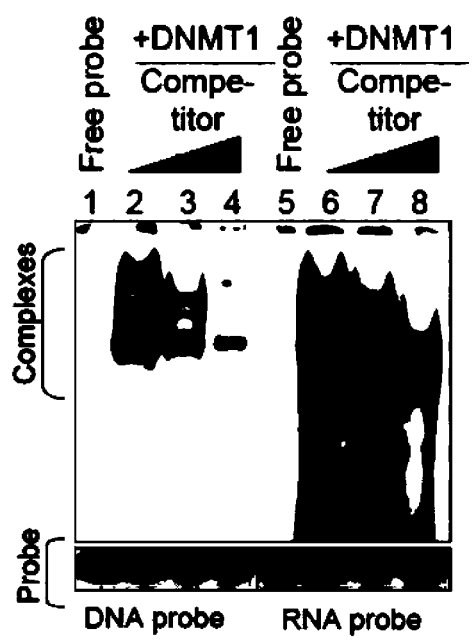
Figure 4C
Figure 4D COBRA analysis Region R1
Alignment: Locations vs. Karyotype
Alignment: Locations vs. Query
1 candidate only.
Figure 7C
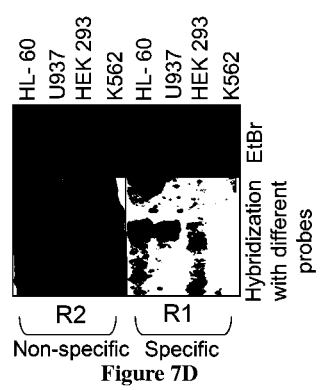
Figure 7D

C/EBPa extra-coding RNA 3' part (SEQ ID NO:1)
```
>/tmp/readseq.in.23787  [Unknown form], 1057 bases, A95 checksum.
ATGTCGGTGTCTTTTTAAAACCAGAAAGAAGCTACTTCCAAGGTTGTCTGTGGGCCAGGTCACATTTGTA
AATAATACAGCATTTTCCCTGGCGGCAATCCTGACTTTCATGAGCTCTCCATCCATCCTGAGCCCCTCTT
ACCCTAAGGGGGTGACTTACTTCCCCCAGGCAAGACAAATAAATAGCAGAGGACAAGGCTCCAAATGGAG
TATGTCCAGAGCCTGAAGGCAGTCTCTTGGGGTCAGGGGAGGGGGCTGAAGGGGTTACTGGGCTGAGGCC
TTGGCGAGGCTTCTTATCTGCCCCGGGGAGGAGGAGAGGGAGTCCTCTGCCTGAGGGGTAGGCCTGGCTA
AGCAGCCCTAGGCTCAAGGAGCCCTTTGTGCAGACTTCCTTGCAAATCACCTACAGCTGCAGCCCTGGCC
ACTCACACACACCGCAGCTCCAGATTCCAGCAGGACCCTCGGCCAGCAGGAAGAGGCCTCCAGTGGTAGG
ACCCTCCAACCCTCTCCTCTTTCCCTAGACCATGTGGCTACACCCTACCCCTGCGAGGCCCGAAGGCAGC
CTGAAGAGAGAGACCCCTCCATCCAGCCCTCCACACCTGCCCAGCCCCAGCCCTCACAAGAAAGGGGGCT
GAGGCAGGCCTGCAACAGGGGTCTGGTCCTGCCCCACACACTGGCTGTTCAAGAACCCACCCAGCATCCA
CACTCCCCACTGCATTCATCCCAGACCCAGCAGGGGACTGAGTGCTGGTGTGCCCCCAACTCCAATGAGC
ACCCTGTAAGGTCAGGCACTCCGGCACCCCCTTAGCAGCAGTGACAGCCAAGCAAGGGAGGGCAGCCCTT
ATCCCTGAACTAACAAGGCCCGGGAGAAAGAGGCCCAGGAGGCTGATGGTGCTTTTCAGATTTTACCCTC
ACGGAGGGTAAAAGATAAATTGCACTTTTCTTTTTTTTTAACTCTGTACCGAGAGAATGTTCACTGAGT
GGCTTACTGTGTGTACCAATGCGGGCTGGGGCATTTTCGAGAAATTACACATTCCTTTTACACTCTGGAA
GCTTAGC
```

Figure 8

SPI1 Sequence #1 (SEQ ID NO:2)
ref|NT_009237.18|  Homo sapiens chromosome 11 genomic contig,
GRCh37.p2 reference primary assembly.
16454 bp at 5' side: transcription factor PU.1 isoform 1
chr11: 47356552-47356358
tmp/readseq.in.14761 [Unknown form], 195 bases, 7C7 checksum.
GAGCGTTTCTCTGGGCCGCTGTGCGGTGCCTGTGGTAATGGGCTGTTGGCGTTTTGCAATGGGCCGGGGG
TGGGGAGGCGGCGCACACATGCTTCCTGTGGTGACTGGGCGCTTCCTGTTTTCTCAGGCGCCGGCCTTGC
TGCTGCCGATGTGGAAACAGGGGCAGCTGCAGCCCGGGCGGCTCCAGGCTGGGCG

SPI1 Sequence #2 (SEQ ID NO:3)
ref|NT_009237.18 Homo sapiens chromosome 11 genomic contig, GRCh37.p2
reference primary assembly
chr11: 47340202-47339789
tmp/readseq.in.14919  [Unknown form], 414 bases, 1431 checksum.
GCCGGCCAGAGACTTCCTGTATGTAGCGCAAGAGATTTATGCAAACGGGTTGGGGCGGTGATGTCACCCC
AAGGGGACTATCTCCCAGCGGCAGGCCCTTCGATAAAATCAGGAACTTGTGCTGGCCCTGCAATGTCAAG
GGAGGGGGCTCACCCAGGGCTCCTGTAGCTCAAGGGGCAGGCCTGAGCCCTGCACCCGCCCCACGACCGT
CCAGCCCCTGACGGGGCACCCCATCCTGAGGGGCTCTGCATTGGCCCCCACCGAGGCAGGGGATCTGACC
GACTCGGAGCCCGGCTGGATGTTACAGGCGTGCAAAATGGAAGGGTTTCCCCTCGTCCCCCCTGTGAGTA
CCGGGACTCCTCCACCAGCCCAACCCGTGGCCCTCGGACGCCTGCCTGCCTGCCCACGAACCCG

SPI1 Sequence #3 (SEQ ID NO:4)
Homo sapiens chromosome 11 genomic contig, GRCh37.p2 reference
primary assembly
chr11: 47342950-47342689
tmp/readseq.in.14747  [Unknown form], 263 bases, 1E21 checksum.
CAATGCAGAAACAGAAAGTCAAATACTGCCTGTTCTCATGTATAAGTAGGAGCTAAATAATGTGTACACA
TGGACATAGAATGTGGAATGACAGACACTGGAGACTTGCAAGGGTGGGAGAGTGGGGAGGCATGGTGAGG
GATGAGAAATTACTTAAAGGGCACAATGTACACTATTCTGGTGATGGATAAACTGAAAGCCTAGACTTCT
CCATTATGCAATATATCCATGGAACAAAACTGCATTTGTACCCCTTACATTTA

SPI1 Sequence #4 (SEQ ID NO:5)
NT_009237.18|  Homo sapiens chromosome 11 genomic contig, GRCh37.p2
reference primary assembly
chr11: 47340198-47339789
tmp/readseq.in.14752  [Unknown form], 410 bases, C07 checksum.
GCCAGAGACTTCCTGTATGTAGCGCAAGAGATTTATGCAAACGGGTTGGGGCGGTGATGTCACCCCAAGG
GGACTATCTCCCAGCGGCAGGCCCTTCGATAAAATCAGGAACTTGTGCTGGCCCTGCAATGTCAAGGGAG
GGGGCTCACCCAGGGCTCCTGTAGCTCAAGGGGCAGGCCTGAGCCCTGCACCCGCCCCACGACCGTCCAG
CCCCTGACGGGGCACCCCATCCTGAGGGGCTCTGCATTGGCCCCCACCGAGGCAGGGGATCTGACCGACT
CGGAGCCCGGCTGGATGTTACAGGCGTGCAAAATGGAAGGGTTTCCCCTCGTCCCCCCTGTGAGTACCGG
GACTCCTCCACCAGCCCAACCCGTGGCCCTCGGACGCCTGCCTGCCTGCCCACGAACCCG

Figure 9

RXRA Sequence #1 (SEQ ID NO:6)
```
ref|NT_019501.13|  Homo sapiens chromosome 9 genomic contig, GRCh37.p2
reference primary assembly
126630-127130
>/tmp/readseq.in.28501   [Unknown form], 501 bases, EC6 checksum.
CGCGCAGACAATGGCCCGGCCGCTGGGCTCCCGGCCCGGCTCTCCGCCTCCTCCGGGCCCTTGCGCGCAA
GTGTGTGTGTGCGCGAGTGTGTGGCGGGCCCGGGGAGGGAGTTCTGCTCCCGCCCCGCCCCGCCCCGC
TCCCTCTGCGCCCCGCCCCCTCCCACGCCGCCTCCTCGCGGCTCCCGGGAACCCCTGGCGGAGGCGAACT
CGCAAGTTTGCACGGCGCTCTCAACTCGGCGGCCGGGCGGGCGGCGATCGCGGGCGGCGGCGGCGGAGG
GGGGCGCGCTCCGGGCGGGGCTGGGCGGGCGGGGCGCGGGCCGAGCGGTGGCGGCGGCGCTGCGCCGAGT
CAGCGCCCGTCGCGGGCCCCCCGCCACCCCCCGCCGGCGCCGCAGCGCCGCGGTCGGAGCGGGGCGCGG
GCGCGCGGCGGCGGGGGCGCGGGCCGGGCGCGCGCGGCGGCGGCGCGCAGACACAAGTAGTTTACATTGT
TGGGCGACTTT
```

RXRA Sequence #2 (SEQ ID NO:7)
```
ref|NT_019501.13|  Homo sapiens chromosome 9 genomic contig, GRCh37.p2
reference primary assembly
127305-127805
>/tmp/readseq.in.28526   [Unknown form], 501 bases, F87 checksum.
GCCGCTCGGTGAGTGCTCGCCGGGCCGGGCGGGGACGGGGCCGGGGGCCGGGGGCCGGCGGGCGGGAGGG
GGCCGGGGCGCGTTGGCGGCGCGCGGGGGGTCGCCGGCCCGGGCCCCGCTCGGACCCCTCGCCGACC
TTCGCGTGAGTTCGGGCGCCGGGCCCGGGGAGGGTCGACCCGGGGCAACTTTTCGCGGGGCCGGGGCGGG
GCTGGGCAGCGGGCGGGCGGCGGGGGCCGGGGGGCGGGTGGCAGGTTCGCCCGGGACGAGGAGGGGTCTCC
CGCTCACCGGCGGCCGCCTGCGCCCCGGCGCCCAGCTGCAGCCGCGCCGCACAGGAACCCGGCCGGAGCG
GGAGGAGCAACTTCTGCGCTCCGCGGCTCCGGCCTCCCTGGCCTGGGGACCGGGACGGCGCGCTGGGCCC
CGAGCGGCCTCTGCGCCGCCCGCCCGTCGGGCTGCGGCTTCTAGCAGGCCGCTGGCCCTTGGGTGTGTGT
CCGCCCAGGAA
```

Figure 10

C/EBPa extra-coding RNA (SEQ ID NO:8)
>/tmp/readseq.in.4654   [Unknown form], 5411 bases, B0A checksum.
ACAGGTGAATGCTATATGAATGGGTCCTGCATTTGGCTCAGCAAGCAGCTCTCCGGCTCACATCGGGATA
TTTATTTAACCTATCTGGTTTTTACTCCCTCCCGTCCAAAAGCGTCAAGCTAAAAATATCTTGTTTATGA
GCTCTGGACCGAAAACGAAGCAGTTGGGCTATTAATCACTGGGACTATGTTGAATAGGAACTTGATTAAA
GCGCAGTGTGCGTTGCCCAGATGAAACTGCTTCTTTACTGCGATCGTCGTGGAAGCTCGGGGCTCTCCAG
CGGTGTTTTTAGCTGTGCCCCCTCCGGGGCTCCTGGGCGGGTCGTGGCGCCTTGCCAGGCCTAAGGCCAC
TGTCGGTGAAGGGGGTCTTCCCTCACCTGTAGGCAAGCGCGCCTCTAGCCGGGACGCAGGCGGCGTCAGG
CCTCAGCGCCAGTGGCGAGGGGCGGCGCGGGCAAGGACAGGAGACACTTGAGGGCTCCCAAGACTCCATC
TGGGCCCAGCTGACGGTCCGTAGCCGCCACCCCGGCCCCGGTAAAGAATGCGAGGGACGCACGTGGCTGG
GGGTCTCGGTGGCAAGCTCCTTCCCCCGCCGCGGTGAGAGCATTAGCTGCCGCACTCAAGGGGCCCCAGG
GCCTGGCCGCCTCGGTCCCTAGGATCCCGGGGACTACAGCGCCCGGCGAACCACTGGGCAGAGTTCTCCC
TGTGCGTGCTCGGACCTGGCAGCCCGGCGGCCTGGACACCCTCGCTCCCGCCGTTGGCGCCCACCTGAAT
GGGGAGGCGGGGAGGAAGCGGTGGCTTCGGGCCTCGAGGGCTGCGGCCCCGCCTCGGAATCCCGGCCC
CAGAGTTAAGTTTGTCTCCTCCCTCGGTGCGCCCTCCCCGTGCTCGCCCGGCGTCCAGCTCCGCTAGT
CTGGGGGCCCCGCGGTCCCGCAGGAAAAAAAATCGGCGACTCCACGCCGGGTAACAGCGCCGGCCCCGC
GCGCCTAGCAAGCCGCGCGCTCCGACCTGGAGAAGTAATTATAAAGAAAGTTTTCCAGCCCGGGCGGATC
GACCGGCCAGGTCCTCCAGGCTCCCGGGCCGAGGCCGCCTCCGCTCCCGCGGGGTCCTAGCGCCCTGCG
CGGCGCCGCCCATGGGACCCCGGCGTCCTCCGAGAGGTACCTCTGCGCGGAATCACAGGGGTAGCCTGGA
GATCAGAGCTAGGAGACGCAGAGCCACCGCGCTCAGGACCTCTCCGCGCGTCCCAAACGGCCCCCCACCG
GCCCCAGCCCCGCTGCTCTGCGCTGCAGCCTCCCCGGGACGCGGGTCCGGGACAGGCCTGGTTCTGGCTT
TGAAAGAGAATCCGCGCCCCAGCAGCTCAAGACCAAGACTCGCCCTCCGCCCCCCACCCCTACCCCGTGC
AGCCTCGGGATACTCCTGGGCTCCCGGCCGTGGCTGGATACGGGCGCCTAGGGCAGGCAGGAGGAGGGGG
CCCCCGCTACCGACCACGTGGGCGCGGGGCGACGGCCGGGCCGGGGCGGAGCTTGGAGCGAGCGCCGC
GGCTCTGCTGGGCGCGCTGGAGGCGGTGGGCGTTGCGCCGCGGCCTGCCTGGGGAGCGCGGCGCTGTGCC
GCGCTGGTTCGCCGCCCCATGCCGGCCGCGCGCTAGGACCCAGCAGGCGCCGCGCCGCCGCAGCCCGGGG
ACAGAGGCCGCCTCGGACTCTAGGGGGCGACGCGGCCTGCCGGGTATAAAAGCTGGGCCGGCGCGGGCCG
GGCCATTCGCGACCCGGAGGTGCGCGGGCGCGGGCGAGCAGGGTCTCCGGGTGGGCGGCGGCGACGCCCC
GCGCAGGCTGGAGGCCGCCGAGGCTCGCCATGCCGGGAGAACTCTAACTCCCCATGGAGTCGGCCGACT
TCTACGAGGCGGAGCCGCGGCCCCCGATGAGCAGCCACCTGCAGAGCCCCCCGCACGCGCCCAGCAGCGC
CGCCTTCGGCTTTCCCCGGGGCGCGGGCCCCGCGCAGCCTCCCGCCCCACCTGCCGCCCCGGAGCCGCTG
GGCGGCATCTGCGAGCACGAGACGTCCATCGACATCAGCGCCTACATCGACCCGGCCGCCTTCAACGACG
AGTTCCTGGCCGACCTGTTCCAGCACAGCCGGCAGCAGGAGAAGGCCAAGGCGGCCGTGGGCCCCACGGG
CGGCGGCGGCGGCGGCGACTTTGACTACCCGGGCGCGCCCGCGGGCCCCGGCGGCGCCGTCATGCCCGGG
GGAGCGCACGGGCCCCGCCCGGCTACGGCTGCGCGGCCGCCGGCTACCTGGACGGCAGGCTGGAGCCCC
TGTACGAGCGCGTCGGGGCGCCGGCGCTGCGGCCGCTGGTGATCAAGCAGGAGCCCCGCGAGGAGGATGA
AGCCAAGCAGCTGGCGCTGGCCGGCCTCTTCCCTTACCAGCCGCCGCCGCCGCCGCCGCCCTCGCACCCG
CACCCGCACCCGCCGCCCGCGCACCTGGCCGCCCGCACCTGCAGTTCCAGATCGCGCACTGCGGCCAGA
CCACCATGCACCTGCAGCCCGGTCACCCCACGCCGCCGCCCACGCCCGTGCCCAGCCCGCACCCCGCGCC
CGCGCTCGGTGCCGCCGGCCTGCCGGGCCTGGCAGCGCGCTCAAGGGGCTGGGCGCCGCGCACCCCGAC
CTCCGCGCGAGTGGCGGCAGCGGCGCGGGCAAGGCCAAGAAGTCGGTGGACAAGAACAGCAACGAGTACC
GGGTGCGGCGCGAGCGCAACAACATCGCGGTGCGCAAGAGCCGCGACAAGGCCAAGCAGCGCAACGTGGA
GACGCAGCAGAAGGTGCTGGAGCTGACCAGTGACAATGACCGCCTGCGCAAGCGGGTGGAACAGCTGAGC
CGCGAACTGGACACGCTGCGGGGCATCTTCCGCCAGCTGCCAGAGAGCTCCTTGGTCAAGGCCATGGGCA
ACTGCGCGTGAGGCGCGCGGCTGTGGGACCGCCCTGGGCCAGCCTCCGGCGGGGACCCAGGGAGTGGTTT
GGGGTCGCCGGATCTCGAGGCTTGCCCGAGCCGTGCGAGCCAGGACTAGGAGATTCCGGTGCCTCCTGAA

FIG. 11A

```
AGCCTGGCCTGCTCCGCGTGTCCCCTCCCTTCCTCTGCGCCGGACTTGGTGCGTCTAAGATGAGGGGGCC
AGGCGGTGGCTTCTCCCTGCGAGGAGGGGAGAATTCTTGGGGCTGAGCTGGGAGCCCGGCAACTCTAGTA
TTTAGGATAACCTTGTGCCTTGGAAATGCAAACTCACCGCTCCAATGCCTACTGAGTAGGGGGAGCAAAT
CGTGCCTTGTCATTTTATTTGGAGGTTTCCTGCCTCCTTCCCGAGGCTACAGCAGACCCCCATGAGAGAA
GGAGGGGAGCAGGCCCGTGGCAGGAGGAGGGCTCAGGGAGCTGAGATCCCGACAAGCCCGCCAGCCCCAG
CCGCTCCTCCACGCCTGTCCTTAGAAAGGGGTGGAAACATAGGGACTTGGGGCTTGGAACCTAAGGTTGT
TCCCCTAGTTCTACATGAAGGTGGAGGGTCTCTAGTTCCACGCCTCTCCCACCTCCCTCCGCACACACCC
CACCCCAGCCTGCTATAGGCTGGGCTTCCCCTTGGGGCGGAACTCACTGCGATGGGGGTCACCAGGTGAC
CAGTGGGAGCCCCCACCCCGAGTCACACCAGAAAGCTAGGTCGTGGGTCAGCTCTGAGGATGTATACCCC
TGGTGGGAGAGGGAGACCTAGAGATCTGGCTGTGGGCGGGCATGGGGGGTGAAGGGCCACTGGGACCCT
CAGCCTTGTTTGTACTGTATGCCTTCAGCATTGCCTAGGAACACGAAGCACGATCAGTCCATCCCAGAGG
GACCGGAGTTATGACAAGCTTTCCAAATATTTTGCTTTATCAGCCGATATCAACACTTGTATCTGGCCTC
TGTGCCCCAGCAGTGCCTTGTGCAATGTGAATGTGCGCGTCTCTGCTAAACCACCATTTTATTTGGTTTT
TGTTTTGTTTTGGTTTTGCTCGGATACTTGCCAAAATGAGACTCTCCGTCGGCAGCTGGGGGAAGGGTCT
GAGACTCCCTTTCCTTTTGGTTTTGGGATTACTTTTGATCCTGGGGGACCAATGAGGTGAGGGGGGTTCT
CCTTTGCCCTCAGCTTTCCCCAGCCCCTCCGGCCTGGGCTGCCCACAAGGCTTGTCCCCAGAGGCCCTG
GCTCCTGGTCGGGAAGGGAGGTGGCCTCCCGCCAACGCATCACTGGGGCTGGGAGCAGGGAAGGACGGCT
TGGTTCTCTTCTTTTGGGGAGAACGTAGAGTCTCACTCTAGATGTTTATGTATTATATCTATAATATAA
ACATATCAAAGTCAATGTCGGTGTCTTTTTAAAACCAGAAAGAAGCTACTTCCAAGGTTGTCTGTGGGCC
AGGTCACATTTGTAAATAATACAGCATTTTCCCTGGCGGCAATCCTGACTTTCATGAGCTCTCCATCCAT
CCTGAGCCCCTCTTACCCTAAGGGGGTGACTTACTTCCCCCAGGCAAGACAAATAAATAGCAGAGGACAA
GGCTCCAAATGGAGTATGTCCAGAGCCTGAAGGCAGTCTCTTGGGGTCAGGGGAGGGGGCTGAAGGGGTT
ACTGGGCTGAGGCCTTGGCGAGGCTTCTTATCTGCCCCGGGGAGGAGGAGAGGGAGTCCTCTGCCTGAGG
GGTAGGCCTGGCTAAGCAGCCCTAGGCTCAAGGAGCCCTTTGTGCAGACTTCCTTGCAAATCACCTACAG
CTGCAGCCCTGGCCACTCACACACACCGCAGCTCCAGATTCCAGCAGGACCCTCGGCCAGCAGGAAGAGG
CCTCCAGTGGTAGGACCCTCCAACCCTCTCCTCTTTCCCTAGACCATGTGGCTACACCCTACCCCTGCGA
GGCCCGAAGGCAGCCTGAAGAGAGAGACCCCTCCATCCAGCCCTCCACACCTGCCCAGCCCCAGCCCTCA
CAAGAAAGGGGGCTGAGGCAGGCCTGCAACAGGGGTCTGGTCCTGCCCCACACACTGGCTGTTCAAGAAC
CCACCCAGCATCCACACTCCCCACTGCATTCATCCCAGACCCAGCAGGGGACTGAGTGCTGGTGTGCCCC
CAACTCCAATGAGCACCCTGTAAGGTCAGGCACTCCGGCACCCCCTTAGCAGCAGTGACAGCCAAGCAAG
GGAGGGCAGCCCTTATCCCTGAACTAACAAGGCCCGGGAGAAAGAGGCCCAGGAGGCTGATGGTGCTTTT
CAGATTTTACCCTCACGGAGGGTAAAAGATAAATTGCACTTTTCTTTTTTTTAACTCTGTACCGAGAG
AATGTTCACTGAGTGGCTTACTGTGTGTACCAATGCGGGCTGGGGCATTTTCGAGAAATTACACATTCCT
TTTACACTCTGGAAGCTTAGC
```

FIG. 11B

RARB extra-coding RNA (SEQ ID NO:9)
```
>ref|NT_022517.18|  Homo sapiens chromosome 3 genomic contig,
GRCh37.p2 reference primary assembly
25407956-25410445
TGTTACACCACAAGTGCCACTTAGCAACTCCACTAGACAGGGCAGTGTTTCAGCATGGGGTGGGGTGCCC
CCTGACAGGCTTTTAAAAGGCCCGGATGCCAATGCACATTCCAACACTATCCACAAAAAGGAGACTGGAG
CAGTGCTCTTCCCTGCATTGGGCAAGGAGACTCTCCCTCCCTGCCTAACCACTTGCCTGCCCTGTTTTGT
GGGAGAATTACAAGTAAATGCTACAGAGGCAGTGGAGAAAAAGGGTGTTTTAATTCCTCTCCAGAGTTT
CCTTTATTTGATGTATGTTGCATCCTTTAAACAAGTTGTGCAAAATGGCTGCAGGGTAGATTGGCTCTCC
CTTTTAAAGCTCTCCATCCGGCTGGGTTTATTTGTAAATACTGCATCTATCCTTCTTAGTGTTTTAGGAC
TGGCTGGAAAGACTCTTCTTCCTGTAGGTTGGGTCAGTGTGAGAGATCTAAAAAATCATTTTCCCTTAAA
ATTACTGTATTTTAATAAAAGGATTGGGCAGGGGCTGGAATGAGAGAAAACTGGTCCTTCAAAATGTAAA
ACTGTCATACTTAAACCAGTTTACAAAATATGCGTTTAATTATGTGGTGGGATGTGTGTAGGTGTATGAT
GAGAGAGGCAACCAACATGGCTATTTGGGGTGCAAGGATGTGGGAACAGGCAAGTAATTTTCACATTGGA
CTTTCATCCTAGGGAGCTGGGTTCTAGTCACAGCTCTGAGCTGTGTGACCTTGGGTAGGTCTCATCTCCC
CGGGGTTTTGTTTCACCAGTTGAACAGTATGAGGATGAGTCACAGCTAACATTTGTTCCATGATATTTAC
CCAGCACCATACAAGTGTTATTTCTGTCCTCCCAGTTAACACTGACGTGGGTAGTATTATATGCCCATTT
TACAGATGAGGAAACTGAAGCCTGAAGAAGTTAAATACTTATCCCAGAACACACAGCTGGTAAGTGGCAG
ACCTGGAATTGGAATCTAGTTCAGTTTGATTCCCCAACCCATGCTCTTGACCACTATACTGTTTTTTCAA
GTCCAGATCTGAAATCTCATTTTCTGTGTGGCTGTGTGTTTGGGACAGGGGTAACCAATTCCTGACTACT
CTATATGCTGCATAGAACCTGGAGAGGATTTTTCAAAGTAAATGAATCTCGAAAGCTGGATTGCAGAGCA
AACGAGTGCAGTCAATTCAGCCAGGGGCTTGCAAGAGGGAGAAAGAGAAAAAGACTGTGGAATGGAAAGT
TTCCCAACCCAAGCCTTTCCCAAGGGGTAGCCATTCTCTGTTCTACAGTTTAGGGCTTGCATGTGCTTTT
TCTGGAGTGGAAAAATACATAAGTTATAAGGAATTTAACAGACAGAAAGGCGCACAGAGGAATTTAAAGT
GTGGGCTGGGGGGCGAGGCGGTGGGCGGGAGGCGAGCGGGCGCAGGCGGAACACCGTTTTCCAAGCTAAG
CCGCCGCAAATAAAAAGGCGTAAAGGGAGAGAAGTTGGTGCTCAACGTGAGCCAGGAGCAGCGTCCCGGC
TCCTCCCCTGCTCATTTTAAAAGCACTTCTTGTATTGTTTTAAGGTGAGAAATAGGAAAGAAAACGCCG
GCTTGTGCGCTCGCTGCCTGCCTCTCTGGCTGTCTGCTTTTGCAGGGCTGCTGGGAGTTTTTAAGCTCTG
TGAGAATCCTGGGAGTTGGTGATGTCAGACTAGTTGGGTCATTTGAAGGTTAGCAGCCCGGGTAGGGTTC
ACCGAAAGTTCACTCGCATATATTAGGCAATTCAATCTTTCATTCTGTGTGACAGAAGTAGTAGGAAGTG
AGCTGTTCAGAGGCAGGAGGGTCTATTCTTTGCCAAAGGGGGACCAGAATTCCCCCATGCGAGCTGTTT
GAGGACTGGGATGCCGAGAACGCGAGCGATCCGAGCAGGGTTTGTCTGGGCACCGTCGGGGTAGGATCCG
GAACGCATTCGGAAGGCTTTTTGCAAGCATTTACTTGGAAGGAGAACTTGGGATCTTTCTGGGAACCCCC
CGCCCCGGCTGGATTGGCCGAGCAAGCCTGGAAAATGTAAATGATCATTTGGATCAATTACAGGCTTTT
AGCTGGCTTGTCTGTCATAATTCATGATTCGGGGCTGGGAAAAAGACCAACAGCCTACGTGCCAAAAAG
GGGCAGAGTTTGATGGAGTTGGGTGGACTTTTCTATGCCATTTGCCTCCACACCTAGAGGATAAGCACTT
TTGCAGACATTCAGTGCAAGGGAGATCATGTTTGACTGTATGGATGTTCTGTCAGTGAGTCCTGGGCAAA
TCCTGGATTTCTACACTGCGAGTCCGTCTTCCTGCATGCTCCAGGAGAAAGCTCTCAAAGCATGCTTCAG
TGGATTGACCCAAACCGAATGGCAGCATCGGCACACTGCTCAATGTAGGTTTATTTTTTTCCCTTCTTCT
ACCAAGAAAAAAAAAATTGTCTCTCTTGCATGCAATAAAG
```

Figure 12

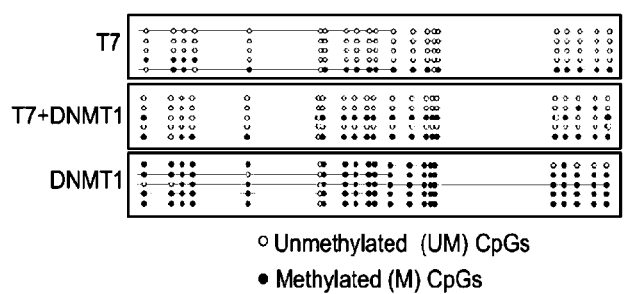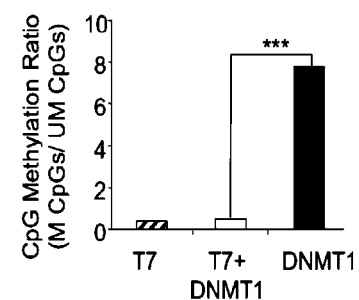
Figure 14A
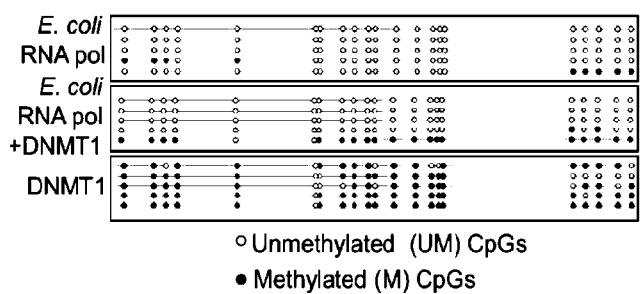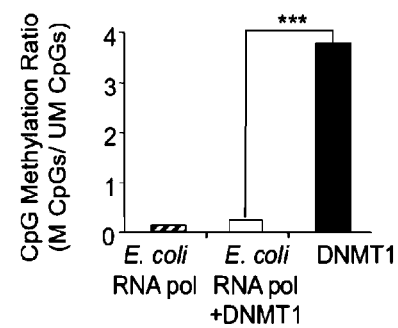
Figure 14B

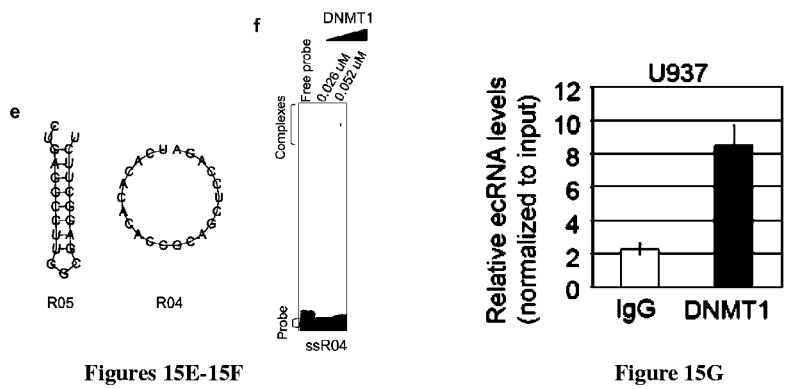
Figures 15E-15F
Figure 15G
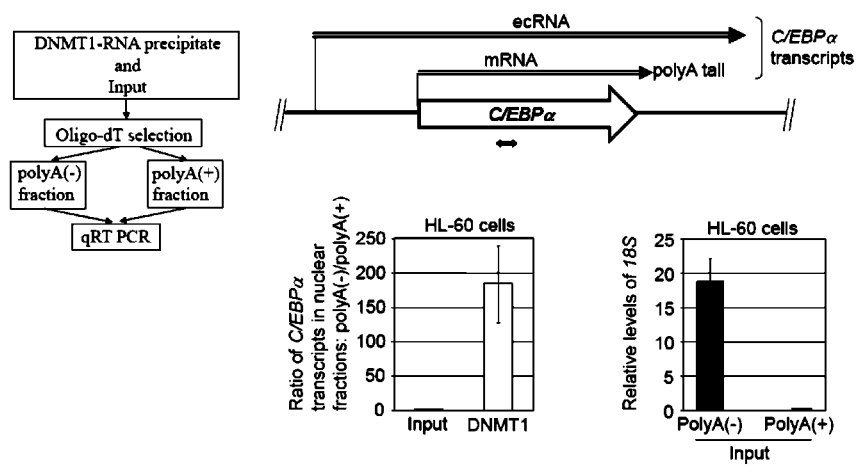
Figure 15H

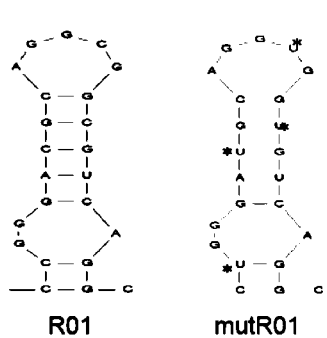
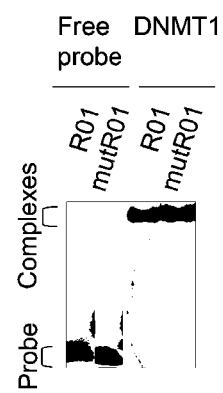
Figure 15K
Figure 15L
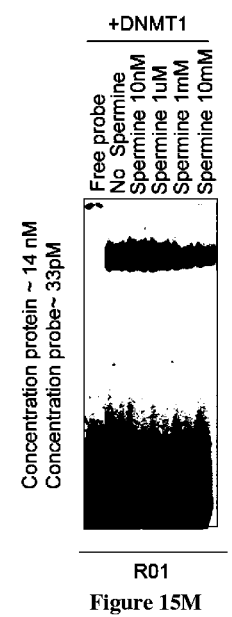
Figure 15M

SEQUENCE LISTING

```
<160> NUMBER OF SEQ ID NOS: 74

<210> SEQ ID NO 1
<211> LENGTH: 1057
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
```

```
atgtcggtgt ctttttaaaa ccagaaagaa gctacttcca aggttgtctg tgggccaggt    60
cacatttgta aataatacag catttcccct ggcggcaatc ctgactttca tgagctctcc   120
atccatcctg agcccctctt accctaaggg ggtgacttac ttcccccagg caagacaaat   180
aaatagcaga ggacaaggct ccaaatggag tatgtccaga gcctgaaggc agtctcttgg   240
ggtcagggga gggggctgaa ggggttactg ggctgaggcc ttggcgaggc ttcttatctg   300
ccccggggag gaggagaggg agtcctctgc ctgaggggta ggcctggcta agcagcccta   360
ggctcaagga gccctttgtg cagacttcct tgcaaatcac ctacagctgc agccctggcc   420
actcacacac accgcagctc cagattccag caggaccctc ggccagcagg aagaggcctc   480
cagtggtagg accctccaac cctctcctct ttccctagac catgtggcta caccctaccc   540
ctgcgaggcc cgaaggcagc ctgaagagag agacccctcc atccagccct ccacacctgc   600
ccagccccag ccctcacaag aaagggggct gaggcaggcc tgcaacaggg gtctggtcct   660
gccccacaca ctggctgttc aagaacccac ccagcatcca cactccccac tgcattcatc   720
ccagacccag caggggactg agtgctggtg tgcccccaac tccaatgagc ccctgtaag   780 gtcaggcact ccggcacccc cttagcagca gtgacagcca agcaagggag ggcagccctt   840
atccctgaac taacaaggcc cgggagaaag aggcccagga ggctgatggt gcttttcaga   900
ttttaccctc acgagggta aaagataaat tgcacttttc ttttttttttt aactctgtac   960 cgagagaatg ttcactgagt ggcttactgt gtgtaccaat gcgggctggg gcattttcga  1020
gaaattacac attccttta cactctggaa gcttagc                            1057
```

<210> SEQ ID NO 2
<211> LENGTH: 195
<212> TYPE: DNA
<213> ORGANISM: Homo sapiens

<400> SEQUENCE: 2

```
gagcgtttct ctgggccgct gtgcggtgcc tgtggtaatg ggctgttggc gttttgcaat    60
gggccggggg tggggaggcg gcgcacacat gcttcctgtg gtgactgggc gcttcctgtt   120
ttctcaggcg ccggccttgc tgctgccgat gtggaaacag gggcagctgc agcccgggcg   180
gctccaggct gggcg                                                    195
```

<210> SEQ ID NO 3
<211> LENGTH: 414
<212> TYPE: DNA
<213> ORGANISM: Homo sapiens

<400> SEQUENCE: 3

```
gccggccaga gacttcctgt atgtagcgca agagatttat gcaaacgggt tggggcggtg    60
atgtcacccc aagggggacta tctcccagcg gcaggccctt cgataaaatc aggaacttgt   120
gctggccctg caatgtcaag ggaggggggct caccccaggggc tcctgtagct caaggggcag   180
ggctgagccc tgcacccgcc ccacgaccgt ccagcccctg acggggcacc ccatcctgag   240
gggctctgca ttggccccca ccgaggcagg ggatctgacc gactcggagc ccggctggat   300
gttacaggcg tgcaaaatgg aagggtttcc cctcgtcccc cctgtgagta ccggactcc   360 tccaccagcc caacccgtgg ccctcggacg cctgcctgcc tgcccacgaa cccg          414
```

<210> SEQ ID NO 4
<211> LENGTH: 263
<212> TYPE: DNA

<213> ORGANISM: Homo sapiens

<400> SEQUENCE: 4

| caatgcagaa acagaaagtc aaatactgcc tgttctcatg tataagtagg agctaaataa | 60 |
| tgtgtacaca tggacataga atgtggaatg acagacactg gagacttgca agggtgggag | 120 |
| agtggggagg catggtgagg gatgagaaat tacttaaagg gcacaatgta cactattctg | 180 |
| gtgatggata aactgaaagc ctagacttct ccattatgca atatatccat ggaacaaaac | 240 |
| tgcatttgta ccccttacat tta | 263 |

<210> SEQ ID NO 5
<211> LENGTH: 410
<212> TYPE: DNA
<213> ORGANISM: Homo sapiens

<400> SEQUENCE: 5

| gccagagact tcctgtatgt agcgcaagag atttatgcaa acgggttggg gcggtgatgt | 60 |
| caccccaagg ggactatctc ccagcggcag gcccttcgat aaaatcagga acttgtgctg | 120 |
| gccctgcaat gtcaagggag ggggctcacc cagggctcct gtagctcaag gggcaggcct | 180 |
| gagccctgca cccgccccac gaccgtccag cccctgacgg ggcacccat cctgaggggc | 240 |
| tctgcattgg cccccaccga ggcagggat ctgaccgact cggagcccgg ctggatgtta | 300 |
| caggcgtgca aaatggaagg gtttcccctc gtcccccctg tgagtaccgg gactcctcca | 360 |
| ccagcccaac ccgtggccct cggacgcctg cctgcctgcc cacgaacccg | 410 |

<210> SEQ ID NO 6
<211> LENGTH: 501
<212> TYPE: DNA
<213> ORGANISM: Homo sapiens

<400> SEQUENCE: 6

| cgcgcagaca atggcccggc cgctgggctc ccggcccggc tctccgcctc ctccgggccc | 60 |
| ttgcgcgcaa gtgtgtgtgt gcgcgagtgt gtggcgggcc cggggaggga gttctgctcc | 120 |
| cgcccccgcc cccgcccgc tccctctgcg ccccgcccc tcccacgccg cctcctcgcg | 180 |
| gctcccggga acccctggcg gaggcgaact cgcaagtttg cacggcgctc tcaactcggc | 240 |
| ggccgggcgg gcgcgatcg cggggcgcg cggcgagg ggggcgcgct ccggcgggg | 300 |
| ctgggcgggc ggggcgcggg ccgagcggtg gcggcggcgc tgcgccgagt cagcgcccgt | 360 |
| cgcgggcccc ccgccacccc ccgccggcg ccgcagcgcc gcggtcggag cggggcgcgg | 420 |
| gcgcgcggcg gcggggcgc gggccgggcg cgcgcggcgg cggcgcgcag acacaagtag | 480 |
| tttacattgt tgggcgactt t | 501 |

<210> SEQ ID NO 7
<211> LENGTH: 501
<212> TYPE: DNA
<213> ORGANISM: Homo sapiens

<400> SEQUENCE: 7

| gccgctcggt gagtgctcgc cgggccgggc ggggacgggg ccgggggccg ggggccggcg | 60 |
| ggcgggaggg ggccggggc gcgttggcgg cgcgcgcggg gggtcgccgg cccgggcccc | 120 |
| gctcggaccc ctcgccgacc ttcgcgtgag ttcgggcgcc gggccgggg agggtcgacc | 180 |
| cggggcaact tttcgcgggg ccggggcggg gctgggcagc gggcgggcgg cggggccggg | 240 |
| gggcgggtgg caggttcgcc cgggacgagg aggggtctcc cgctcaccgg cggccgcctg | 300 |

```
cgccccggcg cccagctgca gccgcgccgc acaggaaccc ggccggagcg ggaggagcaa      360
cttctgcgct ccgcggctcc ggcctccctg gcctggggac cggacggcg cgctgggccc       420 cgagcggcct ctgcgccgcc cgcccgtcgg gctgcggctt ctagcaggcc gctggccctt      480
gggtgtgtgt ccgcccagga a                                                501

<210> SEQ ID NO 8
<211> LENGTH: 5411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
acaggtgaat gctatatgaa tgggtcctgc atttggctca gcaagcagct ctccggctca       60
catcgggata tttatttaac ctatctggtt tttactccct cccgtccaaa agcgtcaagc      120 taaaatatc ttgtttatga gctctggacc gaaaacgaag cagttgggct attaatcact       180
gggactatgt tgaataggaa cttgattaaa gcgcagtgtg cgttgcccag atgaaactgc      240
ttctttactg cgatcgtcgt ggaagctcgg ggctctccag cggtgttttt agctgtgccc      300
cctccggggc tcctgggcgg gtcgtggcgc cttgccaggc ctaaggccac tgtcggtgaa      360
gggggtcttc cctcacctgt aggcaagcgc gcctctagcc gggacgcagg cggcgtcagg      420
cctcagcgcc agtggcgagg ggcggcgcgg gcaaggacag gagacacttg agggctccca      480
agactccatc tgggcccagc tgacggtccg tagccgccac cccggccccg gtaaagaatg      540
cgagggacgc acgtggctgg gggtctcggt ggcaagctcc ttcccccgcc gcggtgagag      600
cattagctgc cgcactcaag gggccccagg gcctggccgc ctcggtccct aggatcccgg      660
ggactacagc gcccggcgaa ccactgggca gagttctccc tgtgcgtgct cggacctggc      720
agcccggcgg cctggacacc ctcgctcccg ccgttggcgc ccacctgaat ggggaggcgg      780
gggaggaagc ggtggcttcg ggcctcgagg gctgcggccc ccgcctcgga atcccggccc      840
cagagttaag tttgtctcct ccctcggtgc gcccctcccc gtgctcgccc cggcgtccag      900
ctccgctagt ctgggggggcc ccgcggtccc gcaggaaaaa aaatcggcga ctccacgccg      960
ggtaacagcg ccgccccgc gcgcctagca agccgcgcgc tccgacctgg agaagtaatt     1020
ataaagaaag ttttccagcc cgggcggatc gaccggccag gtcctccagg ctcccgggcc     1080
gaggccgcct ccgctccccg cggggtccta gcgccctgcg cggcgccgcc catgggaccc     1140
cggcgtcctc cgagaggtac ctctgcgcgg aatcacaggg gtagcctgga gatcagagct     1200
aggagacgca gagccaccgc gctcaggacc tctccgcgcg tcccaaacgg ccccccaccg     1260
gccccagccc cgctgctctg cgctgcagcc tccccgggac gcgggtccgg acaggcctg     1320 gttctggctt tgaaagagaa tccgcgcccc agcagctcaa gaccaagact cgccctccgc     1380
ccccaccccc taccccgtgc agcctcggga tactcctggg ctcccggccg tggctggata     1440
cgggcgccta gggcaggcag gaggaggggg ccccgctac cgaccacgtg ggcgcggggg      1500
cgacggccgg gccgggggcg gagcttggag cgagcgccgc ggctctgctg ggcgcgctgg     1560
aggcggtggg cgttgcgccg cggcctgcct ggggagcgcg gcgctgtgcc gcgctggttc     1620
gccgccccat gccggccgcg cgctaggacc cagcaggcgc cgccgccgcc cagcccgggg     1680
acagaggccg cctcggactc taggggggcga cgcggcctgc cgggtataaa agctgggccg     1740
gcgcgggccg ggccattcgc gacccggagg tgcgcgggcg cgggcgagca gggtctccgg     1800
```

-continued

```
gtgggcggcg gcgacgcccc gcgcaggctg gaggccgccg aggctcgcca tgccgggaga    1860
actctaactc ccccatggag tcggccgact tctacgaggc ggagccgcgg cccccgatga    1920
gcagccacct gcagagcccc ccgcacgcgc ccagcagcgc cgccttcggc tttccccggg    1980
gcgcgggccc cgcgcagcct cccgcccac ctgccgcccc ggagccgctg gcggcatct      2040 gcgagcacga cgtccatc gacatcagcg cctacatcga cccggccgcc ttcaacgacg      2100
agttcctggc cgacctgttc cagcacagcc ggcagcagga gaaggccaag gcggccgtgg    2160
gccccacggg cggcggcggc ggcggcgact ttgactaccc gggcgcgccc gcgggccccg    2220
gcggcgccgt catgcccggg ggagcgcacg gccccccgcc cggctacggc tgcgcggccg    2280
ccggctacct ggacggcagg ctggagcccc tgtacgagcg cgtcggggcg ccggcgctgc    2340
ggccgctggt gatcaagcag gagccccgcg aggaggatga agccaagcag ctggcgctgg    2400
ccggcctctt cccttaccag ccgccgccgc cgccgccgcc ctcgcacccg cacccgcacc    2460
cgccgcccgc gcacctggcc gccccgcacc tgcagttcca gatcgcgcac tgcggccaga    2520
ccaccatgca cctgcagccc ggtcacccca cgccgccgcc cacgcccgtg cccagcccgc    2580
accccgcgcc cgcgctcggt gccgccgcc tgccgggccc tggcagcgcg ctcaaggggc     2640
tgggcgccgc gcaccccgac ctccgcgcga gtggcggcag cggcgcgggc aaggccaaga    2700
agtcggtgga caagaacagc aacgagtacc gggtgcggcg cgagcgcaac aacatcgcgg    2760
tgcgcaagag ccgcgacaag gccaagcagc gcaacgtgga gacgcagcag aaggtgctgg    2820
agctgaccag tgacaatgac cgcctgcgca agcgggtgga acagctgagc cgcgaactgg    2880
acacgctgcg gggcatcttc cgccagctgc cagagagctc cttggtcaag gccatgggca    2940
actgcgcgtg aggcgcgcgg ctgtgggacc gccctgggcc agcctccggc ggggacccag    3000
ggagtggttt ggggtcgccg gatctcgagg cttgcccgag ccgtgcgagc caggactagg    3060
agattccggt gcctcctgaa agcctggcct gctccgcgtg tccctccct tcctctgcgc     3120 cggacttggt gcgtctaaga tgaggggcc aggcggtggc ttctccctgc gaggagggga    3180
gaattcttgg ggctgagctg ggagcccggc aactctagta tttaggataa ccttgtgcct    3240
tggaaatgca aactcaccgc tccaatgcct actgagtagg gggagcaaat cgtgccttgt    3300
cattttattt ggaggtttcc tgcctccttc ccgaggctac agcagacccc catgagagaa    3360
ggaggggagc aggcccgtgg caggaggagg gctcaggag ctgagatccc gacaagcccg     3420
ccagccccag ccgctcctcc acgcctgtcc ttagaaaggg gtggaaacat agggacttgg    3480
ggcttggaac ctaaggttgt tcccctagtt ctacatgaag gtggagggtc tctagttcca    3540
cgcctctccc acctccctcc gcacacaccc caccccagcc tgctataggc tgggcttccc    3600
cttggggcgg aactcactgc gatggggtc accaggtgac cagtgggagc ccccaccccg     3660
agtcacacca gaaagctagg tcgtgggtca gctctgagga tgtataccc tggtgggaga     3720 gggagaccta gagatctggc tgtgggcgg gcatgggggg tgaagggcca ctgggaccct     3780
cagccttgtt tgtactgtat gccttcagca ttgcctagga acacgaagca cgatcagtcc    3840
atcccagagg gaccggagtt atgacaagct ttccaaatat tttgctttat cagccgatat    3900
caacacttgt atctggcctc tgtgccccag cagtgccttg tgcaatgtga atgtgcgcgt    3960
ctctgctaaa ccaccatttt atttggtttt tgttttgttt tggttttgct cggatacttg    4020
ccaaaatgag actctccgtc ggcagctggg ggaagggtct gagactccct ttccttttgg    4080 tttttgggatt actttttgatc ctgggggacc aatgaggtga ggggggttct cctttgccct   4140
```

```
cagctttccc cagcccctcc ggcctgggct gcccacaagg cttgtccccc agaggccctg   4200
gctcctggtc gggaagggag gtggcctccc gccaacgcat cactgggct gggagcaggg    4260 aaggacggct tggttctctt cttttgggga aacgtagag tctcactcta gatgttttat    4320
gtattatatc tataatataa acatatcaaa gtcaatgtcg gtgtcttttt aaaaccagaa   4380
agaagctact tccaaggttg tctgtgggcc aggtcacatt tgtaaataat acagcatttt   4440
ccctggcggc aatcctgact ttcatgagct ctccatccat cctgagcccc tcttacccta   4500
agggggtgac ttacttcccc caggcaagac aaataaatag cagaggacaa ggctccaaat   4560
ggagtatgtc cagagcctga aggcagtctc ttggggtcag gggaggggc tgaaggggtt    4620 actgggctga ggccttggcg aggcttctta tctgccccgg ggaggaggag agggagtcct   4680
ctgcctgagg gtaggcctg gctaagcagc cctaggctca aggagccctt tgtgcagact    4740
tccttgcaaa tcacctacag ctgcagccct ggccactcac acacaccgca gctccagatt   4800
ccagcaggac cctcggccag caggaagagg cctccagtgg taggaccctc caaccctctc   4860
ctctttccct agaccatgtg ctacaccct accctgcga ggcccgaagg cagcctgaag     4920
agagagaccc ctccatccag ccctccacac ctgcccagcc ccagccctca caagaaaggg   4980
ggctgaggca ggcctgcaac aggggtctgg tcctgcccca cacactggct gttcaagaac   5040
ccacccagca tccacactcc ccactgcatt catcccagac ccagcagggg actgagtgct   5100
ggtgtgcccc caactccaat gagcaccctg taaggtcagg cactccggca cccccttagc   5160
agcagtgaca gccaagcaag ggagggcagc ccttatccct gaactaacaa ggcccgggag   5220
aaagaggccc aggaggctga tggtgctttt cagattttac cctcacggag ggtaaaagat   5280
aaattgcact tttctttttt ttttaactct gtaccgagag aatgttcact gagtggctta   5340
ctgtgtgtac caatgcgggc tggggcattt tcgagaaatt acacattcct tttacactct   5400
ggaagcttag c                                                       5411

<210> SEQ ID NO 9
<211> LENGTH: 2490
<212> TYPE: DNA
<213> ORGANISM: Homo sapiens

<400> SEQUENCE: 9
tgttacacca caagtgccac ttagcaactc cactagacag ggcagtgttt cagcatgggg      60
tggggtgccc cctgacaggc ttttaaaagg cccggatgcc aatgcacatt ccaacactat     120
ccacaaaaag gagactggag cagtgctctt ccctgcattg gcaaggaga ctctccctcc      180 ctgcctaacc acttgcctgc cctgtttgt gggagaatta caagtaaatg ctacagaggc      240
agtggagaaa aaagggtgtt ttaattcctc tccagagttt cctttatttg atgtatgttg     300
catcctttaa acaagttgtg caaaatggct gcagggtaga ttggctctcc cttttaaagc     360
tctccatccg gctgggttta tttgtaaata ctgcatctat ccttcttagt gttttaggac     420
tggctggaaa gactcttctt cctgtaggtt gggtcagtgt gagagatcta aaaaatcatt     480
ttcccttaaa attactgtat tttaataaaa ggattgggca ggggctggaa tgagagaaaa     540
ctggtccttc aaaatgtaaa actgtcatac ttaaaccagt ttacaaaata tgcgtttaat     600
tatgtggtgg gatgtgtgta ggtgtatgat gagagaggca accaacatgg ctatttgggg     660
tgcaaggatg tgggaacagg caagtaaattt tcacattgga cttcatcct agggagctgg    720 gttctagtca cagctctgag ctgtgtgacc ttgggtaggt ctcatctccc cggggttttg     780
tttcaccagt tgaacagtat gaggatgagt cacagctaac atttgttcca tgatatttac     840
```

```
ccagcaccat acaagtgtta tttctgtcct cccagttaac actgacgtgg gtagtattat      900
atgcccattt tacagatgag gaaactgaag cctgaagaag ttaaatactt atcccagaac      960
acacagctgg taagtggcag acctggaatt ggaatctagt tcagtttgat tccccaaccc     1020
atgctcttga ccactatact gttttttcaa gtccagatct gaaatctcat tttctgtgtg     1080
gctgtgtgtt tgggacaggg gtaaccaatt cctgactact ctatatgctg catagaacct     1140
ggagaggatt tttcaaagta aatgaatctc gaaagctgga ttgcagagca aacgagtgca     1200
gtcaattcag ccaggggctt gcaagaggga gaaagagaaa aagactgtgg aatggaaagt     1260
ttcccaaccc aagcctttcc caaggggtag ccattctctg ttctacagtt tagggcttgc     1320
atgtgctttt tctggagtgg aaaaatacat aagttataag gaatttaaca gacagaaagg     1380
cgcacagagg aatttaaagt gtgggctggg gggcgaggcg gtgggcggga ggcgagcggg     1440
cgcaggcgga acaccgtttt ccaagctaag ccgccgcaaa taaaaaggcg taaagggaga     1500
gaagttggtg ctcaacgtga gccaggagca gcgtcccggc tcctcccctg ctcattttaa     1560
aagcacttct tgtattgttt ttaaggtgag aaataggaaa gaaaacgccg gcttgtgcgc     1620
tcgctgcctg cctctctggc tgtctgcttt tgcagggctg ctgggagttt ttaagctctg     1680
tgagaatcct gggagttggt gatgtcagac tagttgggtc atttgaaggt tagcagcccg     1740
ggtagggttc accgaaagtt cactcgcata tattaggcaa ttcaatcttt cattctgtgt     1800
gacagaagta gtaggaagtg agctgttcag aggcaggagg gtctattctt tgccaaaggg     1860
gggaccagaa ttcccccatg cgagctgttt gaggactggg atgccgagaa cgcgagcgat     1920
ccgagcaggg tttgtctggg caccgtcggg gtaggatccg gaacgcattc ggaaggcttt     1980
ttgcaagcat ttacttggaa ggagaacttg ggatctttct gggaaccccc cgcccccggct    2040 ggattggccg agcaagcctg gaaaatggta aatgatcatt tggatcaatt acaggctttt     2100
agctggcttg tctgtcataa ttcatgattc ggggctggga aaaagaccaa cagcctacgt     2160
gccaaaaaag gggcagagtt tgatggagtt gggtggactt ttctatgcca tttgcctcca     2220
cacctagagg ataagcactt ttgcagacat tcagtgcaag ggagatcatg tttgactgta     2280
tggatgttct gtcagtgagt cctgggcaaa tcctggattt ctacactgcg agtccgtctt     2340
cctgcatgct ccaggagaaa gctctcaaag catgcttcag tggattgacc caaaccgaat     2400
ggcagcatcg gcacactgct caatgtaggt ttatttttt cccttcttct accagaaaa      2460 aaaaaattgt ctctcttgca tgcaataaag                                      2490

<210> SEQ ID NO 10
<211> LENGTH: 318
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
ccgctcctcc acgcctgtcc ttagaaaggg gtggaaacat agggacttgg ggcttggaac       60
ctaaggttgt tcccctagtt ctacatgaag gtggagggtc tctagttcca cgcctctccc      120
acctccctcc gcacacaccc caccccagcc tgctataggc tgggcttccc cttggggcgg      180
aactcactgc gatggggtc accaggtgac cagtgggagc ccccacccg agtcacacca        240 gaaagctagg tcgtgggtca gctctgagga tgtatacccc tggtgggaga gggagaccta      300
gagatctggc tgtggggc                                                    318
```

<210> SEQ ID NO 11
<211> LENGTH: 481
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11

```
gtcacatttg taaataatac agcattttcc ctggcggcaa tcctgacttt catgagctct     60
ccatccatcc tgagcccctc ttaccctaag ggggtgactt acttccccca ggcaagacaa    120
ataaatagca gaggacaagg ctccaaatgg agtatgtcca gagcctgaag gcagtctctt    180
ggggtcaggg gaggggggctg aaggggttac tgggctgagg ccttggcgag gcttcttatc    240
tgccccgggg aggaggagag ggagtcctct gcctgagggg taggcctggc taagcagccc    300
taggctcaag gagcccttg tgcagacttc cttgcaaatc acctacagct gcagccctgg    360
ccactcacac acaccgcagc tccagattcc agcaggaccc tcggcagca ggaagaggcc    420
tccagtggta ggaccctcca accctctcct ctttccctag accatgtggc tacaccctac    480
c                                                                    481
```

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
agaggcgcgc ttgcctacag gtga                                            24
```

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
ctcgccactg gcgctgaggc ctga                                            24
```

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
gagtcttggg agccctcaag tgtct                                           25
```

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

-continued gtcacatttg taaataatac agca                                    24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccctggcggc aatcctgact ttca                                    24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcatgagctc tccatccatc ctga                                    24

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tcggtggaca agaacag                                            17

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcaggcggtc attg                                               14

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
acaaggccaa gcagcgc                                            17

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggttgtctgt gggccaggtc a                                          21

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agagctcatg aaagtcagga ttg                                        23

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
aataatacag cattttccct ggcgg                                      25

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggctagagga gcaggtacat                                            20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcctgggtat ggataacact a                                          21

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
cgacaccact catgtcaatg gctg                                       24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccgctcctcc acgcctgtcc ttag                                       24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gccccacagc cagatctcta ggtc                                          24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tcatgagctc tccatccatc ctga                                          24

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctggccgagg gtcctgctgg aatc                                          24

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
atctcgcttg ggcgagagta a                                             21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
aataaatagc agaggacaag g                                             21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
caggcaagac aaataaatag c                                             21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
gaagaggcct ccagtggtag g                                              21

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 35
atgtcggtgt ctttttaaaa ccag                                           24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 36
gctaagcttc cagagtgtaa aagg                                           24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 37
cccggcccca gagttaagtt tgtc                                           24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 38
cggcccagct tttatacccg gcag                                           24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 39
tatacagcca tgaaagaaac ttac                                           24

```
<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agttttactg tggtgtgttt gttc                                            24

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ggtgttttta gttgtgtttt ttt                                             23

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aaaccctaaa acccctta                                                   18

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tagtttygtt agtttggggg gttt                                            24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tctaatctcc aaactacccc tata                                            24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aggttaaggy ggttgtgggt ttta                                            24

<210> SEQ ID NO 46
```

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccaactactt aacttcatcc tcct                                          24

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aggttygtgg taggaggagg gttta                                         25

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48 taocccacra cctaactttc taat                                          24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gtgggyggtt tygtygggtt ttgt                                          24

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
acccctaaac raattatata aa                                            22

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gaagtgaatt ttttaaaatg attt                                          24

<210> SEQ ID NO 52
<211> LENGTH: 29

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ttttgtttta gtttttttaag tagttggga                                         29

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggaagggcga tcggtgcggg cctc                                               24

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(24)
<223> OTHER INFORMATION: 5'-Biotin

<400> SEQUENCE: 54
cagccctcga ggcccgaagc cacc                                               24

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cagccctcga ggcccgaagc cacc                                               24

<210> SEQ ID NO 56
<211> LENGTH: 4
<212> TYPE: PRT
<213> ORGANISM: Unknown
<220> FEATURE:
<223> OTHER INFORMATION: Description of Unknown: 'DEAD' box motif
      peptide sequence

<400> SEQUENCE: 56

Asp Glu Ala Asp
1

<210> SEQ ID NO 57
<211> LENGTH: 4
<212> TYPE: PRT
<213> ORGANISM: Unknown
<220> FEATURE:
<223> OTHER INFORMATION: Description of Unknown: 'DEAH' box motif
      peptide sequence

<400> SEQUENCE: 57

Asp Glu Ala His
```

<210> SEQ ID NO 58
<211> LENGTH: 1980
<212> TYPE: DNA
<213> ORGANISM: Homo sapiens

<400> SEQUENCE: 58

```
gagttcccga tctctgggca ggcaacagca gctgtgcaaa aaaggccaga catcgccttc      60
ctcccacaac tccacaggcc gggaaccgtg catgtacagt ggcgtttctt tgttcctagg     120
taggaaaagc cattagtttt agcaccgcag aaaaaaacgc aaatcgctct tggtgctttt     180
tgatttccgt ccaggtctcc ctccacaggt gaatgctata tgaatgggtc ctgcatttgg     240
ctcagcaagc agctctccgg ctcacatcgg gatatttatt taacgtatct ggttttact      300
ccctcccgtc aaaagcgtc aagctaaaaa tatcttgttt atgagctctg gaccgaaaac      360
gaagcagttg ggctattaat cactgggact atgttgaata ggaacttgat taaagcgcag     420
tgtgcgttgc ccagatgaaa ctgcttcttt actgcgatcg tcgtgaaagc tcggggctct     480
ccagcggtgt ttttagctgt gcccctccg gggctcctgg gcgggtcgtg gcgccttgcc      540
aggcctaagg ccactgtcgg tgaagggggt cttccctcac ctgtaggcaa gcgcgcctct     600
agccgggacg caggcggcgt caggcctcag cgccagtggc gaggggcggc gcgggcaagg     660
acaggagaca cttgagggct ccaagactc catctgggcc cagctgacgg tccgtagccg      720
ccacccggc cccggtaaag aatgcgaggg acgcacgtgg ctgggggtct cggtggcaag      780
ctccttcccc cgccgcggtg agagcattag ctgccgcact caaggggccc cagggcctgg     840
ccgcctcggt ccctaggatc ccggggacta cagcgcccgg cgaaccactg ggcagagttc     900
tccctgtgcg tgctcggacc tggcagcccg cgggcctgga caccctcgct cccgccgttg     960
gcgcccacct gaatggggag gcgggggagg aagcggtggc ttcgggcctc gagggctgcg    1020
gcccccgcct cggaatcccg gccccagagt taagtttgtc tcctccctcg gtgcgccct    1080
ccccgtgctc gccccggcgt ccagctccgc tagtctgggg ggccccgcgg tcccgcagga    1140
aaaaaaatcg gcgactccac gccgggtaac agcgccggcc ccgcgcgcct agcaagccgc    1200
gcgctccgac ctggagaagt aattataaag aaagttttcc agcccgggcg gatcgaccgg    1260
ccaggtcctc caggctcccg ggccgaggcc gcctccgctc cccgcggggt cctagcgccc    1320
tgcgcggcgc cgcccatggg accccggcgt cctccgagag gtacctctgc gcggaatcac    1380
aggggtagcc tggagatcag agctaggaga cgcagagcca ccgcgctcag gacctctccg    1440
cgcgtcccaa acggcccccc accggcccca gccccgctgc tctgcgctgc agcctccccg    1500
ggacgcgggt ccgggacagg cctggttctg gctttgaaag agaatccgcg ccccagcagc    1560
tcaagaccaa gactcgccct ccgcccccca ccctacccc gtgcagcctc gggatactcc     1620
tgggctcccg gccgtggctg gatacgggcg cctaggcag gcaggaggag ggggcccccg     1680
ctaccgacca cgtgggcgcg ggggcgacgg ccgggccggg ggcggagctt ggagcgagcg    1740
ccgcggctct gctgggcgcg ctggaggcgg tgggcgttgc gccgcggcct gcctggggag    1800
cgcggcgctg tgccgcgctg gttcgccgcc ccatgccggc cgcgcgctag gacccagcag    1860
gcgccgcgcc gccgcagccc ggggacagag gccgcctcgg actctagggg gcgacgcggc    1920
ctgccgggta taaagctggg gccggcgcgg gccgggccat tcgcgacccg gaggtgcgcg    1980
```

<210> SEQ ID NO 59
<211> LENGTH: 1440

```
<212> TYPE: DNA
<213> ORGANISM: Homo sapiens

<400> SEQUENCE: 59
aaggcttgtc ccccagaggc cctggctcct ggtcgggaag ggaggtggcc tcccgccaac      60
gcatcactgg ggctgggagc agggaaggac ggcttggttc tcttcttttg gggagaacgt     120
agagtctcac tctagatgtt ttatgtatta tatctataat ataaacatat caaagtcaat     180
gtcggtgtct ttttaaaacc agaaagaagc tacttccaag gttgtctgtg ggccaggtca     240
catttgtaaa taatacagca ttttccctgg cggcaatcct gactttcatg agctctccat     300
ccatcctgag cccctcttac cctaaggggg tgacttactt cccccaggca agacaaataa     360
atagcagagg acaaggctcc aaatggagta tgtccagagc ctgaaggcag tctcttgggg     420
tcaggggagg gggctgaagg ggttactggg ctgaggcctt ggcgaggctt cttatctgcc     480
ccggggagga ggagagggag tcctctgcct gaggggtagg cctggctaag cagccctagg     540
ctcaaggagc cctttgtgca gacttccttg caaatcacct acagctgcag ccctggccac     600
tcacacacac cgcagctcca gattccagca ggaccctcgg ccagcaggaa gaggcctcca     660
gtggtaggac cctccaaccc tctcctcttt ccctagacca tgtggctaca ccctacccct     720
gcgaggcccg aaggcagcct gaagagagag acccctccat ccagccctcc acctgccc      780
agccccagcc ctcacaagaa aggggctga ggcaggcctg caacaggggt ctggtcctgc     840
cccacacact ggctgttcaa gaacccaccc agcatccaca ctccccactg cattcatccc     900
agacccagca ggggactgag tgctggtgtg cccccaactc caatgagcac cctgtaaggt     960
caggcactcc ggcaccccct tagcagcagt gacagccaag caagggaggg cagcccttat    1020
ccctgaacta acaaggcccg ggagaaagag gcccaggagg ctgatggtgc ttttcagatt    1080
ttaccctcac ggagggtaaa agataaattg cacttttctt ttttttttaa ctctgtaccg    1140
agagaatgtt cactgagtgg cttactgtgt gtaccaatgc gggctggggc attttcgaga    1200
aattacacat tcctttaca ctctggaagc ttagctttac ctgcctgcgt ggttagctgg    1260
caccccttcc ggcccccac tctgtcctgt gtctggccgc ctcctcaccc acggccgccc    1320
ttggcagagg agaggccacg agcccagtga ggaggcggcg cctgccccgc caccctggga    1380
acagaggagg cagagccccg ccgcgtgccc cgaggcctgg ggcaggtcgc agcttgctaa    1440

<210> SEQ ID NO 60
<211> LENGTH: 52
<212> TYPE: RNA
<213> ORGANISM: Homo sapiens

<400> SEQUENCE: 60
ccgggacgca ggcggcguca ggccucagcg ccaguggcga ggggcggcgc gg              52

<210> SEQ ID NO 61
<211> LENGTH: 23
<212> TYPE: DNA
<213> ORGANISM: Homo sapiens

<400> SEQUENCE: 61
ccgggacgca ggcggcgtca ggc                                             23

<210> SEQ ID NO 62
<211> LENGTH: 22
<212> TYPE: RNA
<213> ORGANISM: Homo sapiens
```

-continued

<400> SEQUENCE: 62
cugaggccuu ggcgaggcuu cu					22

<210> SEQ ID NO 63
<211> LENGTH: 22
<212> TYPE: RNA
<213> ORGANISM: Homo sapiens

<400> SEQUENCE: 63
ucacacacac cgcagcucca ga					22

<210> SEQ ID NO 64
<211> LENGTH: 22
<212> TYPE: DNA
<213> ORGANISM: Homo sapiens

<400> SEQUENCE: 64
ctgaggcctt ggcgaggctt ct					22

<210> SEQ ID NO 65
<211> LENGTH: 22
<212> TYPE: DNA
<213> ORGANISM: Homo sapiens
<220> FEATURE:
<221> NAME/KEY: modified_base
<222> LOCATION: (13)..(13)
<223> OTHER INFORMATION: Methylated

<400> SEQUENCE: 65
ctgaggcctt ggcgaggctt ct					22

<210> SEQ ID NO 66
<211> LENGTH: 22
<212> TYPE: DNA
<213> ORGANISM: Homo sapiens
<220> FEATURE:
<221> NAME/KEY: modified_base
<222> LOCATION: (13)..(13)
<223> OTHER INFORMATION: Methylated

<400> SEQUENCE: 66
ctgaggcctt ggcgaggctt ct					22

<210> SEQ ID NO 67
<211> LENGTH: 23
<212> TYPE: DNA
<213> ORGANISM: Homo sapiens

<400> SEQUENCE: 67
gccagtggcg aggggcggcg cgg					23

<210> SEQ ID NO 68
<211> LENGTH: 23
<212> TYPE: RNA
<213> ORGANISM: Homo sapiens

<400> SEQUENCE: 68
ccgggacgca ggcggcguca ggc					23

<210> SEQ ID NO 69
<211> LENGTH: 23
<212> TYPE: RNA
<213> ORGANISM: Homo sapiens

<400> SEQUENCE: 69

```
cugggaugca ggugguguca ggc                                              23

<210> SEQ ID NO 70
<211> LENGTH: 23
<212> TYPE: DNA
<213> ORGANISM: Homo sapiens

<400> SEQUENCE: 70
gcctgacgcc gcctgcgtcc cgg                                              23

<210> SEQ ID NO 71
<211> LENGTH: 22
<212> TYPE: DNA
<213> ORGANISM: Homo sapiens

<400> SEQUENCE: 71
agaagcctcg ccaaggcctc ag                                               22

<210> SEQ ID NO 72
<211> LENGTH: 22
<212> TYPE: DNA
<213> ORGANISM: Homo sapiens

<400> SEQUENCE: 72
agaagcctcg ccaaggcctc ag                                               22

<210> SEQ ID NO 73
<211> LENGTH: 22
<212> TYPE: DNA
<213> ORGANISM: Homo sapiens
<220> FEATURE:
<221> NAME/KEY: modified_base
<222> LOCATION: (9)..(9)
<223> OTHER INFORMATION: Methylated

<400> SEQUENCE: 73
agaagcctcg ccaaggcctc ag                                               22

<210> SEQ ID NO 74
<211> LENGTH: 23
<212> TYPE: DNA
<213> ORGANISM: Homo sapiens

<400> SEQUENCE: 74
ccgcgccgcc cctcgccact cgc                                              23
```

METHODS AND COMPOSITIONS FOR GENE-SPECIFIC DEMETHYLATION BY DNA METHYLTRANSFERASE (DNMT)-RNA INTERACTION

CROSS-REFERENCE TO RELATED APPLICATION

The present application is the U.S. National Stage of International Application No. PCT/US2012/033617, filed Apr. 13, 2012, which claims the benefit of U.S. Provisional Application No. 61/475,566, filed Apr. 14, 2011, both of which are hereby incorporated by reference in their entirety.

BACKGROUND OF THE INVENTION

The invention relates to gene-specific chimeric RNA oligonucleotides and various uses thereof, including methods of treating cancer.

DNA methylation plays a significant role in mediating gene expression. Less is known about how this epigenetic mark is distributed throughout the genome, and in particular why DNA methyltransferases (DNMTs), which are not sequence-specific, "avoid" certain CpG islands. The demethylating agent 5-aza-cytidine and analogs have been used for epigenetic research and received approval by the U.S. Food and Drug Administration for the treatment of all subtypes of myelodysplastic syndrome (MDS).

Currently, the two most prominent, approved demethylating agents for the treatment of myelodysplastic syndrome are azacitidine (or 5-azacytidine, sold as Vidaza) and decitabine (or 5-aza-2'-deoxycytidine, sold as Dacogen). These agents are incorporated into genomic DNA and inhibit DNMT by covalent binding. Cytotoxic effects have been associated with global incorporation of these agents into DNA and, thus, limit their clinical application. Although non-nucleoside inhibitors of DNA methylation possess less potential side effects, these inhibitors are generally less efficient than their nucleoside analogues and still cause global demethylation. Global, non-specific demethylation can lead to increased tumorogenicity because demethylation likely decreases expression of tumor suppressor genes as well as prometastatic genes.

Therapy of diseases, including various cancers, can be impaired by non-specific demethylating agents. Thus, new strategies for gene-specific delivery of agents to reduce methylation of DNA are desired.

SUMMARY OF THE INVENTION

We have now developed chimeric RNA oligonucleotides (CROs) capable of targeting specific genes and reducing DNA methylation of a gene by a DNA methyltransferase. These CROs can be used to treat any condition having aberrant hypermethylation, including cancer.

In a first aspect, the invention features a synthesized RNA oligonucleotide for reducing DNA methylation of a gene by a DNA methyltransferase (DNMT), where the oligonucleotide includes a sequence of about 15 to about 30 nucleotides (e.g., 15-20 nucleotides, 15-25 nucleotides, 15-30 nucleotides, 15-35 nucleotides, 16-20 nucleotides, 16-25 nucleotides, 16-30 nucleotides, 16-35 nucleotides, 17-20 nucleotides, 17-25 nucleotides, 17-30 nucleotides, 17-35 nucleotides, 18-20 nucleotides, 18-25 nucleotides, 18-30 nucleotides, or 18-35 nucleotides) having at least 80% complementarity (e.g., at least being 85%, 90%, 95%, 97%, 99%, and 100% complementarity) to a portion of an extra-coding RNA of the gene, and where the synthesized RNA binds to the extra-coding RNA to form a complex and the complex binds to a DNMT to reduce DNA methylation of the gene. In further embodiments, the synthesized RNA oligonucleotide is covalently or non-covalently linked to a targeting moiety, where the targeting moiety is a polypeptide, polypeptide derivative, or peptidomimetic that is capable of transport across into a particular cell type (e.g., a cell-penetrating peptide, such as a polycationic or an amphipathic peptide).

In some embodiments, the invention features a synthesized RNA oligonucleotide for reducing DNA methylation of a gene by a DNA methyltransferase (DNMT), where the oligonucleotide consists of a sequence of about 15 to about 30 nucleotides (e.g., 15-20 nucleotides, 15-25 nucleotides, 15-30 nucleotides, 15-35 nucleotides, 16-20 nucleotides, 16-25 nucleotides, 16-30 nucleotides, 16-35 nucleotides, 17-20 nucleotides, 17-25 nucleotides, 17-30 nucleotides, 17-35 nucleotides, 18-20 nucleotides, 18-25 nucleotides, 18-30 nucleotides, or 18-35 nucleotides) having at least 80% complementarity (e.g., at least being 85%, 90%, 95%, 97%, 99%, and 100% complementarity) to a portion of an extra-coding RNA of the gene, and where the synthesized RNA binds to the extra-coding RNA to form a complex and the complex binds to a DNMT to reduce DNA methylation of the gene. In further embodiments, In some embodiments, the invention features a synthesized RNA oligonucleotide for reducing DNA methylation of a gene by a DNA methyltransferase (DNMT), where the oligonucleotide consists of a sequence of about 15 to about 30 nucleotides (e.g., 15-20 nucleotides, 15-25 nucleotides, 15-30 nucleotides, 15-35 nucleotides, 16-20 nucleotides, 16-25 nucleotides, 16-30 nucleotides, 16-35 nucleotides, 17-20 nucleotides, 17-25 nucleotides, 17-30 nucleotides, 17-35 nucleotides, 18-20 nucleotides, 18-25 nucleotides, 18-30 nucleotides, or 18-35 nucleotides) having at least 80% complementarity (e.g., at least being 85%, 90%, 95%, 97%, 99%, and 100% complementarity) to an extra-coding RNA of the gene that is covalently or non-covalently linked to a targeting moiety (e.g., as described herein).

In a second aspect, the invention features a pharmaceutical composition including any synthesized RNA oligonucleotide described herein and a pharmaceutically acceptable excipient. In some embodiments of this aspect, the composition further includes a histone deacetylase inhibitor (e.g., a hydroxamic acid, such as trichostatin A (TSA), vorinostat (SAHA), belinostat (PXD101), ((E)-N-hydroxy-3-[4-[[2-hydroxyethyl-[2-(1H-indol-3-yl)ethyl]amino]methyl]phenyl]prop-2-enamide (LAQ824), panobinostat (LBH589), suberoylanilide hydroxamic acid (SAHA), oxamflatin, scriptaid, suberic bishydroxamic acid (SBHA), m-carboxy-cinnamic acid bishydroxamic acid (CBHA), and pyroxamide); a cyclic peptide, such as trapoxin A, apidicin, TPX-HA, and depsipeptide (FR901228)); a benzamide, such as entinostat (MS-275), N-acetyldinaline (CI994), and mocetinostat (MGCD0103); an electrophilic ketone, such as trifluoromethyl ketones or alpha-ketoamides, see Frey et al., Bioorg. Med. Chem. Lett. 12:3443-3447, 2002, and U.S. Pat. No. 6,511,990, incorporated herein by reference); and a fatty acid, such as valproic acid, arginine butyrate, butyric acid, and phenylbutyrate).

In a third aspect, the invention features a method of treating or prophylactically treating a subject having cancer, the method including administering to the subject any synthesized RNA oligonucleotide described herein or any pharmaceutical composition described herein in an amount sufficient to treat the cancer. In some embodiments, the cancer is selected from the group of a myelodysplastic syndrome (e.g., refractory anemia, refractory anemia with ringed sideroblasts, refractory anemia with excess blasts, refractory anemia with excess blasts in transformation, refractory cytopenia with multilineage dysplasia, myelodysplastic syndrome associated with an isolated del(5q) chromosome abnormality, and a myeloproliferative neoplasm), leukemia (e.g., acute myeloid leukemia), head and neck cancer, liver cancer (e.g., hepatoma and hepatocellular carcinoma), lung cancer (e.g., adenocarcinoma, small cell lung cancer, and non-small cell lung cancer), prostate cancer (e.g., adenocarcinoma), skin cancer (e.g., squamous cell carcinoma), retinoblastoma, glioblastoma, breast cancer, thyroid cancer, ovarian cancer, pancreatic cancer, brain cancer, kidney cancer, colon cancer, endometrial cancer, gastric cancer, multiple myeloma, and lymphoma (e.g., T-cell lymphoma).

In a fourth aspect, the invention features a method of treating or prophylactically treating a subject having a genetic disorder, the method including administering to the subject any synthesized RNA oligonucleotide described herein or any pharmaceutical composition described herein in an amount sufficient to treat the genetic disorder. In some embodiments, the genetic disorder is an imprinting disorder (e.g., Beckwith-Wiedemann Syndrome (BWS), Prader-Willi Syndrome (PWS), Angelman Syndrome (AS), Albright hereditary osteodystrophy (AHO), pseudohypoparathyroidism type 1A (PHP-IA), and pseudohypoparathyroidism type 1B (PHP-IB)); a disorder associated with loss of imprinting (LOI) (e.g., LOI in IGF2/H19 for Wilms' tumor); and a repeat instability disease (e.g., Fragile X syndrome and myotonic dystrophy).

In a fifth aspect, the invention features a method of preparing a synthesized RNA oligonucleotide for reducing DNA methylation of a gene by a DNA methyltransferase (DNMT), the method including preparing a sequence of about 15 to about 30 nucleotides (e.g., 15-20 nucleotides, 15-25 nucleotides, 15-30 nucleotides, 15-35 nucleotides, 16-20 nucleotides, 16-25 nucleotides, 16-30 nucleotides, 16-35 nucleotides, 17-20 nucleotides, 17-25 nucleotides, 17-30 nucleotides, 17-35 nucleotides, 18-20 nucleotides, 18-25 nucleotides, 18-30 nucleotides, or 18-35 nucleotides) having at least 80% complementarity (e.g., at least being 85%, 90%, 95%, 97%, 99%, and 100% complementarity) to an extra-coding RNA of the gene. In a further embodiment of this aspect, the method further includes incorporating one or more modified nucleotides into the sequence of about 15 to about 30 nucleotides.

In a sixth aspect, the invention features a method of identifying a RNA oligonucleotide for reducing DNA methylation of a gene by inactivating a DNA methyltransferase (DNMT), the method including: analyzing the sequence of one or more extra-coding RNAs of the gene; identifying a nucleotide sequence having at least 80% complementarity (e.g., at least being 85%, 90%, 95%, 97%, 99%, and 100% complementarity) to the extra-coding RNA; and determining one or more binding sites between the nucleotide sequence having at least 80% complementarity with the extra-coding RNA and/or the DNMT (e.g., by using a RNA electrophoretic mobility shift assay), thereby identifying the RNA oligonucleotide for reducing DNA methylation (e.g., by at least 10% or any percentage described herein). In a further embodiment of this aspect, the method includes sequencing one or more extra-coding RNAs of the gene. In another further embodiment of this aspect, the method includes synthesizing the nucleotide sequence having at least 80% complementarity. In yet another further embodiment, the method includes contacting the nucleotide sequence having at least 80% complementarity with one or more extra-coding RNAs and/or DNMTs. In another embodiment, the method includes the nucleotide sequence having one or more modified nucleotides. In any of these embodiments, the method includes reducing DNA methylation of a gene by inactivating and sequestering a DNMT. In another embodiment, the CROs contain gene-specific sequences that can be designed having a sequence that is at least 80% (e.g., at least 85%, 90%, 95%, 96%, 97%, 98%, 99% or more) complementary to a region spanning the promoter, the coding part of the gene, and/or the 3'-downstream part (e.g., −2 kilobases and/or +2 kilobases from the transcriptional start site (TSS) or the transcriptional end site (TES) of the genes, respectively). In a further embodiment of this aspect, the genes are those contained in cluster C and any described herein.

In a seventh aspect, the invention features a method of diagnosing a subject for treatment with a synthesized RNA oligonucleotide for reducing DNA methylation of a gene by a DNA methyltransferase (DNMT), the method including: determining the subject as having a cancer or a genetic disorder (e.g., any cancer or disorder described herein) related to the gene (e.g., any gene described herein, such as from cluster C), analyzing the sequence of one or more extra-coding RNAs of the gene, identifying an RNA oligonucleotide sequence having at least 80% complementarity (e.g., at least being 85%, 90%, 95%, 97%, 99%, and 100% complementarity) to the extra-coding RNA, synthesizing the RNA oligonucleotide, and administering the RNA oligonucleotide for reducing the methylation (e.g., by at least 10% or any percentage described herein).

In particular embodiments of any of the above aspects, the extra-coding RNA is a transcribed RNA corresponding to a coding region, a non-coding region, or both coding and non-coding regions, or is a fragment thereof. In particular embodiments, the extra-coding RNA is a transcribed RNA corresponding to a non-coding region or a fragment of a non-coding region. In other embodiments, the extra-coding RNA is a transcribed RNA corresponding to both a coding region and a non-coding region or to both a fragment of a coding region and a fragment of a non-coding region.

In certain embodiments of any of the above aspects, the RNA oligonucleotide includes one or more modified nucleotides selected from 5-azacytidine, 5-aza-5,6-dihydrocytosine, 5-aza-2'-deoxycytidine, beta-L-5-azacytidine, 2'-deoxy-beta-L-5-azacytidine, 2'-deoxy-N4-[2-(4-nitrophenyl)ethoxycarbonyl]-5-azacytidine, 5-fluorocytidine, 1-β-D-arabinofuranosil-5-azacytosine, and 1-β-D-ribofuranosyl-2(1H)-pyrimidinone, and analogs thereof (e.g., analogs having one of the following substitutions for the hydrogen of the 4-amino group of the cytosine ring: methyl, ethyl, 9-fluorenylmethyl, 9-(2-sulfo)fluorenylmethyl, 9-(2,7-dibromo)fluorenylmethyl, 17-tetrabenzo[a,c,g,i]fluorenylmethyl, 2-chloro-3-indenylmethyl, benz[f]inden-3-ylmethyl, 2,7-di-tert-[9-(10,10-dioxo-10,10,10,10-tetrahydrothioxanthyl)methyl, 1,1-dioxobenzo[b]thiophene-2-ylmethyl, 2,2,2-trichloroethyl, 2-trimethylsilylethyl, 2-phenylethyl, 1-(1-adamantyl)-1-methylethyl, 2-chloroethyl, 1,1-dimethyl-2-haloethyl, 1,1-dimethyl-2,2-dibromethyl, 1,1-dimethyl-2,2,2-trichloroethyl, 1-methyl-1-(4-biphenylyl)ethyl, 1-(3,5-di-tert-butylphenyl)-1-methylethyl, 2-(2'- and 4'-pyridyl)ethyl, 2,2-bis(4'-nitrophenyl)ethyl, N-(2-pivaloylamino)-1,1-dimethylethyl, 2-[(2-nitrophenyl)dithio]-1-phenylethyl, 2-(N,N-dicyclohexylcarboxamido)ethyl, t-butyl, 1-adamantyl, 2-adamantyl, vinyl, allyl, 1-isopropylallyl, cinnamyl, 4-nitrocinnamyl, 3-(3'-pyridyl)prop-2-enyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl, 2-methylthioethyl, 2-methylsulfonylethyl, 2-p-toluenesulfonyl)ethyl, [2-(1,3-dithianyl)]methyl, 4-methylthiophenyl, 2,4-dimethylthiophenyl, 2-phosphonioethyl, 1-methyl-1-(triphenylphosphonio)ethyl, 1,1-dimethyl-2-cyanoethyl, 2-dansylethyl, 4-phenylacetoxybenzyl, 4-azidobenzyl, 4-azidomethoxybenzyl, m-chloro-p-acyloxybenzyl, p-(dihydroxyboryl)benzyl, 5-benzisoxazolylmethyl, 2-(trifluoroethyl)-6-chromonylmethyl, m-nitrophenyl, 3,5-dimethoxybenzyl, 1-methyl-1-(3,5-dimethoxyphenyl)ethyl, α-methylnitropiperonyl, o-nitrophenyl, 3,4-dimethoxy-6-nitrobenzyl, phenyl(o-nitrophenyl)ethyl, 2-(2-nitrophenyl)ethyl, 6-nitroveratryl, 4-methoxyphenacyl, 3',5'-dimethoxybenzoin, t-amyl, S-benzylthio, butynyl, p-cyanobenzyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethycarboxamido)propyl, 1,1-dimethylpropynyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(p-phenylazophenyl)ethyl, 1-methyl-1-phenylethyl, 1-methyl-1-(4'-pyridyl)ethyl, phenyl, p-(phenylazo)benzyl, 2,4,6-tri-t-butylphenyl, 4-(trimethylammonium)benzyl, 2,4,6-trimethylbenzyl, a urea (e.g., a urea with phenothiazinyl-(10)-carbonyl, N'-p-toluenesulfonylaminocarbonyl, and N'-phenylaminothiocarbonyl), and an amide (e.g., formamide, acetamide, phenoxyacetamide, trichloroacetamide, trifluoroacetamide, phenyacetamide, 3-phenylpropamide, pent-4-enamide, o-nitrophenylacetamide, o-nitrophenoxyacetamide, 3-(o-nitrophenyl)propanamide, 2-methyl-2-(o-nitrophenoxy)propanamide, 3-methyl-3-nitrobutanamide, o-nitrocinnamide, 3-(4-t-butyl-2,6-dinitrophenyl)-2,2-dimethylpropanamide, o-(benzoyloxymethyl)benzamide, 2-[(t-butyldiphenylsiloxy)methyl)methyl]benzamide, 3-(3',6'-dioxo-2',4',5'-trimethylcyclohexa-1',4'-diene)-3,3-dimethylpropionamide, o-hydroxy-trans-cinnamide, acetoacetamide, p-toluenesulfonamide, and benzesulfonamide); or those having one of the following substitutions for the 4-amino group of the cytosine ring: 4-O-methoxy and 4-S-methylsulfanyl). In further embodiments, the modified nucleotide is a cytidine analog further conjugated to a guanosine nucleotide (e.g., 5-aza-2'-deoxycytidine-phosphodiester linkage-guanosine, 5-aza-2'-deoxycytidine-phosphodiester linkage-2'-deoxyguanosine, guanosine-phosphodiester linkage-5-aza-2'-deoxycytidine, or 2'-deoxy-guanosine-phosphodiester linkage-5-aza-2'-deoxycytidine). In other embodiments, the RNA oligonucleotide includes one or more modified nucleotides selected from cytarabine, fludarabine, gemcitabine, cladribine, clofarabine, 5-fluorouracil, azathioprine, floxuridine, mercaptopurine, thioguanine, pentostatin, and cladribine, or an analog thereof. In yet further embodiments, the modified nucleotide is 5-azacytidine or 5-aza-2'-deoxycytidine.

In other embodiments of any of the above aspects, the RNA oligonucleotide includes a therapeutic agent selected from a demethylating agent (e.g., 5-azacytidine (azacitidine), 5-aza-2'-deoxycytidine (decitabine), any cytidine analog described herein, and any other demethylating agent described herein), a DNA and/or RNA polymerase inhibitor (e.g., cytarabine, fludarabine, gemcitabine, cladribine, and clofarabine), a thymidylate synthase inhibitor (e.g., 5-fluorouracil, floxuridine, capecitabine, tegafur, and carmofur), an immunosuppressant (e.g., azathioprine), an adenosine deaminase inhibitor (e.g., pentostatin), a thiopurine (e.g., thioguanine and mercaptopurine), or a label (e.g., an isotope, such as a positron emitting isotope; a radioimaging agent or a radiolabel; a fluorescent label, such as green fluorescent protein (GFP), fluorescein, and rhodamine; a nuclear magnetic resonance active label; a luminescent label; a chromophore label; a chemiluminescence label, such as luciferase and β-galactosidase; an enzymatic label, such as peroxidase and phosphatase; a reporter molecule, such as biotin or a histamine tag; and an antibody or an antibody fragment).

In other embodiments of any of the above aspects, the gene is C/EBPa (CCAAT enhancer binding protein alpha); SPE (spleen focus forming virus (SFFV) proviral integration oncogene spi1); RXRA (retinoid X receptor, alpha); RARB (retinoic acid receptor, beta); RB1 (retinoblastoma 1); CDKN2A (cyclin-dependent kinase inhibitor 2A); CDH1 (cadherin 1, type 1, E-cadherin); CDH13 (cadherin 13, H-cadherin); TIMP3 (TIMP metallopeptidase inhibitor 3); VHL (von Hippel-Lindau tumor suppressor); MLH1 (mutL homolog 1, colon cancer, nonpolyposis type 2); MGMT (O-6-methylguanine-DNA methyltransferase); BRCA1 (breast cancer 1, early onset); GSTP1 (glutathione S-transferase pi 1); HLTF (helicase-like transcription factor); RASSF1 (Ras association (RalGDS/AF-6) domain family member 1); SOCS1 (suppressor of cytokine signaling 1); ESR1 (estrogen receptor 1); or DAPK1 (death-associated protein kinase 1). In some embodiments, the gene is C/EBPa and the extra-coding RNA of C/EBPa is SEQ ID NO:1 or SEQ ID NO:8, or a fragment thereof. In other embodiments, the gene is SPI1 and the extra-coding RNA of SPI1 is SEQ ID NO:2, SEQ ID NO:3, SEQ ID NO:4, or SEQ ID NO:5, or a fragment thereof. In yet other embodiments, the gene is RXRA and the extra-coding RNA of RXRA is SEQ ID NO:6 or SEQ ID NO:7, or a fragment thereof. In some embodiments, the gene is RARB and the extra-coding RNA of RARB is SEQ ID NO:9, or a fragment thereof. In other embodiments, the extra-coding RNA of the gene is the promoter region of the gene. In further embodiments, the extra-coding RNA is the promoter region of the gene selected from C/EBPa, SPI1, RXRA, and RARB.

In other embodiments of any of the above aspects, the genes are found in cluster C as described herein. Some of those genes belong to particular Gene Ontology (GO) categories (www.geneontology.org and The Gene Ontology Consortium, "Gene ontology: tool for the unification of biology," Nat. Genet. 25(1):25-29 (2009)). Exemplary non-limiting GO categories include genes related to conversion of one or more primary RNA transcripts into one or more mature RNA molecules (GO:0006396, RNA processing); genes related to biochemical and morphological phases that occur during successive cell or nuclear replication events (GO:0007049, cell cycle), genes related to chemical reactions and pathways involving mRNA (GO:0016071, mRNA metabolic process), genes related to assembly, arrangement, or disassembly of chromosomes (GO:0051276, chromosome organization), genes related to splicing and joining primary RNA transcript to form mature form of the RNA (GO:0008380, RNA splicing), and any described herein.

In particular embodiments of any of the above aspects, the oligonucleotide is not double-stranded.

In some embodiments of any of the above aspects, the DNMT is selected from the group consisting of DNMT1, DNMT2, DNMT3a, DNMT3b, and DNMT3L. In further embodiments, the DNMT is DNMT1.

DEFINITIONS

By "chimeric RNA oligonucleotide" or "CRO" is meant an RNA oligonucleotide capable of reducing the activity of DNA methyltransferase and of selectively or specifically hybridizing to a target sequence within a gene locus.

By "complementarity" is meant an oligonucleotide able to form one or more hydrogen bonds with another oligonucleotide (e.g., a RNA) by either traditional Watson-Crick (e.g. G with C, A with T, or A with U) or other non-traditional types (e.g., diaminopurine with T, 5-methyl C with G, 2-thiothymidine with A, inosine with C, pseudoisocytosine with G, etc.). In reference to the oligonucleotide of the present invention, the binding site (or binding energy) for a nucleotide with its target or complementary sequence is sufficient to allow the relevant function of the nucleotide to proceed, e.g., targeting of the RNA, binding to DNMT, or triple helix formation. Determination of a binding site (or binding energy) for a nucleotide is well known in the art (see, e.g., Turner et al., Cold Spring Harbor Symp. Quant. Biol. 52:123-133, 1987; Frier et al., Proc. Natl. Acad. Sci. USA 83:9373-9377, 1986; and Turner et al., J. Am. Chem. Soc. 109:3783-3785, 1987). A percent complementarity indicates the percentage of contiguous residues in a nucleotide that can form hydrogen bonds (e.g., Watson-Crick base pairing) with a second nucleotide (e.g., being 50%, 55%, 60%, 65%, 70%, 75%, 80%, 85%, 90%, 95%, 97%, 99%, and 100% complementary), optionally determined under stringent conditions.

By "complex binds to a DNA methyltransferase" is meant an interaction between a CRO-extra-coding RNA complex and a DNA methyltransferase with a dissociation constant (Kd) measured in the range of between 0.01 µM to 0.10 µM (e.g., 0.01, 0.02, 0.03, 0.05, 0.08, 0.09, and 0.1 µM).

By "cytidine analog" is meant a modified nucleotide having a cytosine base or a modified cytosine base.

By "demethylating agent" is meant an agent that leads to decreased methylation of DNA by directly or indirectly inactivating a DNA methyltransferase.

By "DNA methyltransferase" or "DNMT" is meant an enzyme that methylates the C-5 carbon of cytosines in DNA. Exemplary DNMTs include DNMT1, DNMT2, DNMT3a, DNMT3b, and DNMT3L.

By "extra-coding RNA" or "ecRNA" is meant transcribed pre-mRNA including both coding and non-coding regions or only non-coding regions. Extra-coding RNA regions and fragments thereof may include those that can form secondary structures with CROs as predicted by RNA secondary structure prediction programs known in the art (e.g., CentroidFold, Mfold, RNAfold, RNAstructure, and CONTRAfold). Extra-coding RNA regions and fragments thereof may also include those that modulate methylation patterns of genes associated with the extra-coding RNA region. In some embodiments, the ecRNA only includes one or more contiguous, non-coding regions of a gene.

By "fragment" is meant a portion of a full-length amino acid or nucleic acid sequence (e.g., any sequence described herein). Fragments may include at least 4, 5, 6, 8, 10, 11, 12, 14, 15, 16, 17, 18, 20, 25, 30, 35, 40, 45, or 50 contiguous amino acids or nucleic acids of the full length sequence. A fragment may retain at least one of the biological activities of the full length protein or nucleic acid.

By "inactivating a DNA methyltransferase" is meant a RNA oligonucleotide that reduces the methylating activity of DNA methyltransferase by at least 10% (e.g., at least 15%, 20%, 25%, 30%, 35%, 40%, 45%, 50%, 55%, 60%, 65%, 70%, 75%, 80%, 85%, 90%, 95%, or even 99%) compared to a control lacking the RNA oligonucleotide.

By "modified nucleotide" is meant a nucleotide having a modification to the chemical structure of one or more of the base, sugar, and backbone, including the phosphate linker.

By "reduced DNA methylation" is meant reducing the methylating activity of DNA methyltransferase by at least 10% (e.g., at least 15%, 20%, 25%, 30%, 35%, 40%, 45%, 50%, 55%, 60%, 65%, 70%, 75%, 80%, 85%, 90%, 95%, or even 99%), compared to a control lacking the RNA oligonucleotide. Non-limiting methods for determining reduced DNA methylation are described herein (e.g., in Example 4).

By "stringent conditions" is meant conditions under which a RNA oligonucleotide will selectively or specifically hybridize to its target sequence (i.e., an extra-coding RNA), typically in a complex mixture of nucleic acids, but to no other sequences. Stringent conditions are sequence-dependent and length-dependent. Generally, stringent conditions are selected to be about 5° C. to about 25° C. lower than the thermal melting point ($T_m$) for the specific sequence at a defined ionic strength pH. Stringent conditions may also include destabilizing agents, such as formamide. For selective or specific hybridization, a positive signal is at least two times background, preferably 10 times background hybridization. Exemplary stringent conditions include: 50% formamide, 4×SSC, and 1% SDS, incubating at 42° C.; and 4×SSC, 1% SDS, incubating at 65° C., with wash in 0.2×SSC, and 0.1% SDS at 65° C. Hybridization techniques are generally described in Nucleic Acid Hybridization, A Practical Approach (eds. B. D. Hames and S. J. Higgins, IRL Press, 1985); Tijssen, "Overview of principles of hybridization and the strategy of nucleic acid assays" in *Laboratory Techniques in Biochemistry and Molecular Biology: Hybridization with Nucleic Probes* (ed. P. C. van der Vliet, Elsevier Science Publishers B.V., 1993); PCR Protocols, A Guide to Methods and Applications (eds. M. A. Innis et al., Academic Press, Inc., New York, 1990); Gall and Pardue, Proc. Natl. Acad. Sci., USA 63:378-383, 1969; and John et al., Nature 223:582-587, 1969.

By "substantially identical" is meant an oligonucleotide exhibiting at least 30%, 35%, 40%, 45%, 50%, 55%, 60%, 65%, 70%, 75%, 80%, 85%, 90%, 95%, or even 99% identity to a reference nucleotide sequence. For polypeptides, the length of comparison sequences will generally be at least 4 (e.g., at least 5, 6, 7, 8, 9, 10, 11, 12, 13, 14, 15, 16, 17, 18, 19, 20, 25, 50, or 100) amino acids. For oligonucleotides, the length of comparison sequences will generally be at least 5 nucleotides (e.g., 5, 6, 7, 8, 9, 10, 11, 12, 13, 14, 15, 16, 17, 18, 19, 20, 21, 22, 23, 24, 25, 26, 27, 28, 29, or 30 nucleotides). It is to be understood herein that gaps may be found between the nucleotide of sequences that are identical or similar to nucleotides of the original oligonucleotide. The gaps may include no nucleotides or one or more nucleotides that are not identical or similar to the original oligonucleotide. Percent identity may be determined, for example, with an algorithm GAP, BESTFIT, or FASTA in the Wisconsin Genetics Software Package Release 7.0, using default gap weights.

By "subject" is meant a human or non-human animal (e.g., a mammal).

By "treating" a disease, disorder, or condition in a subject is meant reducing at least one symptom of the disease, disorder, or condition by administrating a conjugate or therapeutic polypeptide to the subject.

By "prophylactically treating" a disease, disorder, or condition in a subject is meant reducing the frequency of occurrence or severity of (e.g., preventing) a disease, disorder or condition by administering to the subject a conjugate or therapeutic polypeptide to the subject prior to the appearance of a disease symptom or symptoms.

Other features and advantages of the invention will be apparent from the following Detailed Description, the drawings, and the claims.

BRIEF DESCRIPTION OF THE DRAWINGS

FIGS. 1A-1L show the characterization of an extra-coding RNA of the C/EBPa gene. FIG. 1A is a diagram of coding (gray arrow) and extra-coding (arrow labeled with "~5 kb") RNAs. The white rectangle indicates the position of the probe used in the RNA electrophoretic mobility shift assays (REMSAs). The black star indicates the C/EBPa mRNA probe located in the 3'UTR region, and the white star indicates the extra-coding probe located after the polyA signal outside the coding sequence. FIG. 1B is a Northern blot hybridization analysis of coding RNAs (black star), extra-coding RNAs (white star), and loading control (EtBr) using the mRNA probe and extra-coding probe in HL-60, U937, Jurkat, and K562 cell lines. FIG. 1C show graphs for levels of coding (left) and extra-coding (right) C/EBPa transcripts in cellular fractions from HL-60 cell lines. FIGS. 1D-1E show relative levels of the transcripts in total and nuclear fractions, where the ratio between mRNA and ecRNA levels were 30:1 and 2:1 in total and nuclear fractions, respectively. FIG. 1F shows that DRB treatment did not reduce ecRNA levels upon release of cells from double thymidine block. FIG. 1G shows that treatment with the Pol III inhibitor ML-60218 significantly reduced levels of ecRNA and Pol III-transcribed 5S rRNA and only moderately affected C/EBPa mRNA (P=n.s.). FIGS. 1C-1G show results of qRT PCR assays. Statistical analysis performed by paired T-test (*P<0.05; P<001; *P<0.001); and all error bars are means±s.d (n=3). FIG. 1H is a series of Northern blots of non-coding (nc) C/EBPa transcripts performed on nuclear RNA fractions of three different cell lines (left panel). The two middle panels demonstrate enrichment of non-coding C/EBPa transcripts in nuclear polyA(−) fraction; the right panel illustrates the extent of polyA(−) fraction purity. FIG. 1I are results from primer extension experiments performed on total cellular and cellular polyA(−) RNAs of HL-60 cell line as described in the experimental procedures. The AL16 oligonucleotide is located in the coding region of C/EBPa gene. Primer extension revealed a ~4 kb band in the polyA(−) fraction, marking the TSS for non-coding transcript at ~2 kb upstream to the mRNA TSS. FIG. 1J are sequences used for mapping non-coding C/EBPa transcripts by 5' (SEQ ID NO:58), 3' (SEQ ID NO:59) RACE in two cell lines, HL-60 and U937. R4, R6, R8, and AL21, A123, AL25 are primers used in RACE. Also provided are the 5' and 3' ends of non-coding and coding transcripts in both cell lines. FIG. 1K show results from double thymidine block of HL-60 cells. Treatment with thymidine (2.5 mM) arrested the cells in G1/S phase border. FACS analysis shows synchronization after the treatment. FIG. 1L shows the levels of coding and ecRNA upon release from double thymidine block. Induction of ecRNA preceded and surpassed expression of C/EBPa mRNA.

FIG. 2A is a graph showing the effect of shRNAs that target extra-coding RNAs on the levels of extra-coding RNA (left) and of mRNA expression (right). The shRNAs are designed against the sequence after the polyA signal. FIG. 2B is a chart showing the effect of shRNAs that target extra-coding RNAs on promoter methylation. Methylation data from bisulfate sequencing was analyzed with BIQ Analyzer software (Aggregated Representation of Methylation Data). The white bars represent methylated states, the black bars represent unmethylated states of each CpG dinucleotide within the sequencing reads, and changes from black bars (as shown in lane labeled "Scrambled" in FIG. 2B) to white bars (as shown in lanes labeled "sh1," "sh2," and "sh3" in FIG. 2B) indicate increase in methylation states of corresponding CpG dinucleotides. FIG. 2C is a graph showing quantification of the results shown in FIG. 2B.

FIGS. 4A-4F show that DNMT1 binds to folded RNAs with high affinity comparable to that of DNA. FIG. 4A provides an exemplary RNA oligonucleotide (SEQ ID NO:60) corresponding to the 5' end of C/EBPa extra-coding RNA. FIG. 4B provides stem-loop-like folding of the RNA oligonucleotide (SEQ ID NO:60). FIG. 4C provides an exemplary double-stranded DNA oligonucleotide corresponding to the 5' sequence of the RNA oligonucleotide (SEQ ID NO:61). FIG. 4D shows an analysis of a RNA electrophoretic mobility shift assay (REMSA) for RNA and DNA. Provided are data for free probes (lanes 1 and 5); probes with DNMT1, without polydIdC (lanes 2 and 6); and probes with DNMT1 having increasing amounts of competitor, polydIdC (lanes 3, 4, 7, and 8). The bottom panel demonstrates uniformity in probe loading. FIG. 4E shows that double-stranded RNA (dsRNA) molecules bind to DNMT1 and single-stranded RNA (ssRNA) of the same primary structure have low to zero capacity for DNMT1. FIG. 4F shows an analysis of a REMSA with RNAse T3 digested transcripts corresponding to the 5' regions of the C/EBPa extra-coding RNAs and the luciferase gene, showing similar binding affinity of DNMT1 to dsRNAs from different sources.

FIG. 5A are schematics showing (i) a hemimethylated DNA segment with an integrated 17 promoter; (ii) an in vitro transcription assay using T7 polymerase and nucleotide triphosphates (NTPs); (iii) a parallel in vitro transcription and methylation assay using T7 polymerase, NTPs, and DNMT1; and (iv) an in vitro methylation assay using NTPs and DNMT1. FIG. 5B shows a combined bisulfite restriction analysis (COBRA) assay of methylation patterns acquired using the assays provided in FIG. 5A(ii)-(iv). The black arrow indicates the presence of digestion products and shows that DNMT1 activity is present in the absence of transcription.

FIG. 6A is a schematic showing high-expressing RNAs that sequesters DNMT1 and interferes with DNA methylation of the corresponding region (left). In absence of transcription (right), DNMT1 methylates the targeted region. FIG. 6B is a schematic showing a proposed, non-limiting mechanism of DNMT1 sequestration by a double-stranded chimeric RNA oligonucleotide. FIG. 6C is a schematic showing a proposed non-limiting mechanism of DNMT1 sequestration through forming a double-stranded complex between natural RNA and a single-stranded chimeric RNA oligonucleotide. FIG. 6D depicts a proposed, non-limiting mechanism of DNMT1 sequestration through triplex structure formation (e.g., H form) between genomic DNA and a single-stranded chimeric RNA oligonucleotide. Aza indicates 5-aza-2'-deoxycytidine or an analog thereof.

FIGS. 7A-7D show results from an exemplary screen for extra-coding RNA having "target site specificity." FIG. 7A depicts the position of two chosen regions within C/EBPa extra-coding RNA: R1 and R2. BLAST analyses are provided for R2 (FIG. 7B) and R1 (FIG. 7C). FIG. 7D is a Northern blot hybridization analysis of probes corresponding to regions R1 and R2, where total RNAs was extracted from cell lines that express C/EBPa (HL-60 and U937 cell lines) and from cell lines that do not express C/EBPa (HEK 293 and K562 cell lines).

FIG. 8 provides an exemplary sequence of the 3'-end of the C/EBPa extra-coding RNA (SEQ ID NO:1).

FIG. 9 provides exemplary extra-coding RNAs of four different locations of the spleen focus forming virus proviral integration oncogene spi1 (SPI1, *Homo sapiens*) gene locus, including bases 47356552-47356358 (SEQ ID NO:2), 47340202-47339789 (SEQ ID NO:3), 47342950-47342689 (SEQ ID NO:4), and 47340198-47339789 (SEQ ID NO:5) of *Homo sapiens* chromosome 11, GRCh37.p2 primary reference assembly (NCBI Ref. Seq. NT_009237.18).

FIG. 10 provides exemplary extra-coding RNAs of two different locations of the retinoid X receptor alpha (RXRA, *Homo sapiens*) gene locus, including bases 126630-127130 (SEQ ID NO:6) and 127305-127805 (SEQ ID NO:7) of *Homo sapiens* chromosome 9, GRCh37.p2 primary reference assembly (NCBI Ref. Seq. NT_019501.13).

FIGS. 11A and 11B provides an exemplary sequence of C/EBPa extra-coding RNA (SEQ ID NO:8).

FIG. 12 provides an exemplary sequence of retinoic acid receptor beta (RARB, *Homo sapiens*) extra-coding RNA (SEQ ID NO:9), including bases 25407956-25410445 of *Homo sapiens* chromosome 3, GRCh37.p2 primary reference assembly (NCBI Ref. Seq. NT_022517.18).

FIG. 13A is a diagram indicating the position of target sequences for shRNA constructs (sh1-3; vertical arrows); the 1057 bp fragment derived from the ecRNA employed for overexpression (R1; double-headed arrow); and regions analyzed for changes in DNA methylation (distal promoter; coding sequence, CDS; and 3'UTR; white double-headed arrows). FIG. 13B shows the effect of ecRNA-targeting shRNAs on C/EBPa transcript levels in U937 cells. FIG. 13C shows the effect of ecRNA-targeting shRNAs on methylation of the C/EBPa promoter using bisulfite sequencing. The lollipop representation is used to show methylation patterns, where black dots indicate methylated positions and white dots indicate unmethylated positions. FIG. 13D shows DNA methylation changes as the ratios of methylated to unmethylated CpGs in all clones analyzed per each construct. FIG. 13E shows the effect of ecRNA upregulation on levels of C/EBPa mRNA. The unrelated region (UR) is a 705 bp fragment located ~45 kb downstream to the C/EBPa gene. FIG. 13F shows the effect of ecRNA upregulation on methylation of the C/EBPa locus, where lollipop representations (left) and DNA methylation changes (right) are provided. FIGS. 13G-13I show comparisons of DNA methylation changes imposed by ecRNA overexpression and 5-Aza-CR treatment by MassARRAY analysis. FIG. 13G is a diagram showing the position of MassARRAY target regions; C/EBPa and C/EBPg genes; and CpG islands. FIG. 13H is a heatmap representing the methylation level of individual CpGs for overexpression samples (UR, R1); two untreated control cell lines (K562, HL-60); and mock 5-Aza-CR-treated cells; below are snapshots of regions corresponding to C/EBPa and C/EBPg genes. FIG. 13I shows methylation changes (Methylation Delta) induced by ectopic ecRNA expression that are significant only within C/EBPa locus. The region +6 kb includes the R1 fragment and was excluded from the statistical analysis. FIGS. 13J-13K are comparative analyses of C/EBPa and C/EBPg expression and methylation changes following 5-Aza-CR treatment and ecRNA overexpression in K562 cells, where lollipop representations (left), DNA methylation changes (middle), and changes in expression levels determined by qRT PCR (right) are provided. FIG. 13P shows comparative analyses of effects of ecRNA upregulation and 5-Aza-CR treatment on TP73 promoter methylation and TP73 mRNA expression level, where lollipop representations (left) and DNA methylation changes (right) are provided. For FIGS. 13H-13K and 13P, error bars indicate means±s.d.; all bisulfite sequenced clones were analyzed by Fisher's exact test; MassARRAY data were analyzed by paired T-test; and *P<0.05; P<0.001; *P<0.001.

FIGS. 14A-14C are results from experiments showing that transcription impedes DNA methylation. FIGS. 14A and 14B show lollipop representations of bisulfite sequenced clones analyzed by Fisher's exact test (*P<0.05; P<0.01; *P<0.001). The right panels show DNA methylation changes as described in FIG. 13D. The same effect was observed with two different RNA polymerases: T7 and Sigma-Saturated (σ70)-Holoenzyme (*E. coli* RNA polymerase). FIG. 14C is a schematic showing the generation of hemimethylated DNA. (a and b) The region corresponding to the 5' region of the ecRNA genomic template was amplified using a forward primer containing the T7 promoter sequence and a biotinylated (arrowhead B) and not-biotinylated reverse primers containing a unique BstX1 restriction site (unmethylated DNA; umDNA). (c) Biotinylated umDNA was in vitro methylated with M.SssI (NEB). (d) Efficiency of methylation was assessed by restriction digestion of the methylated DNA (mDNA) with methylation insensitive and sensitive restriction enzymes MspI and HpaII, respectively. (e) 10× molar excess of not biotinylated umDNA was mixed with biotinylated mDNA. The mixture was denatured (100° C.; 5 minutes), quickly chilled to 70° C., and reannealed by slow chilling down to 4° C. (0 The biotinylated DNAs, a ~10:1 mixture of hmDNAs and mDNAs, were captured with streptavidin magnetic beads. (g) The beads were removed following BstX1 restriction digestion. (h) COBRA analysis was performed to assess the purity of the hmDNA. The primers for bisulfite converted DNA were designed against the upper (unmethylated) strand, hence BstU1I digestion of hmDNA and umDNA should present identical restriction patterns. Presence of trace amount of BStUI digestion fragments in hmDNA lane (marked with asterisk) reflects ~<10% of the mDNA in the mixture (e and f).

FIGS. 15A-15M show that DNMT1 binds to RNA with a greater affinity than to DNA. FIG. 15A is a result from an RNA immunoprecipitation (RIP) demonstrating that ecRNA is immunoprecipitated with anti-DNMT1 antibody in HL-60 cells. Error bars are means±s.d. FIG. 15B is a diagram showing the position and sequences of RNA (SEQ ID NOs:62, 63) and dsDNA oligonucleotides used in EMSA. Asterisks indicate position of methylated cytosines. umDNA (SEQ ID NOs:64, 71), hmDNA (SEQ ID NOs:65, 72), and mDNA (SEQ ID NOs:66, 73) refer to unmethylated, hemimethylated, and methylated DNA probes, respectively. FIG. 15C are RNA and DNA EMSA performed with a fixed concentration of ssRNA and dsDNAs (1 nM) and increasing concentrations of DNMT1 protein as indicated above the gel. FIG. 15D is a nonlinear regression analysis of bound RNNDNA vs. DNMT1 concentrations. Error bars indicate s.d. from two independent EMSAs. FIG. 15E shows the secondary structures predicted by RNAfold of ssRNA R05 (SEQ ID NO:62) and R04 (SEQ ID NO:63). FIG. 15F is a REMSA showing that R04 displays lower DNMT1 affinity compared to R05 (FIG. 15C, left panel) at the same DNMT1 concentrations. FIG. 15G is a graph showing that ecRNA specifically immunoprecipitates with anti-hDNMT1 antibody in U937 cells. FIG. 15H shows the enrichment of non-polyadenylated ecRNA in DNMT1-RNA precipitate (PolyA(−)) in HL-60 cells. The schematics outline the tested procedure and the TaqMan probe set (black double headed arrow) used to detect both C/EBPa transcripts (polyadenylated CEBPa mRNA and non-polyadenylated C/EBPa ecRNA). FIG. 15I is a diagram showing positions and sequences of RNA (SEQ ID NO:60) and DNA (SEQ ID NOs:61, 67, 70, 74) oligonucleotides used in EMSA, where possible stem-loop-like folding within the ecRNA sequence is also shown. dsRNA oligo represents imperfect duplex between RNA oligo R01 and R03; double-stranded DNA oligo correspond to the sequences of the RNA oligo. FIG. 15J shows RNA and DNA EMSA performed with increasing amounts of competitors: polydl-dC and dsDNA. FIG. 15K shows secondary structures of R01 (SEQ ID NO:68) and mutated R01 (SEQ ID NO:69). Both are able to form stem-and-loop-like structures. Asterisks indicate C to U substitutions. FIG. 15L is a gel showing that DNMT1 binding to folded ssRNA is not affected by the absence of CpG dinucleotides when stem-and-loop-like structure is preserved. FIG. 15M is an RNA EMSA performed in the presence of increasing concentration of spermine, where no significant changes in binding were observed.

FIG. 16A is a pie chart showing distribution of specific DNMT1 library peaks. FIG. 16B is a comparison of gene expression and methylation levels between DNMT1 unbound and DNMT1 bound groups (P<0.0001). FIG. 16C shows a DNMT1 Epitranscriptome map, where the cloud plots representing genes within DNMT1 unbound and bound groups were stratified by methylation and expression levels. FIG. 16D shows examples of genes falling into the C (C/EBPa) and B (USP29) clusters. Peaks are visualized using SISSRs (Site Identification from Short Sequence Reads) (Jothi et al., Nucleic Acid Res 36:5221-5231, 2008). FIG. 16E is a chart showing enrichment of C/EBPa ecRNA in a cDNA library made of RNAs that co-immunoprecipitated with anti-hDNMT1 antibody. FIG. 16F is a flow chart of RIPseq analysis showing various steps applied for the comparative RIPseq and RRBS analyses. FIGS. 16G and 16H are additional examples of genes in clusters C and B.

DETAILED DESCRIPTION

Figure 1A:
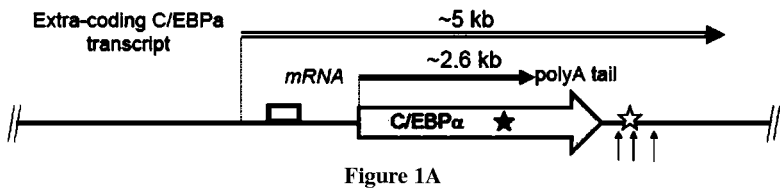

Contrary to traditional views that DNA methylation affects gene expression, we have discovered that gene expression, i.e., transcription, affects DNA methylation. Our discovery is based on the observation that (i) double-stranded RNA molecules bind to DNA methyltransferase (DNMT1), (ii) single-stranded RNA of the same primary structure have low to zero capacity to bind DNMT1, and (iii) DNMT1 is inactive during transcription. Based on these observations, we developed single-stranded chimeric RNA oligonucleotides (CROs) having the dual ability to inactivate DNA methyltransferase (DNMT) by enhanced binding between an RNA sequence and DNMT and to target a specific gene during transcription by binding an extra-coding RNA or by triplex formation with genomic DNA. Though the extra-coding RNA can include both coding and non-coding regions, we have discovered that non-coding regions of an extra-coding RNA may play a functional role in gene expression.

Without wishing to be limited by theory, we hypothesize that: (i) cell-type specific transcription is an underlying cause of the diverse methylation patterns; (ii) RNAs as physical entities could establish and maintain cell-type specific methylation patterns; (iii) modulation of expression levels of selected transcripts may change methylation patterns of respective genes and ultimately gene expression; and (iv) the enhanced ability of RNA to bind DNMT1 could be exploited in the development of a novel, therapeutic gene-specific demethylating agent.

Gene-specific CROs can be obtained by including unique genomic sequences with low capacity to form secondary structures. When the CRO form a double-stranded duplex with their target, i.e., a naturally occurring RNA, the formed duplex will bind DNMT1 through its observed binding capacity to dsRNA. When the gene target is not available, such as when the RNA is not being transcribed, then the lack of secondary structure will prevent CROs from non-specifically binding DNMT1. In this manner, the CROs target specific genes and avoid the global demethylating effect observed with traditional demethylating agents. Non-limiting examples of the CRO interacting with transcribed RNA is provided in FIGS. 6C and 6D.

Furthermore, these chimeric RNA oligonucleotides can be used to deliver additional demethylating agents. For example, 5-azacytidine and or 5-aza-2'-deoxycytidine covalently bind DNMT1, and these known agents can be incorporated into CROs to further enhance binding between DNMT and RNA sequences. For example, when the CRO includes 5-aza-2'-deoxycytidine and forms a double-stranded duplex with its gene target, then DNMT1 can bind via the secondary structure of the duplex and the 5-aza-modification in cytidine.

Taken together, these chimeric RNA oligonucleotides can be used to treat various diseases associated with aberrant DNMT activity, such as cancer, and to develop a new field of customized, gene-targeted demethylating therapy.

Chimeric RNA Oligonucleotides

The chimeric RNA oligonucleotide (CRO) of the invention is capable of reducing the activity of DNA methyltransferase and selectively or specifically hybridizing to a target sequence in a gene and/or to a corresponding extra-coding RNA. The CRO includes a sequence of about 15 to about 30 nucleotides having percentage complementarity to an extra-coding RNA of a gene. The formed duplex (with an extra-coding RNA) and/or triplex (with the respective genomic sequence) will allow for binding to DNMT. This binding will result in sequence-specific protection of the respective genomic sequences from the enzymatic activity of DNMT. Accordingly, these chimeric RNA oligonucleotides can be used for treatment (e.g., as an agent for cancer therapy) or for diagnostic methods or kits (e.g., as a probe for a diagnostic assay).

The RNA sequence of the CRO binds DNMT and reduces methylating activity. As described herein, DNMT strongly interacts with RNA in a manner that is not sequence-specific. In particular, DNMT can bind RNA more strongly than DNA with the same primary structure. Optionally, binding between the CRO and DNMT could be further enhanced by including one or more modified nucleotides (e.g., cytidine or analogs thereof) that covalently bind to DNMT. Exemplary cytidine analogs are described herein.

Figure 7A:
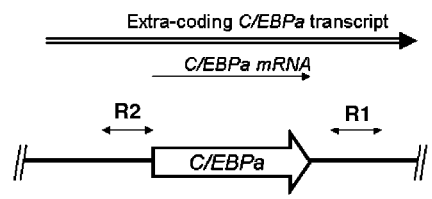
Figure 7B:
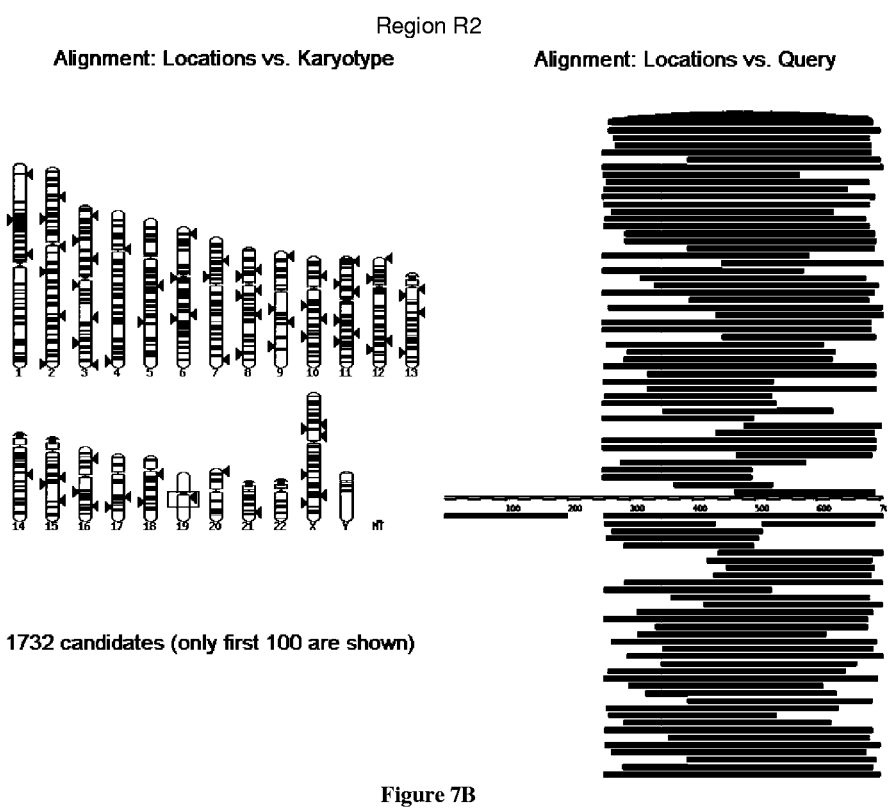

In addition to binding DNMT, the CRO includes a sequence to selectively or specifically hybridizing to its target sequence, i.e., an extra-coding RNA (ecRNA), of a gene. Binding of the CRO to the ecRNA can be determined by any useful method. Optionally, the methods can be performed under stringent conditions. For example, BLAST searches can be performed at high stringency conditions (as shown in FIGS. 7B-7C) and/or Northern blot hybridization assays can be performed at a lower concentration of sodium chloride (e.g., 0.2 M NaCl, 0.1 M NaCl, or 50 mM NaCl) (as shown in FIG. 7D). Exemplary gene targets for CROs are provided herein.

Extra-Coding RNA

Extra-coding RNAs (ecRNAs) can include both coding and non-coding regions of a gene. In particular, the CRO includes a sequence that is gene-specific. Exemplary genes include: C/EBPa (CCAAT enhancer binding protein alpha, cluster C (GO Accession No.: GO:0010605), HGNC Accession No.: 1833, NCBI Ref. Nos.: NP_004355.2, NM_004364.3); SPI1 (spleen focus forming virus (SFFV) proviral integration oncogene spi1, cluster C (GO:0010605), HGNC:11241, NCBI: NP_001074016.1, NM_001080547.1); RXRA (retinoid X receptor, alpha, cluster C (GO:0010605), HGNC:10477, NCBI:NP_002948.1, NM_002957.4); RARB (retinoic acid receptor, beta, HGNC:9865, NCBI:NP_000956.2, NM_000965.3); RB1 (retinoblastoma 1, cluster C (GO:0007049, GO:0051276, GO:0022402, GO:0006325, GO:0000278, GO:0016568, GO:0010605, and GO:0022403), HGNC:9884, NCBI: NP_000312.2, NM_000321.2); CDKN2A (cyclin-dependent kinase inhibitor 2A, HGNC:1787, NCBI:NP_478102.1, NM_058195.2); CDH1 (cadherin 1, type 1, E-cadherin, HGNC:1748, NCBI:BAA88957.1, AB025106.1); CDH13 (cadherin 13, H-cadherin, HGNC:1753, NCBI: NP_001248.1, NM_001257.3); TIMP3 (TIMP metallopeptidase inhibitor 3, HGNC:11822, NCBI:NP_000353.1, NM_000362.4); VHL (von Hippel-Lindau tumor suppressor, HGNC:12687, NCBI:NP_000542.1, NM_000551.2); MLH1 (mutL homolog 1, colon cancer, nonpolyposis type 2, HGNC:7127, NCBI:NP_000240.1, NM_000249.3); MGMT (O-6-methylguanine-DNA methyltransferase, HGNC:7059, NCBI:NP_002403.2, NM_002412.3); BRCA1 (breast cancer 1, early onset, HGNC:1100, NCBI:NP_009231.2, NM_007300.3); GSTP1 (glutathione S-transferase pi 1, HGNC:4638, NCBI:NP_000843.1, NM_000852.3); HLTF (helicase-like transcription factor, HGNC:11099, NCBI: NP_620636.1, NM_139048.2); RASSF1 (Ras association (RalGDS/AF-6) domain family member 1, HGNC:9882, NCBI:NP_733833.1, NM_170715.1); SOCS1 (suppressor of cytokine signaling 1, HGNC:19383, NCBI:NP_003736.1, NM_003745.1); ESR1 (estrogen receptor 1, HGNC:3467, NCBI:NP_001116214.1, NM_001122742.1); and DAPK1 (death-associated protein kinase 1, HGNC:2674, NCBI: NP_004929.2, NM_004938.2). Exemplary gene-specific sequences for the CRO include the 3'-end of C/EBPa ecRNA provided in FIG. 8 (SEQ ID NO:1) and fragments of the C/EBPa ecRNA provided in FIG. 11 (SEQ ID N0:8); a region of SPI1 ecRNA, including the four regions provided in FIG. 9 (SEQ ID NOs:2-5); a region of RXRA ecRNA, including the two regions provided in FIG. 10 (SEQ ID NOs:6-7); and a region of RARB ecRNA, including fragments of the RARB ecRNA provided in FIG. 12 (SEQ ID NO:9).

Based on the various genes described herein (e.g., any described herein, such as those in cluster C), the gene-specific sequences for the CRO can be designed having a sequence that is at least 80% (e.g., at least 85%, 90%, 95%, 96%, 97%, 98%, 99% or more) complementary to a region spanning the promoter, the coding part of the gene, and/or the 3'-downstream part (e.g., −2 kilobases and/or +2 kilobases from the transcriptional start site (TSS) or the transcriptional end site (TES) of the genes, respectively). Any useful method can be used to determine such TSS and TES positions, including various databases (e.g., TESS: Transcription Element Search System, available at www.cbil.upenn.edu/tess/, and Transcriptional Regulatory Element Database (TRED), available at rulai.cshl.edu/cgi-bin/TRED/tred.cgi?process=home). Exemplary gene-specific sequences for the CRO include the 3'-end of C/EBPa ecRNA provided in FIG. 8 (SEQ ID NO:1) and fragments of the C/EBPa ecRNA provided in FIG. 11 (SEQ ID N0:8); a region of SPI1 ecRNA, including the four regions provided in FIG. 9 (SEQ ID NOs:2-5); a region of RXRA ecRNA, including the two regions provided in FIG. 10 (SEQ ID NOs:6-7); and a region of RARB ecRNA, including fragments of the RARB ecRNA provided in FIG. 12 (SEQ ID NO:9).

Also described herein are methods of identifying ecRNAs, as well as CROs that bind to such ecRNAs to form a complex and such complexes that bind DNMT. In some non-limiting embodiments, the CRO includes a sequence that is gene-specific (e.g., a complementary to a particular gene), where the gene is in cluster C, as described herein (e.g., see Example 8).

In some embodiments, the genes in cluster C belong to particular Gene Ontology (GO) categories (www.geneontology.org and The Gene Ontology Consortium, "Gene ontology: tool for the unification of biology," Nat. Genet. 25(1):25-29 (2009)). Exemplary non-limiting GO categories include genes related to conversion of one or more primary RNA transcripts into one or more mature RNA molecules (GO:0006396, RNA processing); genes related to biochemical and morphological phases that occur during successive cell or nuclear replication events (GO:0007049, cell cycle), genes related to chemical reactions and pathways involving mRNA (GO:0016071, mRNA metabolic process), genes related to assembly, arrangement, or disassembly of chromosomes (GO:0051276, chromosome organization), genes related to splicing and joining primary RNA transcript to form mature form of the RNA (GO:0008380, RNA splicing), genes related to cellular breakdown of macromolecules, large molecules (e.g., proteins), nucleic acids and carbohydrates (GO:0044265, cellular macromolecule catabolic process), genes related to cellular metabolic process involving deoxyribonucleic acid (GO:0006259, DNA metabolic process), genes related to conversion of a primary mRNA transcript into one or more mature mRNA (GO:0006397, mRNA processing), genes relate to breakdown of a macromolecule or any molecule of high relative molecular mass having multiple repetition of subunits (GO:0009057, macromolecule catabolic process), genes related to cellular processes involved in the progression of biochemical and morphological events that occur during successive cell or nuclear replication events (GO:0022402, cell cycle process), genes related to the specification, formation, or maintenance of the physical structure of eukaryotic chromatin (GO:0006325, chromatin organization), genes related to progression through the phases of the mitotic cell cycle (GO:0000278, mitotic cell cycle), genes related to alteration of DNA, protein, or RNA in chromatin (GO:0016568, chromatin modification), genes related to processes that decreases the frequency, rate, or extent of the chemical reactions and pathways involving macromolecules (GO:0010605, negative regulation of macromolecule metabolic process), genes related to chemical reactions and pathways resulting in the breakdown of a protein either with or without the hydrolysis of peptide bonds (GO:0030163, protein catabolic process), genes related to chemical reactions and pathways resulting in the breakdown of a protein or peptide (GO:0019941, modification-dependent protein catabolic process), genes related to chemical reactions and pathways resulting in the breakdown of a macromolecule (GO:0043632, modification-dependent macromolecule catabolic process), genes related to hydrolysis of a peptide resulting in the breakdown of a protein (GO:0051603, proteolysis involved in cellular protein catabolic process), and genes related to cell cycle processes involved in the progression of biochemical and morphological phases that occur during successive cell or nuclear replication events (GO:0022403, cell cycle phase), where definitions for such terms and related GO accessions numbers are provided on www.geneontology.org (AmiGO version 1.8, last accessed Apr. 11, 2012). Further exemplary non-limiting GO categories include GO:0044257, cellular protein catabolic process; GO:0006281, DNA repair; GO:0006974, response to DNA damage stimulus; GO:0006412, translation; GO:0006511, ubiquitin-dependent protein catabolic process; GO:0033554, cellular response to stress; GO:0046907, intracellular transport; GO:0000375, RNA splicing, via transesterification reactions; GO:0000398, nuclear mRNA splicing, via spliceosome; GO:0000377, RNA splicing, via transesterification reactions with bulged adenosine as nucleophile; GO:0051301, cell division; GO:0034660, ncRNA metabolic process; GO:0000279, M phase; GO:0010558, negative regulation of macromolecule biosynthetic process; GO:0010629, negative regulation of gene expression; GO:0009890, negative regulation of biosynthetic process; GO:0006260, DNA replication; GO:0006350, transcription; GO:0045449, regulation of transcription; GO:0031327, negative regulation of cellular biosynthetic process; GO:0010498, proteasomal protein catabolic process; GO:0043161, proteasomal ubiquitin-dependent protein catabolic process; GO:0000280, nuclear division; GO:0007067, mitosis; GO:0048285, organelle fission; GO:0051726, regulation of cell cycle; GO:0000087, M phase of mitotic cell cycle; GO:0045934, negative regulation of nucleobase, nucleoside, nucleotide and nucleic acid metabolic process; GO:0043933, macromolecular complex subunit organization; and GO:0016481, negative regulation of transcription.

Exemplary non-limiting genes in GO Accession No. GO:0006396 (RNA processing) include those having the following abbreviated name, the full name, the HGNC Accession No., and the chromosome location: SCAF1 (SR-related CTD-associated factor 1, HGNC:30403, 19q13.3-q13.4); RALY (RNA binding protein, autoantigenic (hnRNP-associated with lethal yellow homolog (mouse)), HGNC:15921, 20q11.21-q11.23); NCBP2 (nuclear cap binding protein subunit 2, 20 kDa, HGNC:7659, 3q29); EIF2C2 (eukaryotic translation initiation factor 2C, 2, HGNC:3263, 8q24); CHERP (calcium homeostasis endoplasmic reticulum protein, HGNC:16930, 19p13.1); RPL14 (ribosomal protein L14, HGNC:10305, 3p22-p21.2); RBM3 (RNA binding motif (RNP1, RRM) protein 3, HGNC:9900, Xp11.2); LSM6 (LSM6 homolog, U6 small nuclear RNA associated (S. cerevisiae), HGNC:17017, 4q31.21); RBM4 (RNA binding motif protein 4, HGNC:9901, 11q13); RBM5 (RNA binding motif protein 5, HGNC:9902, 3p21.3); SYNCRIP (synaptotagmin binding, cytoplasmic RNA interacting protein, HGNC:16918, 6q14-q15); ZNF638 (zinc finger protein 638, HGNC:17894, 2p13.1); SART3 (squamous cell carcinoma antigen recognized by T cells 3, HGNC:16860, 12q24.11); WTAP (Wilms tumor 1 associated protein, HGNC:16846, 6q25-q27); PNN (pinin, desmosome associated protein, HGNC:9162, 14q21.1); PUS7L (pseudouridylate synthase 7 homolog (S. cerevisiae)-like, HGNC:25276, 12q12); APP (amyloid beta (A4) precursor protein, HGNC:620, 21q21.2); DDX23 (DEAD (Asp-Glu-Ala-Asp) box polypeptide 23 (SEQ ID NO:56), HGNC:17347, 12q13.11); DHX38 (DEAD (Asp-Glu-Ala-His) box polypeptide 38 (SEQ ID NO:57), HGNC:17211, 16q22); SRRM2 (serine/arginine repetitive matrix 2, HGNC:16639, 16p13.3); TARDBP (TAR DNA binding protein, HGNC:11571, 1p36.22); INTS6 (integrator complex subunit 6, HGNC:14879, 13q14.3); U2AF1 (U2 small nuclear RNA auxiliary factor 1, HGNC:12453, 21q22.3); LSM5 (LSM5 homolog, U6 small nuclear RNA associated (S. cerevisiae), HGNC:17162, 7p14.3); LSM4 (LSM4 homolog, U6 small nuclear RNA associated (S. cerevisiae), HGNC:17259, 19p13.1); SRRM1 (serine/arginine repetitive matrix 1, HGNC:16638, 1p36); LSM3 (LSM3 homolog, U6 small nuclear RNA associated (S. cerevisiae), HGNC:17874, 3p25.1); PTBP2 (polypyrimidine tract binding protein 2, HGNC:17662, 1p21.3); TGS1 (trimethylguanosine synthase 1, HGNC:17843, 8q11); RBM10 (RNA binding motif protein 10, HGNC:9896, Xp11.3); IMP4 (IMP4, U3 small nucleolar ribonucleoprotein, homolog (yeast), HGNC:30856, 2q21.1); CCAR1 (cell division cycle and apoptosis regulator 1, HGNC:24236, 10q22.1); PABPN1 (poly(A) binding protein, nuclear 1, HGNC:8565, 14q11.2); RRP1 (ribosomal RNA processing 1 homolog (S. cerevisiae), HGNC:18785, 21q22.3); SF3B14

(Splicing Factor 3B, 14-kD subunit, HPRD: 09702, 2pter-p25.1); EMG1 (EMG1 nucleolar protein homolog (*S. cerevisiae*), HGNC:16912, 12p13); PTBP1 (polypyrimidine tract binding protein 1, HGNC:9583, 19p13.3); HNRNPA2B1 (heterogeneous nuclear ribonucleoprotein A2/B1, HGNC:5033, 7p15); RRP9 (ribosomal RNA processing 9, small subunit (SSU) processome component, homolog (yeast), HGNC:16829, 3p21.31); HNRNPR (heterogeneous nuclear ribonucleoprotein R, HGNC:5047, 1p36.12); HNRNPU (heterogeneous nuclear ribonucleoprotein U (scaffold attachment factor A), HGNC:5048, 1q44); RNMTL1 (RNA methyltransferase like 1, HGNC:18485, 17p13.3); BICD1 (bicaudal D homolog 1 (*Drosophila*), HGNC:1049, 12p11.2-p11.1); RSL1D1 (ribosomal L1 domain containing 1, HGNC:24534, 16p13.13); WDR83 (WD repeat domain 83, HGNC:32672, 19p13.13); PCF11 (PCF11, cleavage and polyadenylation factor subunit, homolog (*S. cerevisiae*), HGNC:30097, 11q13); PA2G4 (proliferation-associated 2G4, 38 kDa, HGNC:8550, 12q13.2); NOP2 (NOP2 nucleolar protein homolog (yeast), HGNC:7867, 12p13); RPS16 (ribosomal protein S16, HGNC:10396, 19q13.1); RPS14 (ribosomal protein S14, HGNC:10387, 5q31-q33); SNRPA (small nuclear ribonucleoprotein polypeptide A, HGNC:11151, 19q13.1); SNRPG (small nuclear ribonucleoprotein polypeptide G, HGNC11163, 2p13.3); CPSF3L (cleavage and polyadenylation specific factor 3-like, HGNC:26052, 1p36.33); FIP1L1 (FIP1 like 1 (*S. cerevisiae*), HGNC:19124, 4q11-q12); ELAC2 (elaC homolog 2 (*E. coli*), HGNC:14198, 17p11.2); PUS1 (pseudouridylate synthase 1, HGNC:15508, 12q24); STRAP (serine/threonine kinase receptor associated protein, HGNC:30796, 12p13.1); TRPT1 (tRNA phosphotransferase 1, HGNC:20316, 11q13); NAA38 (N(alpha)-acetyltransferase 38, NatC auxiliary subunit, HGNC:20471, 7q31.1-q31.3); ZFC3H1 (zinc finger, C3H1-type containing, HGNC:28328, 12q21.1); HNRNPL (heterogeneous nuclear ribonucleoprotein L, HGNC:5045, 19q13.2); HNRNPM (heterogeneous nuclear ribonucleoprotein M, HGNC:5046, 19p13.3-p13.2); DDX46 (DEAD (Asp-Glu-Ala-Asp) box polypeptide 46 (SEQ ID NO 56), HGNC:18681, 5q31.1); RPS28 (ribosomal protein S28, HGNC:10418, 19p13.2); CNOT6L (CCR4-NOT transcription complex, subunit 6-like, HGNC:18042, 4q13.3); METTL1 (methyltransferase like 1, HGNC:7030, 12q13); HNRNPF (heterogeneous nuclear ribonucleoprotein F, HGNC:5039, 10q11.21); PRKRA (protein kinase, interferon-inducible double stranded RNA dependent activator, HGNC:9438, 2q31.2); HNRNPD (heterogeneous nuclear ribonucleoprotein D (AU-rich element RNA binding protein 1, 37 kDa), HGNC: 5036, 4q21); HNRNPC (heterogeneous nuclear ribonucleoprotein C (C1/C2), HGNC:5035, 14q11); RPL10A (ribosomal protein L10a, HGNC:10299, 6p21.31); PABPC1 (poly(A) binding protein, cytoplasmic 1, HGNC:8554, 8q22.2-q23); ARL6IP4 (ADP-ribosylation-like factor 6 interacting protein 4, HGNC:18076, 12q24.31); DDX41 (DEAD (Asp-Glu-Ala-Asp) box polypeptide 41 (SEQ ID NO:56), HGNC:18674, 5q35.3); RPS24 (ribosomal protein S24, HGNC:10411, 10q22); PRPF40A (PRP40 pre-mRNA processing factor 40 homolog A (*S. cerevisiae*), HGNC: 16463, 2q23.3); RTCD1 (RICA) (RNA 3'-terminal phosphate cyclase, HGNC:17981, 1p13.3); MPHOSPH10 (M-phase phosphoprotein 10 (U3 small nucleolar ribonucleoprotein), HGNC:7213, 2p13.3); SMAD2 (SMAD family member 2, HGNC:6768, 18q21); RNPS1 (RNA binding protein S1, serine-rich domain, HGNC:10080, 16p13.3); CASC3 (cancer susceptibility candidate 3, HGNC:17040, 17q11-q21.3); INTS10 (integrator complex subunit 10, HGNC:25548, 8p21.3); DDX5 (DEAD (Asp-Glu-Ala-Asp) box helicase 5 (SEQ ID NO:56), HGNC: 2746, 17q21); U2AF1L4 (U2 small nuclear RNA auxiliary factor 1-like 4, HGNC:23020, 19q13.13); RBMX (RNA binding motif protein, X-linked, HGNC:9910, Xq26); HNRNPA1 (heterogeneous nuclear ribonucleoprotein A1, HGNC:5031, 12q13.1); HNRNPA0 (heterogeneous nuclear ribonucleoprotein A0, HGNC:5030, 5q31); NOP14 (NOP14 nucleolar protein hornolog (yeast), HGNC:16821, 4p16.3); URM1 (ubiquitin related modifier 1, HGNC:28378, 9q34.13); DDX56 (DEAD (Asp-Glu-Ala-Asp) box helicase 56 (SEQ ID NO:56), HGNC:18193, 7p13); HNRNPH3 (heterogeneous nuclear ribonucleoprotein H3 (2H9), HGNC:5043, 10q22); UPF3B (UPF3 regulator of nonsense transcripts homolog B (yeast), HGNC:20439, Xq25-q26); NOLC1 (nucleolar and coiled-body phosphoprotein 1, HGNC:15608, 10q24.32); GTF2F1 (general transcription factor IIF, polypeptide 1, 74 kDa, HGNC:4652, 19p13.3); WDR3 (WD repeat domain 3, HGNC:12755, 1p12); DDX54 (DEAD (Asp-Glu-Ala-Asp) box polypeptide 54 (SEQ ID NO:56), HGNC:20084, 12q24.11); HNRNPH1 (heterogeneous nuclear ribonucleoprotein H1 (H), HGNC: 5041, 5q35.3); SMC1A (structural maintenance of chromosomes 1A, HGNC:11111, Xp11.22-p11.21); PDCD7 (programmed cell death 7, HGNC:8767, 15q22.2); POP7 (processing of precursor 7, ribonuclease P/MRP subunit (*S. cerevisiae*), HGNC:19949, 7q22); PUF60 (poly-U binding splicing factor 60KDa, HGNC:17042, 8q24.3); ADAR (adenosine deaminase, RNA-specific, HGNC:225, 1q21.3); UTP18 (UTP18 small subunit (SSU) processome component homolog (yeast), HGNC:24274, 17q21.33); WBP4 (WW domain binding protein 4 (formin binding protein 21), HGNC:12739, 13q13.3); HNRPLL (heterogeneous nuclear ribonucleoprotein L-like, HGNC:25127, 2p22); RNGTT (RNA guanylyltransferase and 5'-phosphatase, HGNC: 10073, 6q16); DKC1 (dyskeratosis congenita 1, dyskerin, HGNC:2890, Xq28); DGCR8 (DiGeorge syndrome critical region gene 8, HGNC:2847, 22q11.2); TRMT6 (tRNA methyltransferase 6 homolog (*S. cerevisiae*), HGNC:20900, 20p12.3); PCBP1 (poly(rC) binding protein 1, HGNC:8647, 2p13-p12); PCBP2 (poly(rC) binding protein 2, HGNC: 8648, 12q13.12-q13.13); QKI (QKI, KH domain containing, RNA binding, HGNC:21100, 6q26); TSEN2 (tRNA splicing endonuclease 2 homolog (*S. cerevisiae*), HGNC:28422, 3p25.2); FTSJ1 (FtsJ homolog 1 (*E. coli*), HGNC:13254, Xp11.23); ZCCHC6 (zinc finger, CCHC domain containing 6, HGNC:25817, 9q21); DUS1L (dihydrouridine synthase 1-like (*S. cerevisiae*), HGNC:30086, 17q25.3); FTSJ3 (FtsJ homolog 3 (*E. coli*), HGNC:17136, 17q23); TFIP11 (tuftelin interacting protein 11, HGNC:17165, 22q12.1); PPP2R1A (protein phosphatase 2, regulatory subunit A, alpha, HGNC: 9302, 19q13); EXOSC8 (exosome component 8, HGNC: 17035, 13q13.1); ZCCHC11 (zinc finger, CCHC domain containing 11, HGNC:28981, 1p32.3); EXOSC4 (exosome component 4, HGNC:18189, 8q24.3); SARS (seryl-tRNA synthetase, HGNC:10537, 1p13.3); SF1 (splicing factor 1, HGNC:12950, 11q13); PRPF3 (PRP3 pre-mRNA processing factor 3 homolog (*S. cerevisiae*), HGNC:17348, 1q21.1); EXOSCI (exosome component 1, HGNC:17286, 10q24); PRPF4 (PRP4 pre-mRNA processing factor 4 hornolog (yeast), HGNC:17349, 9q31-q33); TTF2 (transcription termination factor, RNA polymerase II, HGNC:12398, 1p13.1); PRPF6 (PRP6 pre-mRNA processing factor 6 homolog (*S. cerevisiae*), HGNC:15860, 20q13.33); TARBP1 (TAR (HIV-1) RNA binding protein 1, HGNC: 11568, 1q42.2); HNRPDL (heterogeneous nuclear ribonucleoprotein D-like, HGNC:5037, 4q21.22); EIF4A3 (eukaryotic translation initiation factor 4A3, HGNC:18683, 17q25.3); PAPD4 (PAP associated domain containing 4, HGNC:26776, 5q14.1); ROD1 (PTBP3) (polypyrimidine tract binding protein 3, HGNC:10253, 9q32); SNRNP200 (small nuclear ribonucleoprotein 200 kDa (U5), HGNC: 30859, 2q11.2); CPSF7 (cleavage and polyadenylation specific factor 7, 59 kDa, HGNC:30098, 11q12.2); CPSF6 (cleavage and polyadenylation specific factor 6, 68 kDa, HGNC:13871, 12q15); SNRNP40 (small nuclear ribonucleoprotein 40 kDa (U5), HGNC:30857, 1p35.2); THOC4 (ALYREF) (Aly/REF export factor, HGNC:19071, 17q25.3); CPSF4 (cleavage and polyadenylation specific factor 4, 30 kDa, HGNC:2327, 7q22); RBM39 (RNA binding motif protein 39, HGNC:15923, 20q11.22); CPSF3 (cleavage and polyadenylation specific factor 3, 73 kDa, HGNC:2326, 2p25.1); THOC3 (THO complex 3, HGNC: 19072, 5q35.3); CPSF2 (cleavage and polyadenylation specific factor 2, 100 kDa, HGNC:2325, 14q31.1); NHP2 (NHP2 ribonucleoprotein homolog (yeast), HGNC:14377, 5q35.3); TRUB2 (TruB pseudouridine (psi) synthase homolog 2 (*E. coli*), HGNC:17170, 9); PRPF38B (PRP38 pre-mRNA processing factor 38 (yeast) domain containing B, HGNC:25512, 1p13.3); SSU72 (SSU72 RNA polymerase II CTD phosphatase hornolog (*S. cerevisiae*), HGNC:25016, 1p36); THOC1 (THO complex 1, HGNC:19070, 18p11.32); POLR2H (polymerase (RNA) II (DNA directed) polypeptide H, HGNC:9195, 3q28); POLR2L (polymerase (RNA) II (DNA directed) polypeptide L, 7.6 kDa, HGNC:9199, 11p15); POLR2J (polymerase (RNA) II (DNA directed) polypeptide J, 13.3 kDa, HGNC:9197, 7q11.2); TRA2B (transformer 2 beta homolog (*Drosophila*), HGNC:10781, 3q26.2-q27); UTP6 (UTP6, small subunit (SSU) processome component, homolog (yeast), HGNC:18279, 17q11.2); WBP11 (WW domain binding protein 11, HGNC:16461, 12p12.3); QTRT1 (queuine tRNA-ribosyltransferase 1, HGNC:23797, 19p13.3); POLR2D (polymerase (RNA) II (DNA directed) polypeptide D, HGNC:9191, 2q21); IVNS1ABP (influenza virus NSIA binding protein, HGNC: 16951, 1q25.1-q31.1); POLR2C (polymerase (RNA) II (DNA directed) polypeptide C, 33 kDa, HGNC:9189, 16q13-q21); POLR2A (polymerase (RNA) II (DNA directed) polypeptide A, 220 kDa, HGNC:9187, 17p13.1); SF3B2 (splicing factor 3b, subunit 2, 145 kDa, HGNC: 10769, 11q13); PRPF19 (PRP19/PSO4 pre-mRNA processing factor 19 homolog (*S. cerevisiae*), HGNC:17896, 11q12.2); EXOSC10 (exosome component 10, HGNC: 9138, 1p36.22); PPP2CA (protein phosphatase 2, catalytic subunit, alpha isozyme, HGNC:9299, 5q31.1); PRPF8 (PRP8 pre-mRNA processing factor 8 homolog (*S. cerevisiae*), HGNC:17340, 17p13.3); USP39 (ubiquitin specific peptidase 39, HGNC:20071, 2p11.2); ADAT2 (adenosine deaminase, tRNA-specific 2, HGNC:21172, 6q24.2); SCNM1 (sodium channel modifier 1, HGNC:23136, 1q21.3); SNRNP70 (small nuclear ribonucleoprotein 70 kDa (U1), HGNC:11150, 19q13.3); NSUN2 (NOP2/Sun domain family, member 2, HGNC:25994, 5p15.32); RBM28 (RNA binding motif protein 28, HGNC:21863, 7q32.2); PPWD1 (peptidylprolyl isomerase domain and WD repeat containing 1, HGNC:28954, 5q12.3); TYW1B (tRNA-yW synthesizing protein 1 homolog B (*S. cerevisiae*), HGNC:33908, 7q11.23); TXNL4B (thioredoxin-like 4B, HGNC:26041, 16q22.2); PDCD11 (programmed cell death 11, HGNC: 13408, 10q24.32); TRMU (tRNA 5-methylaminomethyl-2-thiouridylate methyltransferase, HGNC:25481, 22q13); RBM23 (RNA binding motif protein 23, HGNC:20155, 14q11.1); SF3A2 (splicing factor 3a, subunit 2, 66 kDa, HGNC:10766, 19p13.3-p13.2); SF3A1 (splicing factor 3a, subunit 1, 120 kDa, HGNC:10765, 22q12.2); SF3A3 (splicing factor 3a, subunit 3, 60 kDa, HGNC:10767, 1p); SLBP (stem-loop binding protein, HGNC:10904, 4p16.3); DIS3 (DIS3 mitotic control homolog (*S. cerevisiae*), HGNC: 20604, 13q21.32); HNRNPUL1 (heterogeneous nuclear ribonucleoprotein U-like 1, HGNC:17011, 19q13.31); PPP1R8 (protein phosphatase 1, regulatory subunit 8, HGNC:9296, 1p35.3); SFPQ (splicing factor proline/glutamine-rich, HGNC:10774, 1p34.3); LSM10 (LSM10, U7 small nuclear RNA associated, HGNC:17562, 1p34.3); NOP56 (NOP56 ribonucleoprotein homolog (yeast), HGNC:15911, 20p13); RBM14 (RNA binding motif protein 14, HGNC:14219, 11q13.2); and TXNL4A (thioredoxin-like 4A, HGNC:30551, 18q23).

Additional exemplary genes also include those having the following abbreviated names, where the full name, the HGNC Accession No., and the chromosome location can be accessed by using any useful database (e.g., HUGO Gene Nomenclature Committee (HGNC, available at www.genenames.org/hgnc-searches), Human Protein Reference Database (HPRD, available at www.hprd.org/index_html), or the NCBI Database): GO:0007049, cell cycle (ADCY3, MRPL41, AURKB, CDC16, WTAP, CD2AP, CTNNB1, CDCA8, APP, DDX11, INCENP, ILK, VPS4B, CDCA2, VPS4A, H2AFX, TLK1, TLK2, SUPT5H, CCNA2, CDCA5, CCAR1, CDCA3, ANAPC1, RAN, LIG1, POLE, SKP2, LIG3, ESPL1, UBR2, LIG4, NCAPD3, DCTN2, NCAPD2, MAPK1, UHRF1, PPP1 CA, RCC2, SPAG5, CNTROB, TBRG1, MAD2L2, MRE11A, CDC34, CALR, RCC1, PIN1, SAC3D1, NCAPG2, SPIN2B, TCF3, NUDC, SSSCA1, MLL, MKI67, MAP2K1, PCNT, NUF2, PCNP, CDC20, CDC26, RAD54L, ATM, NOTCH2, NOLC1, DMTF1, UBA3, CHAF1A, CCNT1, GTSE1, CCNE1, SEH1L, FANCI, DYNC1H1, FANCA, MYC, DHCR24, CDC7, CCNK, ARHGEF2, RBBP4, DSN1, CCNF, SF1, TPX2, PAPD7, RAD52, JMY, KLHDC3, RAD51, CCND1, CHMP1B, CCND3, CCND2, TOP3A, ADAM17, SIAH2, USP22, PML, BCCIP, ZNF655, NCAPH, NCAPG, BCL2, NPAT, PKD2, PPP3CA, BUB3, TRIP13, TXNL4B, UPF1, PDS5A, GMNN, ILF3, APPL1, MIS12, CCNB1, RASSF4, PSMD14, PSMD13, ERBB2IP, GSK3B, CALM3, CALM2, DNM2, TXNL4A, CALM1, BARD1, PRC1, PKMYT1, RBM7, MLL5, RAD21, TARDBP, TUBG1, ASPM, RBL2, PLKIS1, PPPICC, TACC3, PPP1CB, AHR, WEE1, PSMA2, PSMA1, PA2G4, EP300, TIMELESS, PSMA4, AKAP8, DSCC1, KATNB1, ANAPC11, PSMA7, CCNG2, PSMB5, PSMB4, GADD45GIP1, NIPBL, PSMB1, SMARCB1, FBXO43, TUBE1, CLASP2, HELLS, TFDP1, CREBL2, TAF1, WDR6, HDAC3, CDKN1B, PSMC5, PSMC4, PLK1, ZNF318, ABL1, SMCIA, CCNDBP1, MYH10, E2F1, MAD1L1, E2F2, E2F3, E2F4, E2F8, RHOU, AKT1, CDC45, MCM8, PSMC3IP, PSMD1, PSMD2, PSMD3, RANBP1, PSMD6, PSMD7, ARL2, NUSAP1, CDK6, UBE2I, RB1, MCM2, MCM3, CDK4, CDK5, CDK2, MCM6, GAK, MFN2, RIF1, PSME1, PSME2, UBC, HAUS5, FOXM1, USP9X, CAMK2G, HCFC1, CDC73, TSPYL2, HJURP, PAFAH1B1, GFI1, NFATC1, CiPS1, TXNIP, BOD1, MSH2, PSRC1, CENPJ, CDC25A, SMC4, GPS2, GSPT1, CUL4A, and SETD8); GO:0016071, mRNA metabolic process (SCAF1, RALY, NCBP2, EIF2C2, LSM6, RBM4, RBM5, SYNCRIP, WTAP, PNN, APP, DDX23, DNAJB11, DHX38, SRRM2, TARDBP, U2AF1, LSM5, SRRM1, LSM4, LSM3, PTBP2, RBM10, TGS1, CCAR1, PAN2, PABPN1, PAN3, SF3B14, HNRNPA2B1, PTBP1, HNRNPR, HNRNPU, WDR83, PCF11, SERBP1, VEGFA, SNRPA, EIF2C3, SNRPG, FIP1L1, STRAP, IGF2BP1, MAPKAPK2, NAA38, HNRNPL, HNRNPM, DDX46, CNOT6L, HNRNPF, HNRNPD, HNRNPC, PABPC1, DDX41, PRPF40A, SMG5, PAIP1, SMG7, SMG1, RNPS1, CASC3, DDX5, RBMX, HNRNPA1, U2AFIL4, HNRNPA0, UPF3A, HNRNPH3, UPF3B, PNRC2, GTF2F1, SMC1A, HNRNPH1, PUF60, ADAR, WBP4, HNRPLL, AUH, YBX2, RNGTT, PCBP1, PCBP2, QKI, TSEN2, TFIP11, SF1, PRPF3, PRPF4, TTF2, PRPF6, EIF4A3, PAPD4, ROD1, SNRNP200, CPSF7, CPSF6, THOC4, SNRNP40, CPSF4, RBM39, CPSF3, THOC3, CPSF2, PRPF38B, SSU72, THOC1, POLR2H, POLR2L, POLR2J, TRA2B, WBP11, POLR2D, POLR2C, SF3B2, POLR2A, EXOSC10, PRPF19, ZFP36L2, PRPF8, USP39, SCNM1, SNRNP70, RBM28, PPWD1, TXNL4B, RBM23, UPF1, SF3A2, SF3A1, SF3A3, SLBP, GSPT1, HNRNPUL1, PPP1R8, SFPQ, LSM10, RBM14, and TXNL4A); GO:0051276, chromosome organization (MORF4L1, HIST2H2AA3, HIST2H2AA4, HMGN2, RBM4, CBX4, CBX3, H1FX, KDM1A, BRPF1, CDCA8, MLL5, H2AFV, BRPF3, DDX11, SMARCD2, H2AFZ, H2AFY, H2AFX, TLK1, HIRIP3, TLK2, MLL3, SUPT5H, CDCA5, MLL2, SATB1, RBL2, C11ORF30, MTA2, RCOR1, ARID1A, ESPL1, ARID1B, LIG4, NCAPD3, NCAPD2, SUZ12, EP300, KDM2A, BAZ1B, SMARCE1, SMARCA5, AKAP8, SMARCA2, EP400, DSCC1, SUPT6H, HMGB1, HMGB2, TADA3, SETD1B, MRE11A, SETD1A, TRRAP, VPS72, NIPBL, ACD, SMARCB1, NCAPG2, RNF168, SUPT7L, ASF1B, BCOR, HELLS, HIST2H3A, AEBP2, EHMT1, SETDB2, SMCHD1, MLL, NFE2, CREBBP, WRN, KAT5, RAD54L, HIST2H3C, UIMC1, HDAC5, TNKS1BP1, MSL3, HDAC3, HDAC2, PHF1, MSL1, SMARCC1, SMARCC2, SUPT16H, DNMT1, H3F3B, CHAF1A, SMC1A, HDAC7, RERE, PTGES3, HP1BP3, ARID4B, EZH2, CTCF, DMAP1, DKC1, SEH1L, GPX4, HIST2H2AC, KDM5A, KDM5B, KDM5C, BRD8, UBE2A, HIST1H1E, RBBP4, PAPD7, NUSAP1, RB1, MCM2, RBBP7, HMGA1, C20ORF20, BPTF, HIST2H2BE, HIST2H2BF, USP21, RUVBL2, USP22, CARM1, SRCAP, KDM6B, PRKDC, CDC73, NR3C1, ARID2, NCAPH, TSPYL2, SET, CHD7, HJURP, NCAPG, SAFB, CHD1, KDM3A, SUPT4H1, CHD6, BAZ2A, TINF2, BUB3, CHD3, KAT2A, MSH3, HIST1H2BF, MSH2, SIRT1, MIS12, SMC4, DOT1L, WHSC1L1, HIST1H2AI, CABIN1, PHF21A, SETD7, SETD8, KDM4A, HIST1H2AM, SETD2, and RBM14); GO:0008380, RNA splicing (SCAF1, RALY, NCBP2, LSM6, RBM4, RBM5, SYNCRIP, ZNF638, WTAP, PNN, DHX38, DDX23, SRRM2, TARDBP, U2AF1, LSM5, SRRM1, LSM4, LSM3, PTBP2, RBM10, TGS1, CCAR1, PABPN1, SF3B14, HNRNPA2B1, PTBP1, HNRNPR, HNRNPU, WDR83, PCF11, SNRPA, SNRPG, STRAP, TRPT1, NAA38, HNRNPL, HNRNPM, DDX46, HNRNPF, HNRNPD, HNRNPC, PABPC1, DDX41, ARL6IP4, PRPF40A, MPHOSPH10, RNPS1, CASC3, DDX5, RBMX, HNRNPA1, U2AF1L4, HNRNPA0, HNRNPH3, UPF3B, GTF2F1, SMC1A, HNRNPH1, PUF60, PDCD7, WBP4, PCBP1, PCBP2, QKI, TSEN2, TFIP11, PPP2R1A, SF1, PRPF3, PRPF4, TTF2, PRPF6, EIF4A3, SNRNP200, CPSF7, THOC4, SNRNP40, RBM39, CPSF3, CPSF2, THOC3, PRPF38B, THOC1, POLR2H, POLR2L, POLR2J, TRA2B, WBP11, POLR2D, IVNS1ABP, POLR2C, SF3B2, POLR2A, PRPF19, PRPF8, PPP2CA, USP39, SCNM1, SNRNP70, RBM28, PPWD1, TXNL4B, SF3A2, SF3A1, SF3A3, HNRNPUL1, PPP1R8, SFPQ, LSM10, RBM14, and TXNL4A); GO:0044265, cellular macromolecule catabolic process (MYLIP, CDC16, CD2AP, ZNRF2, WWP2, CUL9, CDCA3, AUP1, PAN2, ANAPC1, PAN3, SKP2, UBR4, UBR2, UBE2J2, UHRF1, PIAS4, FBXL8, UBR5, FBXL5, FBXL4, PIAS2, EIF2C3, FBXL3, RAD23B, RAD23A, UBA5, CDC34, ARIH1, ARIH2, FBXO9, FBXO7, PCNP, CDC20, CDC26, ATM, UPF3A, RNF6, UPF3B, UBA1, UBR2, UBA3, KIAA0368, LDLR, UBE2G1, UBE2G2, AUH, SENP6, FBXL19, FANCL, USP19, LONP1, MGRN1, NSMCE2, USP11, USP10, CCNO, MYC, USP14, ZCCHC11, UFD1L, HERC5, GTF2H3, HERC4, ERLIN1, HERC3, HERC2, WDR48, EIF4A3, SENP3, USP21, ADAM17, SIAH2, USP22, USP24, CLN6, USP7, USP3, C10ORF46, USP4, EDEM3, C12ORF51, EDEM1, MYCBP2, ZFP36L2, SUMO2, SQSTM1, RNASET2, USP39, PPP2CB, USP36, FBXW11, USP33, TRIP12, BUB3, USP31, UBXN1, UPF1, LRRC41, SPSB2, BIRC6, SOD1, CCNB1, PSMD14, PSMD13, PPP1R8, TCEB2, BARD1, NCBP2, IDE, CBX4, RABGEF1, RBCK1, RNF149, RNF34, RELA, USP1, SOCS7, PSMA2, PSMA1, MIB1, KDM2A, TRIM33, PSMA4, ASB1, RNF138, TNFAIP3, ASB6, NEDD8, ANAPC11, UBAC1, PSMA7, PSMB5, PSMB4, UBE2D2, FBXW5, PSMB1, FBXW4, FBXO43, HNRNPD, STAMBPL1, RNF168, RNF167, TRAF7, HECTD1, SMG5, SMG7, HACE1, SMG1, RNPS1, CASC3, ATG3, ATE1, URM1, PSMC5, PSMC4, VCP, OTUB1, PNRC2, BAP1, OS9, CASP3, PSMD1, PSMD2, PSMD3, PSMD6, PSMD7, UBE2A, DDB1, UBE2I, PSME1, UBE2K, PSME2, UBE2M, DDB2, UBC, KLHL12, UBE2S, CUEDC2, OTUD5, APH1A, UBE3B, USP9X, STUB1, UBE2R2, EXOSC10, RPA2, RNF123, ERCC5, MAP3K1, ERCC3, ERCC2, STAMBP, CBL, UBE2Q2, UBE2Q1, NCSTN, WSB1, MPG, HSP90B1, GMCL1, GSPT1, CUL4A, BAX, ENDOG, APAF1, and TBLIX); GO:0006259, DNA metabolic process (MMS19, MORF4L1, XRCC3, RBM4, XRCC1, MLL5, RAD21, PSIP1, H2AFX, PMS1, CIB1, MCM3AP, POLK, POLI, POLH, POLG, RAN, C11ORF30, USP1, LIG1, POLE, LIG3, RAD9A, TOPBP1, LIG4, RMI1, RFC5, UHRF1, RPAIN, DCLRE1B, RFC2, TBRG1, TNFAIP1, DSCC1, RAD23B, HMGB1, HMGB2, RAD23A, MRE11A, CDC34, BANF1, TK1, ACD, POLE3, SMARCB1, RNF168, POLQ, HELLS, MLL, EME2, TP53BP1, EME1, BRIP1, SMG1, WRN, KAT5, RAD54L, UIMC1, ATM, TNKS1BP1, VCP, PPIA, SUPT16H, DNMT1, PARP4, HSPD1, KCTD13, CHAF1A, ABL1, SMC1A, DUT, PTGES3, UVRAG, ZNF12, CTCF, DMAP1, PMS2L2, FANCL, MCM9, ANKRD17, CDC45, LONP1, CASP3, MCM8, DKC1, NT5M, FANCI, PSMC3IP, NSMCE2, POLG2, FANCG, TOP2B, FANCA, CCNO, MYC, HEMK1, CDC7, UBE2A, RBBP4, REV1, CCDC88A, GEN1, DDB1, PAPD7, GTF2H3, MCM2, TOP1MT, RAD52, MCM3, RBBP7, MCM4, HMGA1, CDK2, MCM5, JMY, MCM6, KLHDC3, RAD51, RRM2, TOP3A, DDB2, RUVBL2, REV3L, WRNIP1, PML, PRKDC, BCCIP, POLA2, PRPF19, TYMS, RPA2, ERCC5, SET, MUS81, GATAD2A, ERCC3, BAZ2A, APEX1, TINF2, ERCC2, TRIP13, SSRP1, UPF1, MSH3, MSH2, SMC6, SOD1, SIRT1, CDC25A, MPG, CUL4A, CSNK1D, CSNK1E, BAX, ENDOG, SFPQ, APAF1, NFIC, RBM14, REPIN1, and BARD1); GO:0006397, mRNA processing (SCAF1, RALY, NCBP2, EIF2C2, LSM6, RBM4, RBM5, SYNCRIP, WTAP, PNN, APP, DHX38, DDX23, SRRM2, TARDBP, U2AF1, LSM5, SRRM1, LSM4, LSM3, PTBP2, RBM10, TGS1, CCAR1, PABPN1, SF3B14, HNRNPA2B1, PTBP1, HNRNPR, HNRNPU, WDR83, PCF11, SNRPA, SNRPG, FIP1L1, STRAP, NAA38, HNRNPL, HNRNPM, DDX46, CNOT6L, HNRNPF, HNRNPD, HNRNPC, PABPC1, DDX41, PRPF40A, RNPS1, CASC3, DDX5, HNRNPA1, RBMX, U2AF1L4, HNRNPA0, HNRNPH3, UPF3B, GTF2F1, SMC1A, HNRNPH1, PUF60, ADAR, WBP4, HNRPLL, RNGTT, PCBP1, PCBP2, QKI, TSEN2, TFIP11, SF1, PRPF3, PRPF4, TTF2, PRPF6, EIF4A3, PAPD4, ROD1, SNRNP200, CPSF7, CPSF6, THOC4, SNRNP40, CPSF4, RBM39, CPSF3, CPSF2, THOC3, PRPF38B, SSU72, THOC1, POLR2H, POLR2L, POLR2J, TRA2B, WBP11, POLR2D, POLR2C, SF3B2, POLR2A, PRPF19, PRPF8, USP39, SCNM1, SNRNP70, RBM28, PPWD1, TXNL4B, RBM23, SF3A2, SF3A1, SF3A3, SLBP, HNRNPUL1, PPP1R8, SFPQ, LSM10, RBM14, and TXNL4A); GO:0009057, macromolecule catabolic process (USE1, MYLIP, CDC16, CD2AP, ZNRF2, WWP2, CUL9, CDCA3, AUP1, PAN2, ANAPC1, PANS, SKP2, UBR4, UBR2, UBE2J2, UHRF1, PIAS4, FBXL8, UBR5, FBXL5, FBXL4, YME1L1, PIAS2, EIF2C3, FBXL3, RAD23B, RAD23A, UBA5, CDC34, ARIH1, ARIH2, FBXO9, FBXO7, GUSB, PCNP, CDC20, CDC26, AFG3L2, ATM, UPF3A, RNF6, UPF3B, UBA1, UBA2, UBA3, KIAA0368, LDLR, UBE2G1, UBE2G2, AUH, SENP6, FBXL19, FANCL, USP19, LONP1, MGRN1, NSMCE2, USP11, USP10, CCNO, MYC, USP14, DHCR24, ZCCHC11, UFD1L, HERC5, GTF2H3, HERC4, ERLIN1, HERC3, HERC2, WDR48, EIF4A3, SENP3, USP21, MGEA5, ADAM17, SIAH2, USP22, USP24, CLN6, USP7, C10ORF46, USP3, USP4, EDEM3, C12ORF51, EDEM1, MYCBP2, ZPF36L2, SUMO2, SQSTM1, RNASET2, USP39, PPP2CB, USP36, FBXW11, USP33, TRIP12, BUB3, USP31, UBXN1, UPF1, LRRC41, SPSB2, BIRC6, SOD1, CCNB1, PSMD14, PSMD13, PPP1R8, TCEB2, BARD1, NCBP2, IDE, CBX4, RABGEF1, RBCK1, RNF149, RNF34, USP1, RELA, SOCS7, PSMA2, PSMA1, MIB1, KDM2A, TRIM33, PSMA4, ASB1, RNF138, TNFAIP3, ASB6, NEDD8, ANAPC11, PSMA7, UBAC1, PSMB5, PSMB4, UBE2D2, FBXW5, PSMB1, FBXW4, FBXO43, STAMBPL1, HNRNPD, RNF168, RNF167, TRAF7, HECTD1, SMG5, SMG7, HACE1, SMG1, RNPS1, CASC3, ATG3, ATE1, URM1, PSMC5, PSMC4, VCP, OTUB1, PNRC2, BAP1, OS9, AKT1, CASP3, PSMD1, PSMD2, PSMD3, PSMD6, MAN2B1, PSMD7, UBE2A, DDB1, UBE2I, CDK5, PSME1, PSME2, UBE2K, UBE2M, DDB2, UBC, KLHL12, UBE2S, CUEDC2, OTUD5, APH1A, UBE3B, USP9X, STUB1, UBE2R2, NGLY1, EXOSC10, RPA2, RNF123, ERCC5, MAP3K1, ERCC3, ERCC2, STAMBP, CBL, UBE2Q2, UBE2Q1, NCSTN, WSB1, MPG, HSP90B1, GMCL1, GSPT1, CUL4A, BAX, ENDOG, APAF1, and TBL1X); GO:0022402, cell cycle process (ADCY3, PRC1, PKMYT1, RBM7, AURKB, CDC16, CD2AP, CTNNB1, CDCA8, APP, MLL5, RAD21, DDX11, INCENP, TARDBP, ILK, CDCA2, H2AFX, TUBG1, CCNA2, CDCA5, ASPM, CDCA3, ANAPC1, RAN, POLE, LIG3, SKP2, UBR2, ESPL1, PLK1S1, TACC3, PPP1CB, WEE1, NCAPD3, NCAPD2, DCTN2, PSMA2, PSMA1, PA2G4, RCC2, TIMELESS, SPAG5, PSMA4, CNTROB, TBRG1, AKAP8, MAD2L2, DSCC1, MRE11A, KATNB1, ANAPC11, CDC34, CALR, PSMA7, RCC1, CCNG2, PSMB5, PSMB4, NIPBL, PSMB1, SAC3D1, NCAPG2, FBXO43, TUBE1, CLASP2, TCF3, HELLS, NUDC, SSSCA1, TAF1, MKI67, MAP2K1, PCNT, WDR6, NUF2, CDC20, CDC26, RAD54L, ATM, NOTCH2, HDAC3, CDKN1B, PSMC5, PSMC4, NOLC1, PLK1, ZNF318, ABL1, SMC1A, MYH10, E2F1, MAD1L1, E2F4, RHOU, GTSE1, AKT1, CCNE1, SEH1L, PSMC3IP, PSMD1, PSMD2, PSMD3, RANBP1, PSMD6, DYNC1H1, FANCA, PSMD7, MYC, DHCR24, CDC7, CCNK, ARHGEF2, DSN1, CCNF, SF1, PAPD7, TPX2, NUSAP1, UBE2I, CDK6, RB1, RAD52, CDK4, CDK2, JMY, KLHDC3, RAD51, MFN2, CCND1, PSME1, CCND2, PSME2, UBC, TOP3A, ADAM17, HAUS5, USP9X, CAMK2G, PML, ZNF655, NCAPH, NCAPG, BCL2, NPAT, PKD2, PAFAH1B1, GFI1, PPP3CA, BUB3, TRIP13, NFATC1, TXNL4B, BOD1, PDS5A, MSH2, ILF3, CENPJ, CDC25A, MIS12, SMC4, CCNB1, PSMD14, PSMD13, GSPT1, CUL4A, GSK3B, SETD8, DNM2, TXNL4A, and BARD1); GO:0006325, chromatin organization (MORF4L1, HIST2H2AA3, HIST2H2AA4, HMGN2, RBM4, CBX4, CBX3, H1FX, KDM1A, MLL5, BRPF1, H2AFV, BRPF3, SMARCD2, H2AFZ, H2AFY, H2AFX, TLK1, HIRIP3, TLK2, MLL3, SUPT5H, MLL2, SATB1, RBL2, C11ORF30, RCOR1, MTA2, ARID1A, ARID1B, SUZ12, EP300, KDM2A, BAZ1B, SMARCE1, SMARCA5, SMARCA2, EP400, SUPT6H, HMGB1, HMGB2, TADA3, SETD1B, SETD1A, TRRAP, VPS72, SMARCB1, RNF168, SUPT7L, ASF1B, BCOR, HELLS, HIST2H3A, AEBP2, MLL, SETDB2, NFE2, EHMT1, CREBBP, KAT5, HIST2H3C, UIMC1, HDAC5, MSL3, HDAC3, HDAC2, PHF1, MSL1, SMARCC1, SMARCC2, SUPT16H, DNMT1, H3F3B, CHAF1A, HDAC7, RERE, HP1BP3, ARID4B, EZH2, CTCF, DMAP1, GPX4, HIST2H2AC, KDM5A, KDM5B, KDM5C, BRD8, HIST1H1E, UBE2A, RBBP4, RB1, MCM2, RBBP7, HMGA1, C20ORF20, BPTF, HIST2H2BE, HIST2H2BF, USP21, RUVBL2, USP22, CARM1, SRCAP, KDM6B, CDC73, NR3C1, ARID2, TSPYL2, SET, CHD7, HJURP, SAFB, CHD1, KDM3A, SUPT4H1, CHD6, BAZ2A, CHD3, KAT2A, H1ST1H2BF, SIRT1, DOT1L, WHSC1L1, HIST1H2AI, CABIN1, PHF21A, SETD7, SETD8, KDM4A, HIST1H2AM, SETD2, and RBM14); 60:0000278, mitotic cell cycle (PRC1, PKMYT1, AURKB, CDC16, CD2AP, CDCA8, APP, RAD21, DDX11, INCENP, TARDBP, CDCA2, CCNA2, CDCA5, ASPM, CDCA3, ANAPC1, RAN, POLE, SKP2, ESPL1, PPP1CB, WEE1, NCAPD3, NCAPD2, DCTN2, PSMA2, PSMA1, TIMELESS, RCC2, SPAG5, PSMA4, AKAP8, MAD2L2, DSCC1, KATNB1, ANAPC11, CDC34, PSMA7, RCC1, CCNG2, PSMB5, PSMB4, NIPBL, PSMB1, SAC3D1, NCAPG2, CLASP2, TCF3, HELLS, NUDC, SSSCA1, TAF1, MAP2K1, NUF2, CDC20, CDC26, CDKN1B, PSMC5, NOLC1, PSMC4, PLK1, UBA3, SMC1A, ABL1, E2F1, MAD1L1, E2F4, RHOU, GTSE1, AKT1, CCNE1, SEHIL, PSMD1, PSMD2, PSMD3, PSMD6, DYNC1H1, PSMD7, CDC7, ARHGEF2, CCNK, DSN1, CCNF, PAPD7, TPX2, NUSAP1, UBE2I, CDK6, RB1, CDK4, CDK2, CCND1, PSME1, CCND2, PSME2, UBC, ADAM17, HAUS5, CAMK2G, USP9X, NCAPH, NCAPG, BCL2, NPAT, PAFAH1B1, GFI1, PPP3CA, BUB3, NFATC1, BOD1, TXNL4B, PDS5A, MIS12, CDC25A, SMC4, CCNB1, PSMD14, PSMD13, CUL4A, GSPT1, SETD8, TXNL4A, and DNM2); GO:0016568, chromatin modification (MORF4L1, RBM4, CBX4, CBX3, KDM1A, MLL5, BRPF1, SMARCD2, BRPF3, H2AFY, TLK1, TLK2, SUPT5H, MLL3, MLL2, RBL2, C11ORF30, RCOR1, ARID1A, ARID1B, SUZ12, EP300, SMARCE1, BAZ1B, KDM2A, SMARCA5, SMARCA2, EP400, SUPT6H, TADA3, SETD1B, SETD1A, TRRAP, VPS72, SMARCB1, SUPT7L, RNF168, BCOR, ASF1B, HELLS, AEBP2, MLL, SETDB2, EHMT1, CREBBP, KAT5, UIMC1, MSL3, HDAC5, HDAC3, HDAC2, PHF1, SMARCC1, MSL1, SMARCC2, DNMT1, RERE, HDAC7, EZH2, CTCF, DMAP1, KDM5A, KDM5B, KDM5C, BRD8, UBE2A, RBBP4, RB1, RBBP7, C20ORF20, BPTF, USP21, RUVBL2, USP22, CARM1, SRCAP, KDM6B, CDC73, NR3C1, ARID2, TSPYL2, CHD7, HJURP, CHD1, KDM3A, SUPT4H1, CHD6, BAZ2A, CHD3, KAT2A, SIRT1, DOT1L, WHSC1L1, CAB1N1, SETD7, PHF21A, SETD8, KDM4A, RBM14, and SETD2); GO:0010605, negative regulation of macromolecule metabolic process (EIF2C2, CDC16, CITED2, CTNNB1, ZGPAT, SIN3A, WWP2, SUPT5H, EIF2B4, EIF2B5, ANAPC1, RXRA, SKP2, RAD9A, PIAS4, RPS14, LRCH4, EIF2C3, EIF2AK4, IGF2BP1, IGF2BP3, CALR, VPS72, ACD, ATN1, DRAP1, BCOR, TCF25, HNRNPAB, IKZF1, SMAD4, NDFIP2, SMAD2, CDC20, SKI, CDC26, UBP1, MLX, UBA3, NCOR2, ADAR, SPI1, ZEB2, DMAP1, HSBP1, YBX2, AES, NR2F2, FAM129A, MYC, ZNF496, CTBP1, ZCCHC11, ANKHD1-EIF4EBP3, SPEN, MBD2, RBBP7, MBD1, MXD3, EIF4A3, G6PD, MGEA5, MTDH, PML, SET, PPP2CA, GATAD2A, AATF, SUPT4H1, BAZ2A, BUB3, JARID2, GMNN, TRIM28, YWHAB, ILF3, ANKHD1, PHF12, EIF2B1, STAT3, PSMD14, PSMD13, GSK3A, YWHAQ, PHF21A, RBM15, BARD1, JDP2, THRA, XPO5, CCDC85B, RBM3, IDE, CBX4, CBX3, MAF1, KDM1A, FNTA, EIF4EBP2, SND1, TIA1, INSR, AKIRIN2, SATB1, RELA, MTA2, CSDA, PSMA2, SUZ12, PSMA1, PA2G4, SMARCE1, TIMELESS, TRIM33, PSMA4, ASB1, SMARCA2, HMGB1, HMGB2, TH1L, ANAPC11, PSMA7, WT1, PSMB5, PSMB4, PSMB1, ITGAV, PRKRA, RUNX2, HELLS, EHMT1, RFX5, KAT5, FOXP4, UIMC1, HDAC5, HDAC3, HDAC2, PSMC5, CDKN1B, PSMC4, SMARCC2, DNMT1, SCMH1, E2F1, HSP90AB1, FOXK1, CTCF, ZNF202, PDCD4, RPS3, CDC45, DGCR8, PCGF6, PSMD1, PSMD2, PSMD3, PSMD6, KDM5B, PSMD7, PPP2R1A, LDB1, UBE2I, RB1, PRKCD, CDK5, COBRA1, NCOA2, BPTF, PSME1, PSME2, UBC, PEBP1, CUX1, KDM6B, BTAF1, BCLAF1, TSPYL2, GFI1, TINF2, TNRC6A, ENO1, CEBPA, ZBTB7A, NACC1, MSH3, MSH2, SIRT5, CBY1, SIRT1, GPS2, SIRT3, DR1, PHB2, BAX, SETD8, VPS28, NFIC, and TBL1X); GO:0030163, protein catabolic process (IDE, USE1, CBX4, MYLIP, CDC16, CD2AP, ZNRF2, WWP2, CUL9, RABGEF1, RBCK1, RNF149, RNF34, AUP1, CDCA3, ANAPC1, PAN2, USP1, RELA, SKP2, UBR4, SOCS7, UBR2, UBE2J2, PSMA2, MIB1, PSMA1, UHRF1, KDM2A, PIAS4, TRIM33, FBXL8, UBR5, PSMA4, ASB1, FBXL5, RNF138, FBXL4, PIAS2, YME1L1, TNFAIP3, FBXL3, ASB6, RAD23B, RAD23A, NEDD8, UBA5, ANAPC11, CDC34, PSMA7, UBAC1, PSMB5, ARIH1, PSMB4, ARIH2, UBE2D2, PSMB1, FBXW5, FBXW4, FBXO43, STAMBPL1, RNF168, TRAF7, RNF167, FBXO9, HECTD1, FBXO7, HACE1, PCNP, CDC20, CDC26, AFG3L2, ATG3, ATE1, URM1, RNF6, PSMC5, PSMC4, VCP, UBA1, OTUB1, UBA2, UBA3, KIAA0368, UBE2G1, UBE2G2, BAP1, OS9, SENP6, FBXL19, FANCL, AKT1, USP19, LONP1, MGRN1, PSMD1, PSMD2, PSMD3, USP11, NSMCE2, USP10, PSMD6, PSMD7, USP14, UBE2A, UFD1L, DDB1, HERC5, HERC4, UBE2I, ERLIN1, HERC3, HERC2, WDR48, SENP3, PSME1, UBE2K, PSME2, UBE2M, UBC, DDB2, USP21, ADAM17, KLHL12, SIAH2, USP22, USP24, UBE2S, CLN6, USP7, CUEDC2, OTUD5, APH1A, USP3, UBE3B, C10ORF46, USP9X, USP4, EDEM3, C12ORF51, STUB1, EDEM1, MYCBP2, UBE2R2, SUMO2, RNF123, SQSTM1, MAP3K1, USP39, PPP2CB, USP36, FBXW11, USP33, TRIP12, BUB3, USP31, UBXN1, STAMBP, LRRC41, SPSB2, CBL, BIRC6, UBE2Q2, UBE2Q1, NCSTN, CCNB1, WSB1, PSMD14, HSP90B1, GMCL1, PSMD13, CUL4A, TCEB2, TBL1X, and BARD1); GO:0019941, modification-dependent protein catabolic process (CBX4, MYLIP, CDC16, CD2AP, ZNRF2, WWP2, CUL9, RABGEF1, RBCK1, RNF149, RNF34, AUP1, CDCA3, PAN2, ANAPC1, USP1, UBR4, SKP2, SOCS7, UBR2, UBE2J2, PSMA2, MIB1, PSMA1, UHRF1, KDM2A, PIAS4, TRIM33, FBXL8, UBR5, PSMA4, FBXL5, RNF138, FBXL4, PIAS2, TNFAIP3, FBXL3, ASB6, RAD23B, RAD23A, NEDD8, UBA5, ANAPC11, CDC34, PSMA7, UBAC1, PSMB5, ARIH1, PSMB4, ARIH2, UBE2D2, PSMB1, FBXW5, FBXW4, FBXO43, STAMBPL1, RNF168, TRAF7, RNF167, FBXO9, HECTD1, FBXO7, HACE1, PCNP, CDC20, CDC26, ATG3, ATE1, URM1, RNF6, PSMC5, PSMC4, VCP, UBA1, OTUB1, UBA2, UBA3, KIAA0368, UBE2G1, UBE2G2, BAP1, OS9, SENP6, FBXL19, FANCL, USP19, LONP1, MGRN1, PSMD1, PSMD2, PSMD3, USP11, NSMCE2, USP10, PSMD6, PSMD7, USP14, UBE2A, UFD1L, DDB1, HERC5, HERC4, UBE2I, ERLIN1, HERC3, HERC2, WDR48, SENP3, PSME1, UBE2K, PSME2, UBE2M, UBC, DDB2, USP21, KLHL12, SIAH2, USP22, USP24, UBE2S, USP7, CUEDC2, OTUD5, USP3, UBE3B, C10ORF46, USP9X, USP4, EDEM3, C12ORF51, STUB1, EDEM1, MYCBP2, UBE2R2, SUMO2, RNF123, SQSTM1, MAP3K1, USP39, PPP2CB, USP36, FBXW11, USP33, TRIP12, BUB3, USP31, UBXN1, STAMBP, LRRC41, CBL, SPSB2, BIRC6, UBE2Q2, UBE2Q1, CCNB1, WSB1, PSMD14, HSP90B1, GMCL1, PSMD13, CUL4A, TCEB2, TBL1X, and BARD1); GO:0043632, modification-dependent macromolecule catabolic process (CBX4, MYLIP, CDC16, CD2AP, ZNRF2, WWP2, CUL9, RABGEF1, RBCK1, RNF149, RNF34, AUP1, CDCA3, PAN2, ANAPC1, USP1, UBR4, SKP2, SOCS7, UBR2, UBE2J2, PSMA2, MIB1, PSMA1, UHRF1, KDM2A, PIAS4, TRIM33, FBXL8, UBR5, PSMA4, FBXL5, ASB1, RNF138, FBXL4, PIAS2, TNFAIP3, FBXL3, ASB6, RAD23B, RAD23A, NEDD8, UBA5, ANAPC11, CDC34, PSMA7, UBAC1, PSMB5, ARIH1, PSMB4, ARIH2, UBE2D2, PSMB1, FBXW5, FBXW4, FBXO43, STAMBPL1, RNF168, TRAF7, RNF167, FBXO9, HECTD1, FBXO7, HACE1, PCNP, CDC20, CDC26, ATG3, ATE1, URM1, RNF6, PSMC5, PSMC4, VCP, UBA1, OTUB1, UBA2, UBA3, KIAA0368, UBE2G1, UBE2G2, BAP1, OS9, SENP6, FBXL19, FANCL, USP19, LONP1, MGRN1, PSMD1, PSMD2, PSMD3, USP11, NSMCE2, USP10, PSMD6, PSMD7, USP14, UBE2A, UFDIL, DDB1, HERC5, HERC4, UBE2I, ERLIN1, HERC3, HERC2, WDR48, SENP3, PSME1, UBE2K, PSME2, UBE2M, UBC, DDB2, USP21, KLHL12, SIAH2, USP22, USP24, UBE2S, USP7, CUEDC2, OTUD5, USP3, UBE3B, C10ORF46, USP9X, USP4, EDEM3, C12ORF51, STUB1, EDEM1, MYCBP2, UBE2R2, SUMO2, RNF123, SQSTM1, MAP3K1, USP39, PPP2CB, USP36, FBXW11, USP33, TRIP12, BUB3, USP31, UBXN1, STAMBP, LRRC41, CBL, SPSB2, BIRC6, UBE2Q2, UBE2Q1, CCNB1, WSB1, PSMD14, HSP90B1, GMCL1, PSMD13, CUL4A, TCEB2, TBL1X, and BARD1); GO:0051603, proteolysis involved in cellular protein catabolic process (IDE, CBX4, MYLIP, CDC16, CD2AP, ZNRF2, WWP2, CUL9, RABGEF1, RBCK1, RNF149, RNF34, AUP1, CDCA3, PAN2, ANAPC1, USP1, RELA, UBR4, SKP2, SOCS7, UBR2, UBE2J2, PSMA2, MIB1, PSMA1, UHRF1, KDM2A, PIAS4, TRIM33, FBXL8, UBR5, PSMA4, ASB1, FBXL5, RNF138, FBXL4, PIAS2, TNFAIP3, FBXL3, ASB6, RAD23B, RAD23A, NEDD8, UBA5, ANAPC11, CDC34, PSMA7, UBAC1, PSMB5, ARIH1, PSMB4, ARIH2, UBE2D2, PSMB1, FBXW5, FBXW4, FBXO43, STAMBPL1, RNF168, TRAF7, RNF167, FBXO9, HECTD1, FBXO7, HACE1, PCNP, CDC20, CDC26, ATG3, ATE1, URM1, RNF6, PSMC5, PSMC4, VCP, UBA1, OTUB1, UBA2, UBA3, KIAA0368, UBE2G1, UBE2G2, BAP1, OS9, SENP6, FBXL19, FANCL, USP19, LONP1, MGRN1, PSMD1, PSMD2, PSMD3, USP11, NSMCE2, USP10, PSMD6, PSMD7, USP14, UBE2A, UFDIL, DDB1, HERC5, HERC4, UBE2I, ERLIN1, HERC3, HERC2, WDR48, SENP3, PSME1, UBE2K, PSME2, UBE2M, UBC, DDB2, USP21, ADAM17, KLHL12, SIAH2, USP22, USP24, UBE2S, USP7, CUEDC2, OTUD5, APH1A, USP3, UBE3B, C10ORF46, USP9X, USP4, EDEM3, C12ORF51, STUB1, EDEM1, MYCBP2, UBE2R2, SUMO2, RNF123, SQSTM1, MAP3K1, USP39, PPP2CB, USP36, FBXW11, USP33, TRIP12, BUB3, USP31, UBXN1, STAMBP, LRRC41, CBL, SPSB2, BIRC6, UBE2Q2, UBE2Q1, NCSTN, CCNB1, WSB1, PSMD14, HSP90B1, GMCL1, PSMD13, CUL4A, TCEB2, TBL1X, BARD1); and GO:0022403, cell cycle phase (ADCY3, PRC1, PKMYT1, RBM7, AURKB, CDC16, CD2AP, CDCA8, APP, RAD21, DDX11, INCENP, TARDBP, CDCA2, H2AFX, TUBG1, CCNA2, CDCA5, ASPM, CDCA3, ANAPC1, RAN, POLE, LIG3, SKP2, UBR2, ESPL1, TACC3, PPP1CB, WEE1, NCAPD3, NCAPD2, DCTN2, RCC2, TIMELESS, SPAG5, AKAP8, MAD2L2, DSCC1, MRE11A, KATNB1, ANAPC11, CDC34, RCC1, CCNG2, NIPBL, SAC3D1, NCAPG2, FBXO43, CLASP2, TCF3, HELLS, NUDC, SSSCA1, TAF1, MAP2K1, MKI67, PCNT, NUF2, CDC20, CDC26, RAD54L, ATM, HDAC3, CDKN1B, NOLC1, PLK1, ZNF318, SMC1A, ABL1, E2F1, MAD1L1, E2F4, RHOU, GTSE1, AKT1, CCNE1, SEH1L, PSMC3IP, RANBP1, DYNC1H1, FANCA, CDC7, ARHGEF2, CCNK, DSN1, CCNF, PAPD7, TPX2, NUSAP1, UBE2I, CDK6, RB1, RAD52, CDK4, CDK2, KLHDC3, RAD51, CCND1, CCND2, TOP3A, ADAM17, HAUS5, CAMK2G, USP9X, ZNF655, NCAPH, NCAPG, BCL2, NPAT, PAFAH1B1, GFI1, PPP3CA, BUB3, TRIP13, NFATC1, BOD1, TXNL4B, PDS5A, ILF3, MIS12, CDC25A, SMC4, CCNB1, PSMD13, CUL4A, GSPT1, SETD8, TXNL4A, and DNM2).

The candidate CRO for a particular gene can also be screened for "target site specificity," where the chosen fragment of the extra-coding RNA hybridizes exclusively with the targeted genomic site (gene locus) but not to any other genomic site (gene loci). Candidate transcripts can be screened with any useful method. In one example, candidate sequences of RNA oligonucleotides are assessed by using an algorithm with an genomic database (e.g., using a BLAST algorithm with the following parameters: −E: 10, −B: 100, filter: dust, −W: 8, −M: 1, —N: −1, −Q: 2, and −R: 1). In another example, the candidate sequences are manually assessed by Northern blot hybridization, as described in *Laboratory Techniques in Biochemistry and Molecular Biology: Hybridization with Nucleic Probes* (ed. P. C. van der Vliet, Elsevier Science Publishers B.V., 1993). Optionally, the genomic database methods and Northern blot hybridization methods are performed under stringent conditions. Results from these two exemplary approaches are shown in FIGS. 7A-7D and described herein.

Figure 4E:
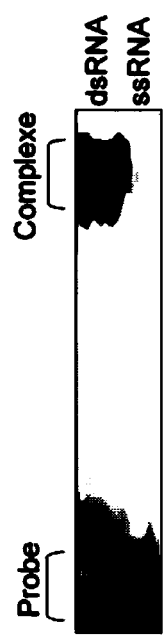
Figure 4F:
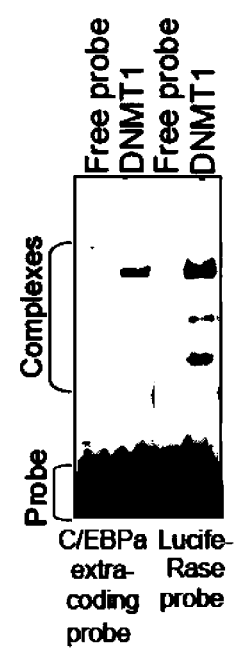

In addition, the candidate CRO for a particular gene can be screened for its ability to bind DNMTs. For example, acceptable binding includes that which results in an equal or higher affinity between the candidate CRO and one or more DNMTs, as compared to the affinity between a corresponding DNA oligonucleotide and the one or more DNMTs. Affinity can be assessed by any useful method. Exemplary methods include RNA/DNA electrophoretic mobility shift assays (such as shown in FIGS. 4D-4F) and measurement of direct quantitative binding of radiolabeled oligonucleotides to DNMTs (e.g., as described in Burgisser, J. Recept. Res. 4:357-369, 1984). In particular embodiments, the CRO has both target site specificity and the ability to bind DNMTs.

Different segments of an ecRNA can be tested to design the ssCRO, including those sequences upstream and downstream of the target gene and those sequences corresponding to coding and intronic sections. When the ecRNA includes a non-coding region, this region can be either upstream or downstream of the coding region of a gene. For example, the ecRNA can include a sequence that is downstream of the polyA addition site of the mRNA or in proximity to a promoter of the gene.

A CRO for a particular gene can be identified by any useful method. For example, the method includes one or more steps of identifying an ecRNA for a particular gene, identifying a sequence having percentage complementarity to the ecRNA, and determining one or more binding sites between the sequence having percentage complementarity and a DNMT (e.g., DNMT1 or any other described herein), where the presence of binding indicates that the sequence can reduce the activity of DNMT. Additional optional steps include determining the binding between the sequence of the CRO and the RNA or DNA for the gene; determining the methylation status of the target DNA, such as in one or more CpG islands; and determining the expression level of one or more genes. Furthermore, any of these steps can be performed for more than one gene and/or in a high-throughput manner. These methods can be implemented by any useful technique, e.g., a RNA electrophoretic mobility shift assay (REMSA); in vivo RNA immunoprecipitation (RIP) with ChIP-grade antibodies against DNA methyltransferase; RNA immunoprecipitation with RNA deep sequencing (RIP-Seq); 5', 3'-rapid amplification of the cDNA ends (RACE); microarray expression analysis (MEA); reduced representation bisulfite sequencing (RRBS); combined bisulfite restriction analysis (COBRA) assay; and combinations thereof.

Particular target genes can be identified in any useful manner. For example, ecRNAs corresponding to target genes can be down-regulated, and their effect on DNMT activity can be evaluated. Exemplary methods to down-regulate ecRNAs include using an RNAi agent, such as siRNA, dsRNA, miRNA, shRNA, or ptgsRNA. After confirming down-regulation of the targeted RNAs, expression levels of the corresponding mRNAs can be measured by qRT-PCR, and methylation pattern of the corresponding gene loci can be characterized by bisulfite sequencing. Further studies can include in vivo transplantation assays.

In one example, the sequence of ecRNA can be determined by RNA immunoprecipitation (RIP) followed by RNA deep sequencing (RIP-Seq). RIP is a technique used to detect the association of individual proteins with specific RNA molecules in the cellular context. Generally, cultured cells are treated with formaldehyde to generate protein-RNA crosslinks between interacting molecules. Following immunoprecipitation of a protein of interest and crosslink reversal, associated RNAs can be recovered, characterized, and quantitated by reverse transcriptase polymerase chain reaction (RT-PCR). Then, the immunoprecipitated RNAs will be subjected to RNA-Seq, as described in Mortazavi et al., Nat. Methods 5:621-628, 2008, hereby incorporated by reference. RNA-Seq is a robust technology for monitoring expression by direct sequencing the RNA molecules in a sample. Briefly, this methodology includes fragmentation of RNA to an average length of 200 nucleotides, conversion to cDNA by random priming, and synthesis of double-stranded cDNA (e.g., using the Just cDNA DoubleStranded cDNA Synthesis Kit from Agilent Technology). Then, the cDNA is converted into a molecular library for sequencing by addition of sequence adapters for each library (e.g., from Illumina®/Solexa), and the resulting 50-100 nucleotide reads are mapped onto the genome. RNA-Seq can be performed on RNAs immunoprecipitated by DNMT antibodies, using an IgG isotype antibody as a control. RIP-Seq can be performed in multiple human and/or murine cell lines that express or do not express a particular gene.

In another example, the methylation status of DNA can be determined by RBBS in a high-throughput manner, as described in Bock et al., Nat. Biotechnol. 28:1106-1114, 2010, incorporated herein by reference. Briefly, high-quality genomic DNA can be isolated from laboratory and primary cell lines employed for RIP-Seq and digested with the methylation-insensitive enzyme MspI. Pre-annealed Illumina®/Solexa sequence adapters containing 5'-methyl-cytosine can be ligated to the ends of size-selected fragments. Adapter-ligated fragments can be bisulfite-converted, amplified by PCR, and then size-selected and sequenced on the Illumina/Solexa 1G Genome Analyzer. Finally, MEA can be performed (e.g., using Affymetrix® GeneChip Human Gene 1.0 ST arrays) to determine expression levels.

The efficacy and/or toxicity of CROs can be determined by any useful method. Exemplary techniques include cellular assays performed in HL-60, U937, and/or K562 cell lines to determine one or more of changes in methylation within the genomic region corresponding to the CRO, changes in methylation in unrelated sites as a control for an off-target effect, changes in expression level of the particular target gene, and changes in expression of unrelated genes as a control for an off-target effect.

Methods of Preparing a Chimeric RNA Oligonucleotide

The CRO can be prepared by any useful method. Exemplary methods include chemical synthesis (e.g., using a solid support), in vitro transcription, digestion of long dsRNA by an RNase III family enzyme (e.g. Dicer, RNase III), and cell-based siRNA expression using plasmids, viral vectors, or PCR-derived expression cassette.

To incorporate modified nucleotides (e.g., cytidine analogs), the corresponding nucleoside can be converted into building blocks, which can be incorporated by step-wise addition to a growing chain of the oligonucleotide sequence. Alternatively, di-, tri-, or tetra-nucleotides having one or more modified nucleotides can be converted into building blocks and incorporated into the oligonucleotide sequence. Exemplary building blocks include cyanoethyl phosphoramidite or N-succinimide ester building blocks. Examples of phosphoramidite building blocks of mono-, di-, tri-, and tetra-nucleotides having one or more cytidine analogs include 5'-dimethoxytrityl(O-DMTr)-N4-dimethylformamidine-5,6-dihydro-5-aza-2'-deoxycytidine, 3'-[(2-cyanoethyl)-(N,N-diisopropyl)]-phosphoramidite (or 5-aza-5,6-dihydro-dC-CE phosphoramidite); 5'''-O-DMTr-2'-deoxy-5-aza-cytidine-3'-O-cyanoethyl-N,N-diisopropylphosphoramidite; and a dinucleotide including 5'-O-DMTr-2'-deoxyguanosine-3'-O-cyanoethyl-N,N-diisopropylphosphoramidite and 5'-O-DMTr-2'-deoxy-5-aza-cytidine-3'-O-cyanoethyl-N,N-diisopropylphosphoramidites. Additional cytidine analogs are described herein, and methods of making corresponding phosphoramidite building blocks are known.

Figure 6A:
FIGS. 6A-6D show exemplary gene-specific RNA oligonucleotides for reducing DNA methylation.
Figure 6B:
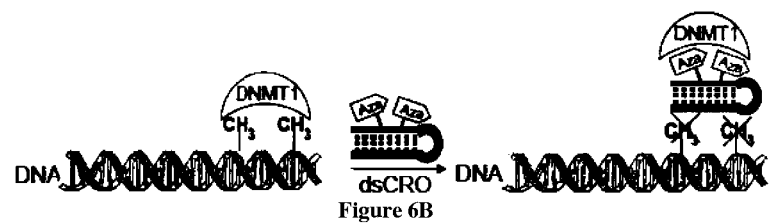
Figure 6C:
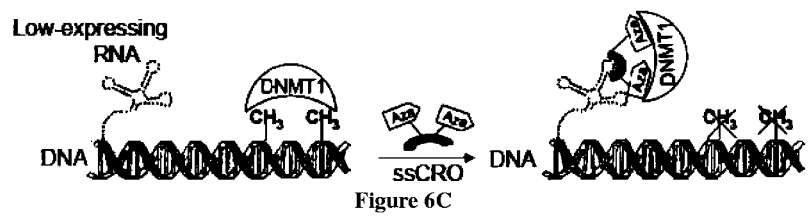
Figure 6D:
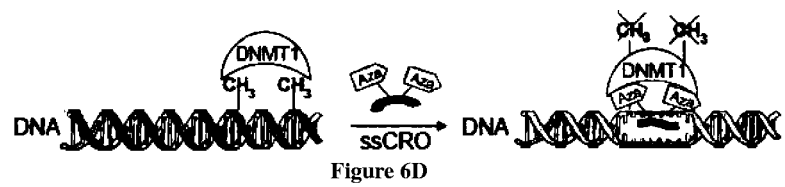

The CROs can be used in the form of double-stranded chimeric RNA oligonucleotide (dsCRO). As described herein, the RNA transcript binds DNMT1 and interferes with DNA methylation during transcription (FIG. 6A, left). In the absence of transcription, DNMT1 is not blocked and exerts enzymatic activity (FIG. 6A, right). For initial assays, dsCROs can be tested to determine its ability to sequester DNMT1 (see FIG. 6B). Exemplary dsCROs include those having stem loop-like structures. As compared to 5-aza-2'-deoxycytidine, these dsCROs will likely be more active and less toxic. Though these dsCROs lack gene-specificity, the results will provide preliminary binding data to DNMT. The following tests can include developing corresponding single-stranded CROs to determine gene-specific demethylating function.

Modifications to a RNA Oligonucleotide

The chimeric RNA oligonucleotide (CRO) can optionally include modifications, such as, e.g., to increase binding to a DNMT, increase stability, or increase cellular uptake. In particular, the CRO can include one or more cytidine analogs to further enhance binding to DNMT.

Cytidine Analogs

The chimeric RNA oligonucleotide of the invention can optionally include one or more modified cytidine nucleotides (or cytidine analogs). As described herein, cytidine analogs are useful in binding, and thus inactivating, DNMT.

Exemplary cytidine analogs includes 5-azacytidine and 5-aza-2'-deoxycytidine and further analogs thereof, including those having one of the following substitutions for the hydrogen of the 4-amino group of the cytosine ring: methyl, ethyl, 9-fluorenylmethyl, 9-(2-sulfo)fluorenylmethyl, 9-(2,7-dibromo)fluorenylmethyl, 17-tetrabenzo[a,c,g,i]fluorenylmethyl, 2-chloro-3-indenylmethyl, benz[f]inden-3-ylmethyl, 2,7-di-tert-[9-(10,10-dioxo-10,10,10,10-tetrahydrothioxanthyl)methyl, 1,1-dioxobenzo[b]thiophene-2-ylmethyl, 2,2,2-trichloroethyl, 2-trimethylsilylethyl, 2-phenylethyl, 1-(1-adamantyl)-1-methylethyl, 2-chloroethyl, 1,1-dimethyl-2-haloethyl, 1,1-dimethyl-2,2-dibromethyl, 1,1-dimethyl-2,2,2-trichlroethyl, 1-methyl-1-(4-biphenylyl)ethyl, 1-(3,5-di-tert-butylphenyl)-1-methylethyl, 2-(2'- and 4'-pyridyl)ethyl, 2,2-bis(4'-nitrophenyl)ethyl, N-(2-pivaloylamino)-1,1-dimethylethyl, 2-[(2-nitrophenyl)dithio]-1-phenylethyl, 2-(N,N-dicyclohexylcarboxamido)ethyl, t-butyl, 1-adamantyl, 2-adamantyl, vinyl, allyl, 1-isopropylallyl, cinnayl, 4-nitrocinnamyl, 3-(3'-pyridyl)prop-2-enyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl, 2-methylthioethyl, 2-methylsulfonylethyl, 2-p-toluenesulfonyl)ethyl, [2-(1,3-dithianyl)]methyl, 4-methylthiphenyl, 2,4-dimethylthiphenyl, 2-phosphonioethyl, 1-methyl-1-(triphenylphosphonio)ethyl, 1,1-dimethyl-2-cyanoethyl, 2-dansylethyl, 4-phenylacetoxybenzyl, 4-azidobenzyl, 4-azidomethoxybenzyl, m-chloro-p-acyloxybenzyl, p-(dihydroxyboryl)benzyl, 5-benzisoxazolylmethyl, 2-(trifluoroethyl)-6-chromonylmethyl, m-nitrophenyl, 3,5-dimethoxybenzyl, 1-methyl-1-(3,5-dimethoxyphenyl)ethyl, .alpha.-methylnitropiperonyl, o-nitrophenyl, 3,4-dimethoxy-6-nitrobenzyl, phenyl(o-nitrophenyl)ethyl, 2-(2-nitrophenyl)ethyl, 6-nitroveratryl, 4-methoxyphenacyl, 3',5'-dimethoxybenzoin, t-amyl, S-benzylthio, butynyl, p-cyanobenzyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)henzyl, 1,1-dimethyl-3-(N,N-dimethycarboxamido)propyl, 1,1-dimethylpropynyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(p-phenylazophenyl)ethyl, 1-methyl-1-phenylethyl, 1-methyl-1-(4'-pyridyl)ethyl, phenyl, p-(phenylazo)benzyl, 2,4,6-tri-t-butylphenyl, 4-(trimethylammonium)benzyl, 2,4,6-trimethylbenzyl, a urea (e.g., a urea with phenothiazinyl-(10)-carbonyl, N'-p-toluenesulfonylaminocarbonyl, and N'-phenylaminothiocarbonyl), and an amide (e.g., formamide, acetamide, phenoxyacetamide, trichloroacetamide, trifluoroacetamide, phenyacetamide, 3-phenylpropamide, pent-4-enamide, o-nitrophenylacetamide, o-nitrophenoxyacetamide, 3-(o-nitrophenyl)propanamide, 2-methyl-2-(o-nitrophenoxy)propanamide, 3-methyl-3-nitrobutanamide, o-nitrocinnamide, 3-(4-t-butyl-2,6-dinitrophenyl)-2,2-dimethylpropanamide, o-(benzoyloxymethyl)benzamide, 2-[(t-butyldiphenylsiloxy)methyl)methyl]benzamide, 3-(3',6'-dioxo-2',4',5'-trimethylcyclohexa-1',4'-diene)-3,3-dimethylpropionamide, o-hydroxy-trans-cinnamide, acetoacetamide, p-toluenesulfonamide, and benzesulfonamide); or those having one of the following substitutions for the 4-amino group of the cytosine ring: 4-O-methoxy and 4-S-methylsulfanyl. In some embodiments, the cytidine analog is further conjugated to a guanosine nucleotide (e.g., 2'-deoxyguanosine), such as for 5-aza-2'-deoxycytidine-phosphodiester linkage-guanosine, 5-aza-2'-deoxycytidine-phosphodiester linkage-2'-deoxy-guanosine, guanosine-phosphodiester linkage-5-aza-2'-deoxycytidine, and 2'-deoxy-guanosine-phosphodiester linkage-5-aza-2'-deoxycytidine. Additional modifications to nucleotides are described herein.

Further Modifications to the Chimeric RNA Oligonucleotide

Modifications to the CRO include modified nucleotides having one or more modifications to the chemical structure of the base, sugar, and/or backbone, including the phosphodiester linker.

Non-limiting modified bases include those having 4- and/or 5-position pyrimidine modifications, 8-position purine modifications, and modifications at cytosine exocyclic amines. Additional modified bases refer to nucleotide bases such as, for example, adenine, guanine, cytosine, thymine, uracil, xanthine, inosine, and queuosine that have been modified by the replacement or addition of one or more atoms or groups. Further examples of modified bases include bases that are alkylated (e.g., as in O- and N-alkylated purines and pyrimidines), halogenated, thiolated, aminated, amidated, addition or removal of an aza group, or acetylated bases, individually or in combination. Exemplary modified bases include 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, 7-deazaadenosine, 7-deazaxanthine, 7-deazaguanine, 6-azouridine, 6-azocytidine, 6-azothymidine, 5-methyl-2-thiouridine, 2-thiouridine, 4-thiouridine, 2-thiocytidine, dihydrouridine, pseudouridine, queuosine, archaeosine, N6-methyladenosine, 8-oxo-N6-methyladenine, 5-methylcarbonylmethyluridine, uridine 5-oxyacetic acid, pyridine-4-one, pyridine-2-one, diaminopurine, N4,N4-ethanocytosin, N6,N6-ethano-2,6-diaminopurine, 5-(C3-C6)-alkynylcytosine, 5-fluorouracil, 5-bromouracil, pseudoisocytosine, 2-hydroxy-5-methyl-4-triazolopyridine, isocytosine, isoguanine, 8-substituted adenines and guanines, 5-substituted uracils and thymines, azapyrimidines, carboxyhydroxyalkyl nucleotides, carboxyalkylaminoalkyl nucleotides, alkylcarbonylalkylated nucleotides, and universal bases (e.g., pyrrole, diazole, triazole, pyrene, pyridyloxazole, and pyrenylmethylglycerol derivatives, such as 3-nitropyrrole or 5-nitroindole).

Exemplary modified sugars include 2-position sugar modifications, in which the 2-OH is replaced by a group such as an H, OR, R, halo (e.g., F), SH, SR, $NH_2$, NHR, $NR_2$, or CN, wherein R is an alkyl moiety. Modified sugars also include, e.g., non-ribose sugars, such as mannose, arabinose, glucopyranose, galactopyranose, 4-thioribose, and other sugars, heterocycles, or carbocycles.

In some embodiments, the CRO includes a phosphorodiester linkage, such as via 2'-ribose, as in the natural sugar phosphorodiester backbone in RNA. In other embodiments, to enhance the resistance to nuclease degradation in vivo, the natural phosphorodiester linker —O—P(=O)(O)—O—$CH_2$— can be modified to be a phosphorothioate linker —O—P(=O)($S^-$)—O—$CH_2$—, a boranophosphate linker, or a methylphosphonate linker. Phosphorothiate linkers can be implemented using standard phosphoramidite protocols and substituting a bis(O,O-diisopropoxy phosphinothioyl) disulfide (S-tetra) for iodine during the oxidation step (see, e.g., Zon and Stec. "Phosphorothioate Analogues" in *Oligonucleotides and Their Analogs: A Practical Approach* (ed. F. Eckstein, IRL Press, pp. 87-108, 1991); Zon, *High Performance Liquid Chromatography in Biotechnology* (ed. W. S. Hancock, Wiley, New York, Ch. 14, pp. 310-397, 1990); Stec et al., Tetrahed. Lett. 34:5317-5320, 1993; Iyer et al., J. Org. Chem. 55:4693-4699, 1990). Other exemplary linkers include phosphorodithioates, phosphotriesters, aminoalkylphosphotriesters, alkyl phosphonates (e.g., 3'-alkylene phosphonate), chiral phosphonates, phosphinates, phosphoramidates (e.g., 3'-amino phosphoramidate), aminoalkylphosphoramidates, thionophosphoramidates, thionoalkylphosphonates, and thionoalkylphosphotriesters. Other modifications to the backbone include those replacing the phosphorous atom with short chain alkyl or cycloalkyl internucleoside linkages, mixed heteroatom and alkyl or cycloalkyl internucleoside linkages, or one or more short chain heteroatomic or heterocyclic internucleoside linkages (e.g., morpholinio linkages; siloxane backbones; sulfide, sulfoxide and sulphone backbones; formacetyl and thioformacetyl backbones; methylene formacetyl and thioformacetyl backbones; alkene containing backbones; sulphamate backbones; methyleneimino and methylenehydrazino backbones; sulfonate and sulfonamide backbones; amide backbones; and others having mixed N, O, S and $CH_2$ component parts).

In other embodiments, the natural sugar phosphorodiester backbone can be replaced with a protein nucleotide (PNA) backbone having repeating N-(2-aminoethyl)-glycine units linked by peptide bonds. Other types of modifications for oligonucleotides designed to be more resistant to nuclease degradation are described U.S. Pat. Nos. 6,900,540 and 6,900,301, incorporated herein by reference.

Therapeutic Agents

The CRO can include any useful therapeutic agent. Any of the therapeutic agents described below may be used in the compounds of the invention. Exemplary therapeutic agents for use in a CRO are demethylating agents (e.g. cytidine analogs, as described herein), DNA and/or RNA polymerase inhibitors (e.g., a synthetic nucleoside that resembles cytidine, such as cytarabine for the treatment of acute myelocytic leukemia; fludarabine for the treatment of hematologic malignancies by S-phase specific inhibition of multiple DNA polymerases, including DNA primase and DNA ligase I; gemcitabine; cladribine; and clofarabine); thymidylate synthase inhibitors (e.g., 5-fluorouracil (5FU), floxuridine (FUDR), capecitabine, tegafur, and cannofur); immunosuppressants (e.g., azathioprine); and other nucleoside analogs, such as thiopurines (e.g., thioguanine and mercaptopurine) and adenosine analogs (e.g., pentostatin, which is an adenosine deaminase inhibitor, and cladribine, which is a DNA polymerase inhibitor).

Demethylating Agents

The CRO can include one or more demethylating agents, including nucleoside-based agent (e.g., a cytidine analog). Exemplary demethylating agents include cytidine analogs, such as 5-azacytidine (or azacitidine), 5-aza-5,6-dihydrocytosine, 5-aza-2'-deoxycytidine (or decitabine), beta-L-5-azacytidine, 2'-deoxy-beta-L-5-azacytidine, 2'-deoxy-N4-[2-(4-nitrophenyl)ethoxycarbonyl]-5-azacytidine (or N4-NPEOC-5-CdR), 5-fluorocytidine, 1-β-D-arabinofuranosil-5-azacytosine (or fazarabine), and 1-β-D-ribofuranosyl-2(1H)-pyrimidinone (or zebularine); and non-nucleoside analogs, such as derivatives of 4-aminobenzoic acid (e.g., procaine), epigallocatechin-3-gallate (EGCG), N-phthalyl-L-tryptophan (or RG108), and (1E,6E)-1,7-bis(4-hydroxy-3-methoxyphenyl)-1,6-heptadiene-3,5-dione (curcumin).

Labels

A label can be linked to the chimeric RNA oligonucleotide to allow for diagnostic and/or therapeutic treatment. Examples of labels include detectable labels, such as an isotope, a radioimaging agent, a marker, a tracer, a fluorescent label (e.g., rhodamine), and a reporter molecule (e.g., biotin).

Examples of radioimaging agents emitting radiation (detectable radio-labels) that may be suitable are exemplified by indium-111, technitium-99, or low dose iodine-131. Detectable labels, or markers, for use in the present invention may be a radiolabel, a fluorescent label, a nuclear magnetic resonance active label, a luminescent label, a chromophore label, a positron emitting isotope for PET scanner, a chemiluminescence label, or an enzymatic label. Fluorescent labels include but are not limited to, green fluorescent protein (GFP), fluorescein, and rhodamine. Chemiluminescence labels include but are not limited to, luciferase and β-galactosidase. Enzymatic labels include but are not limited to peroxidase and phosphatase. A histamine tag may also be a detectable label. For example, conjugates may comprise a carrier moiety and an antibody moiety (antibody or antibody fragment) and may further comprise a label. The label may be for example a medical isotope, such as for example and without limitation, technetium-99, iodine-123 and -131, thallium-201, gallium-67, fluorine-18, indium-111, etc.

Formation of a Complex with a Carrier

For delivery to the target gene, the chimeric RNA oligonucleotide of the invention can covalently or non-covalently bind a carrier to form a complex. The carrier can be used to alter biodistribution after delivery, to enhance uptake, to increase half-life or stability of the CRO (e.g., improve nuclease resistance), and/or to increase targeting to a particular cell or tissue type.

Exemplary carriers include a condensing agent (e.g., an agent capable of attracting or binding a nucleic acid through ionic or electrostatic interactions); a fusogenic agent (e.g., an agent capable of fusing and/or being transported through a cell membrane); a protein to target a particular cell or tissue type (e.g., thyrotropin, melanotropin, lectin, glycoprotein, surfactant protein A, or any other protein); a lipid; a lipopolysaccharide; a lipid micelle or a liposome (e.g., formed from phospholipids, such as phosphotidylcholine, fatty acids, glycolipids, ceramides, glycerides, cholesterols, or any combination thereof), a nanoparticle (e.g., silica, lipid, carbohydrate, or other pharmaceutically-acceptable polymer nanoparticle); a polyplex formed from cationic polymers and an anionic agent (e.g., a CRO), where exemplary cationic polymers include polyamines (e.g., polylysine, polyarginine, polyamidoamine, and polyethylene imine); cholesterol; a dendrimer (e.g., a polyamidoamine (PAMAM) dendrimer); a serum protein (e.g., human serum albumin (HSA) or low-density lipoprotein (LDL)); a carbohydrate (e.g., dextran, pullulan, chitin, chitosan, inulin, cyclodextrin, or hyaluronic acid); a lipid; a synthetic polymer, (e.g., polylysine (PLL), polyethylenimine, poly-L-aspartic acid, poly-L-glutamic acid, styrene-maleic acid anhydride copolymer, poly(L-lactide-co-glycolic) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymer, pseudopeptide-polyamine, peptidomimetic polyamine, or polyamine); a cationic moiety (e.g., cationic lipid, cationic porphyrin, quaternary salt of a polyamine, or alpha helical peptide); a multivalent sugar (e.g., multivalent lactose, multivalent galactose, N-acetyl-galactosamine, N-acetyl-glucosamine, multivalent mannose, or multivalent fucose); a vitamin (e.g., vitamin A, vitamin E, vitamin K, vitamin B, folic acid, vitamin B12, riboflavin, biotin, or pyridoxal); a cofactor; or a drug to disrupt cellular cytoskeleton to increase uptake (e.g., taxon, vincristine, vinblastine, cytochalasin, nocodazole, japlakinolide, latrunculin A, phalloidin, swinholide A, indanocine, or myoservin).

Diseases and Conditions

The CROs of the invention can be used to treat a variety of diseases and conditions involving aberrant DNMT activity. In particular, beneficial treatments of cancer and imprinting disorders include use of the CROs to reduce DNMT activity in a gene-specific manner.

Cancer Therapy

The CROs of the invention may be used to treat any disease related to aberrant DNMT activity, such as cancer. In particular, the CROs of the invention can be used to treat cancers having aberrant methylation of specific genes related with cancer progression. Exemplary cancers include those related to C/EBPa expression, such as myelodysplastic syndrome (e.g., refractory anemia, refractory anemia with ringed sideroblasts, refractory anemia with excess blasts, refractory anemia with excess blasts in transformation, refractory cytopenia with multilineage dysplasia, myelodysplastic syndrome associated with an isolated del(5q) chromosome abnormality, and a myeloproliferative neoplasm), leukemia (e.g., acute myeloid leukemia), head and neck cancer, liver cancer (e.g., hepatoma and hepatocellular carcinoma), lung cancer (e.g., adenocarcinoma and non-small cell lung cancer), prostate cancer (e.g., adenocarcinoma), and skin cancer (e.g., squamous cell carcinoma); those related to SPI1, such as acute myeloid leukemia, T-cell lymphoma, and chronic lymphocytic leukemia-like disease; those related to RXRA, such as non-small cell lung cancer (NSCLC); and those related to RARB such as lung cancer (e.g., small cell lung cancer (SCLC) and non-small cell lung cancer (NSCLC)), head and neck cancer, breast cancer, prostate cancer, glioblastoma, and leukemia.

Other exemplary methylated genes and related cancers include RB1 in retinoblastoma (see Stirzaker et al., Cancer Res. 57:2229-2237, 1997); CDKN2A (INK 4A and ARF transcript) in lung and colon cancer (see Herman et al., Cancer Res. 55:4525-4530, 1995; and Robertson et al., Mol Cell Biol. 18:6457-6473, 1998); CDH1 in breast cancer, gastric cancer, thyroid cancer, leukemia, and liver cancer (see Graff et al., Cancer Res. 55:5195-5199, 1995); CDH13 in lung cancer, ovarian cancer, and pancreatic cancer (see Toyooka et al., Cancer Res. 61:4556-4560, 2001); TIMP3 in brain cancer and kidney cancer (see Bachman et al., Cancer Res. 59:798-802, 1999); VHL in kidney cancer (see Herman et al., Proc. Natl Acad. Sci. USA 91:9700-9704, 1994); MLH in colon cancer, endometrial cancer, and gastric cancer (see Kane et al., Cancer Res. 57:808-811, 1997); MGMT in brain cancer, colon cancer, lung cancer, and breast cancer (see Qian et al., Cancer Res. 57:3672-3677, 1997); BRCA1 in breast cancer and ovarian cancer (see Dobrovic et al., Cancer Res. 57:3347-3350, 1997); GSTP1 in prostate cancer, liver cancer, colon cancer, breast cancer, and kidney cancer (see Lee et al., Proc. Natl Acad. Sci. USA 91:11733-11737, 1994); SMARCA3 in colon cancer and gastric cancer (see Moinova et al., Proc. Natl Acad. Sci. USA 99:4562-4567, 2002); RASSF1 in lung cancer, liver cancer, and brain cancer (see Dammann et al., Nat. Genet. 25:315-319, 2000); SOCS1 in liver cancer, colon cancer, and multiple myeloma (see Yoshikawa et al., Nat. Genet. 28:29-35, 2001); ESR1 in colon cancer, breast estrogen receptor-negative cancer, lung cancer, and leukemia (see Issa et al, Nat. Genet. 7:536-540, 1994), DAPK1 in lymphoma (see Katzenellenbogen et al., Blood 93:4347-4353, 1999). Additional cancers include those associated with any gene described herein (e.g., a gene in cluster C).

Genetic Disorders

The CROs of the invention can be used to treat genetic disorders that arise from aberrant DNA methylation, such as imprinting disorders related to uniparental disomy. The potency and the gene specificity of the CRO can be used to correct aberrant gain of DNA methylation within a specific gene locus and/or to restore the normal expression of an imprinted parental allele, as the expressed allele is mutated or deleted for a particular locus.

Exemplary genetic disorders include imprinting disorders, such as Beckwith-Wiedemann Syndrome (BWS), Prader-Willi Syndrome (PWS), Angelman Syndrome (AS), Albright hereditary osteodystrophy (AHO), pseudohypoparathyroidism type 1A (PHP-IA), and pseudohypoparathyroidism type 1B (PHP-IB); disorders associated with loss of imprinting (LOI), which is considered the most abundant and most precocious alteration in cancer, such as LOI in IGF2/H19 for Wilms' tumor; and repeat instability diseases, where the expansion of trinucleotide (TNR) repeats leads to silencing of the associated genes, such as in Fragile X syndrome and myotonic dystrophy.

Administration and Dosage

The present invention also features pharmaceutical compositions that contain a therapeutically effective amount of a CRO of the invention. The composition can be formulated for use in a variety of drug delivery systems. One or more physiologically acceptable excipients or carriers can also be included in the composition for proper formulation. Suitable formulations for use in the present invention are found in *Remington's Pharmaceutical Sciences* (Mack Publishing Company, Philadelphia, Pa., 17th ed., 1985). For a brief review of methods for drug delivery, see, e.g., Langer, Science 249:1527-1533, 1990.

The pharmaceutical compositions are intended for parenteral, intranasal, topical, oral, or local administration, such as by a transdermal means, for prophylactic and/or therapeutic treatment. The pharmaceutical compositions can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Sustained release administration is also specifically included in the invention, by such means as depot injections or erodible implants or components. Thus, the invention provides compositions for parenteral administration that include the above mention agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

The compositions containing an effective amount can be administered for prophylactic or therapeutic treatments. In prophylactic applications, compositions can be administered to a subject with a clinically determined predisposition or increased susceptibility to cancer, or any disease described herein. Compositions of the invention can be administered to the subject (e.g., a human) in an amount sufficient to delay, reduce, or preferably prevent the onset of clinical disease. In therapeutic applications, compositions are administered to a subject (e.g., a human) already suffering from disease (e.g., cancer, such as leukemia or a myelodysplastic syndrome) in an amount sufficient to cure or at least partially arrest the symptoms of the condition and its complications. An amount adequate to accomplish this purpose is defined as a "therapeutically effective amount," an amount of a compound sufficient to substantially improve some symptom associated with a disease or a medical condition. For example, in the treatment of a cancer (e.g., those described herein), an agent or compound that decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

Amounts effective for this use may depend on the severity of the disease or condition and the weight and general state of the subject, but generally range from about 0.05 µg to about 1000 μg (e.g., 0.5-100 μg) of an equivalent amount of the agent per dose per subject. Suitable regimes for initial administration and booster administrations are typified by an initial administration followed by repeated doses at one or more hourly, daily, weekly, or monthly intervals by a subsequent administration. The total effective amount of an agent present in the compositions of the invention can be administered to a mammal as a single dose, either as a bolus or by infusion over a relatively short period of time, or can be administered using a fractionated treatment protocol, in which multiple doses are administered over a more prolonged period of time (e.g., a dose every 4-6 hours, 8-12 hours 14-16 hours, 18-24 hours, every 2-4 days, every 1-2 weeks, and once a month). Alternatively, continuous intravenous infusions sufficient to maintain therapeutically effective concentrations in the blood are contemplated.

The therapeutically effective amount of one or more agents present within the compositions of the invention and used in the methods of this invention applied to mammals (e.g., humans) can be determined by the ordinarily-skilled artisan with consideration of individual differences in age, weight, and the condition of the mammal. Single or multiple administrations of the compositions of the invention including an effective amount can be carried out with dose levels and pattern being selected by the treating physician. The dose and administration schedule can be determined and adjusted based on the severity of the disease or condition in the subject, which may be monitored throughout the course of treatment according to the methods commonly practiced by clinicians or those described herein.

The compounds of the present invention may be used in combination with either conventional methods of treatment or therapy or may be used separately from conventional methods of treatment or therapy.

When the compounds of this invention are administered in combination therapies with other agents, they may be administered sequentially or concurrently to an individual. Alternatively, pharmaceutical compositions according to the present invention may be comprised of a combination of a compound of the present invention in association with a pharmaceutically acceptable excipient, as described herein, and another therapeutic or prophylactic agent known in the art.

In particular, combination therapies include a CRO and a histone deacetylase (HDAC) inhibitor to further modulate transcription of genes, e.g., to promote the transcription of genes previously silenced by hypermethylation and acetylation of histones. Exemplary HDAC inhibitors include hydroxamic acids (e.g., trichostatin A (ISA), vorinostat (SAHA), belinostat (PXD101), ((E)-N-hydroxy-3-[4-[[2-hydroxyethyl-[2-(1H-indol-3-yl)ethyl]amino]methyl]phenyl]prop-2-enamide (LAQ824), panobinostat (LBH589), subcroylanilide hydroxamic acid (SAHA), oxamflatin, scriptaid, suberic bishydroxamic acid (SBHA), m-carboxycinnamic acid bishydroxamic acid (CBHA), or pyroxamide); cyclic peptides (e.g., trapoxin A, apidicin, TPX-HA, or depsipeptide (FR901228)); benzamides (e.g., entinostat (MS-275), N-acetyldinaline (CI994), or mocetinostat (MGCD0103); electrophilic ketones (e.g., trifluoromethyl ketones or alpha-ketoamides, see Frey et al., Bioorg. Med. Chem. Lett. 12:3443-3447, 2002, and U.S. Pat. No. 6,511, 990, incorporated herein by reference); and fatty acids (e.g., valproic acid, arginine butyrate, butyric acid, or phenylbutyrate).

EXAMPLES

Experimental Methods

The experimental methods described herein are used to obtain the results discussed in the brief description of the figures and the examples described herein, unless otherwise noted.

Cell culture: All cell lines were obtained from ATCC and grown in glutamine containing medium, at 37° C. in a humidified atmosphere with 5% $CO_2$.

RNA isolation and Northern Blot Analysis: Total RNA isolation, electrophoresis, transfer, and hybridization were carried out as described in Maniati et al., Molecular cloning: A Laboratory Manual, Cold Spring Harbor Laboratory Press, 1982). Cytoplasmic RNA was isolated with the Paris kit (Ambion) according to the manufacturer's recommendations. Nuclear RNAs were prepared according to Blobel, et al., Science 154:1662-1665, 1966, with minor modifications. Briefly, equal amounts of viable cells (~50 million) were washed with ice-cold PBS supplemented with 5 mM vanadyl complex, 1 mM PMSF and resuspended in the ice-cold lysis buffer: 1× Buffer A (10 mM HEPES-NaOH pH 7.6; 25 mM KCl; 0.15 mM spermine; 0.5 mM spermidine; 1 mM EDTA; 2 mM Na butyrate); 1.25 M sucrose; 10% glycerol; 5 mg/mL BSA; 0.5% NP-40; freshly supplemented with protease inhibitors (2 mM leupeptin, add as ×400; 2 mM pepstatin, add as ×400; 100 mM benzamidine, add as ×400; a protease inhibitor cocktail (Roche Applied Science, Cat. No. 1836153), 1 tablet with 375 μL $H_2O$, add as ×100; 100 mM PMSF, add as ×100); 2 mM vanadyl complex (New England Biolabs); and 20 units/mL RNase inhibitor (RNAguard; Amersham Biosciences). Samples were incubated at 0° C. for ~10 minutes and passed through a Dounce homogenizer. The pelleted nuclei were resuspended in 0.5 ml of lysis buffer and diluted with 2.25 mL of Dilution Buffer (2.13 mL of "Cushion" buffer with 0.12 mL of 0.1 g/mL BSA), freshly supplemented with protease inhibitors, overlaid onto 2 mL "cushions" (200 mL "Cushion" buffer consists of 15 mL dd$H_2O$; 15 mL 20× Buffer A; 30 mL glycerol; 240 mL 2.5 M sucrose; freshly supplemented with protease inhibitors) into one SW 55 Ti tube, and centrifuged at 24,400 rpm (60 minutes, 4° C.). The pelleted nuclei were resuspended in 1 mL Storage buffer (1.75 mL ddH2O; 2 mL glycerol; 0.2 mL 20× Buffer A), freshly supplemented with protease inhibitors. Nuclear RNAs were extracted as described in Maniatis et al., 1982. All total, cytoplasmic, and nuclear RNA samples used in this study were treated with DNase I (10 U of DNase I per 3 μg of total RNA; 37° C. for one hour; in the presence of RNase inhibitor). After DNase I treatment, RNA samples were extracted with acidic phenol (pH 4.3) to eliminate any remaining traces of DNA. Polyadenylated and non-polyadenylated RNA fractions were selected with the MicroPoly (A) Purist™ purification kit (Ambion). cDNA syntheses were performed with Random Primers (Invitrogen) with Transcriptor Reverse Transcriptase (Roche Applied Science) according to the manufacturer's recommendation. cDNA was purified with a High Pure PCR Product Purification Kit (Roche Applied Science). The sequences of various Northern Blotting probes were as follows:

C/EBPα mRNA:

(SEQ ID NO: 10)
5'-CCGCTCCTCCACGCCTGTCCTTAGAAAGGGGTGGAAACATAGGGACT

TGGGGCTTGGAACCTAAGGTTGTTCCCCTAGTTCTACATGAAGGTGGAGG

GTCTCTAGTTCCACGCCTCTCCCACCTCCCTCCGCACACACCCCACCCCA

-continued

```
GCCTGCTATAGGCTGGGCTTCCCCTTGGGGCGGAACTCACTGCGATGGGG

GTCACCAGGTGACCAGTGGGAGCCCCCACCCCGAGTCACACCAGAAAGCT

AGGTCGTGGGTCAGCTCTGAGGATGTATACCCCTGGTGGGAGAGGGAGAC

CTAGAGATCTGGCTGTGGGGC-3';
```
and ecRNA:
(SEQ ID NO: 11)
```
5'-GTCACATTTGTAAATAATACAGCATTTTCCCTGGCGGCAATCCTGAC

TTTCATGAGCTCTCCATCCATCCTGAGCCCCTCTTACCCTAAGGGGTGA

CTTACTTCCCCCAGGCAAGACAAATAAATAGCAGAGGACAAGGCTCCAAA

TGGAGTATGTCCAGAGCCTGAAGGCAGTCTCTTGGGGTCAGGGGAGGGGG

CTGAAGGGGTTACTGGGCTGAGGCCTTGGCGAGGCTTCTTATCTGCCCCG

GGGAGGAGGAGAGGGAGTCCTCTGCCTGAGGGGTAGGCCTGGCTAAGCAG

CCCTAGGCTCAAGGAGCCCTTTGTGCAGACTTCCTTGCAAATCACCTACA

GCTGCAGCCCTGGCCACTCACACACCGCAGCTCCAGATCCAGCAGGA

CCCTCGGCCAGCAGGAAGAGGCCTCCAGTGGTAGGACCCTCCAACCCTCT

CCTCTTTCCCTAGACCATGTGGCTACACCCTACC-3'.
``` qRT-PCR: Sybr green reactions were performed using iQ Sybr Green supermix (Biorad, Hercules, Calif.) using the following parameters: 95° C. (10 min.), 40 cycles of 95° C. (15 sec.) and 60° C. (1 min.), and 72° C. (1 min.). TaqMan analysis was performed using Hotstart Probe One-step qRT-PCR master mix (USB) at the following conditions: 50° C. (10 min.), 95° C. (2 min.), and then 40 cycles of 95° C. (15 sec.) and 60° C. (60 sec.). qRT PCR primers were located in the coding region for the mRNA (black double headed arrow) and after the polyA signal for the ecRNA (white double headed arrow) (FIG. 1A). The sequences of primers used for TaqMan real time PCR were as follows: human C/EBPa: Forward 5'-TCG GTG GACAAG AAC AG-3' (SEQ ID NO:18), Reverse 5'-GCA GGC GGT CAT TG-3' (SEQ ID NO:19), and Taqman Probe 5'-ACA AGGCCA AGC AGC GC-3' (SEQ ID NO:20); ecRNA: Forward 5'-GGT TGT CTG TGG GCC AGG TCA-3'(SEQ ID NO:21), Reverse 5'-AGA GCT CAT GAA AGT CAG GAT TG-3' (SEQ ID NO:22), and Taqman Probe 5'-AAT AAT ACAGCA TTT TCC CTG GCG G-3'(SEQ ID NO:23); human C/EBPγ: Forward: 5'-GGC TAG AGG AGC AGGTAC AT-3' (SEQ ID NO:24), Reverse: 5'-GCC TGG GTA TGG ATA ACA CTA-3' (SEQ ID NO:25), and Taqman Probe: 5'-CGACAC CAC TCA TGT CAA TGG CTG-3' (SEQ ID NO:26); human TP73: ABI Cat. #Hs01060631_m1; 18S rRNA: ABI Cat. #4310893E; and human 5S rRNA: ABI Cat. #Hs02385257_g1. The sequences of primers used for real-time RT PCR (Sybr) were as follows: human C/EBPa: Forward: 5'-CCG CTC CTC-CAC GCC TGT CCT TAG-3' (SEQ ID NO:27) and Reverse: 5'-GCC CCA CAG CCA GAT CTC TAG GTC-3' (SEQ ID NO:28); ecRNA: Forward: 5'-TCA TGA GCT CTC CAT CCA TCC TGA-3'(SEQ ID NO:29) and Reverse: 5'-CTG GCCGAG GGT CCT GCT GGA ATC-3' (SEQ ID NO:30); and β-ACTIN Promega Cat. #G5740.

Primer extension and 5',3' RACE: cDNA from the HL-60 cell line was synthesized as described above and run in alkaline condition (Sambrook et al., Molecular Cloning: A Laboratory Manual, 3rd ed., (Cold Spring Harbor Laboratory Press, 2001). Southern blot transfer and hybridization with oligo AL16 were performed as previously reported (Sambrook et al, 2001). The sequences of primers used for 5' RACE were as follows: R4—5'-AGA GGC GCG CTT GCC TAC AGG TGA-3' (SEQ ID NO:12), R6—5'CTC GCC ACT GGC GCT GAG GCC TGA-3' (SEQ ID NO:13), and R8—5'-GAG TCT TGG GAG CCC TCAAGT GTC T-3' (SEQ ID NO:14). The sequences of primers used for 3' RACE were as follows: AL21—5'-GTC ACA TTT GTA AAT AAT ACA GCA-3' (SEQ ID NO:15), AL23—5' CCC TGG CGG CAA TCC TGA CTT TCA-3' (SEQ ID NO:16), and AL25—5'-TCA TGAGCT CTC CAT CCA TCC TGA-3' (SEQ ID NO:17). 5',3' RACE was performed on two myeloid cell lines HL-60 and U937 using the Exact START™ Eukaryotic mRNA 5'- & 3'-RACE Kit according to the manufacturer's instructions.

Double thymidine block (early S-phase block): HL-60 cells were grown overnight to 70-80% confluence, washed twice with 1×PBS, and cultured in DMEM (10% FCS)+2.5 mM thymidine for 18 h (first block). Thymidine was washed out with 1×PBS, and cells were grown in DMEM (10% FCS). After 8 hours, cells were cultured in presence of thymidine for 18 h (second block) and then released as described. Synchrony was monitored by flow cytometry analysis of propidium iodide-stained cells using a LSRII flow cytometer (BD Biosciences) at the Harvard Stem Cell Institute/Beth Israel Deaconess Center flow cytometry facility.

DRB and ML-60218 treatment: After release from double thymidine block, HL-60 cells were treated with 100 μM of 5,6-Dichlorobenzimidazole 1-β-D-ribofuranoside (DRB) (Sigma Aldrich) for 1, 2, and 3 hours. HL-60 cells were treated with 25 μM ML-60218 (2-chloro-N[5-(5-chloro-3-methyl-1-benzothiophen-2-yl)-2-methylpyrazol-3-yl]benzenesulfonamide, Calbiochem®) for 24 hours. Total RNA was harvested as described above and expression levels of C/EBPa, ecRNA, and 5S were measured by Taqman qRT-PCR.

5' Azacytidine (5 Aza-CR) treatment: K562 cells were cultured in the presence of 10 μM 5Aza-CR (Sigma Aldrich) or 2% 1×PBS (mock treatment). Medium was refreshed every 48 hours. RNA (for RT-PCR) and genomic DNA (for bisulfite sequencing) were isolated after 7 days of treatment.

Down-regulation of ecRNA: Three different short hairpin RNAs targeting the human ecRNA and one scrambled control were designed according to the Dharmacon software program and cloned into the lentivirus vector pLKO.1 (Sigma Aldrich), which has a puromycin selection marker. Lentivirus particles were produced as previously described (Stewart et al., RNA 9:493-501, 2003). HEK293T cells were co-transfected with either empty vector or the pLKO-shRNA vector and Gag-Pol and Env constructs using Lipofectamine™2000 (Invitrogen) according to the manufacturer's recommendation. Virus containing supernatants were collected 48 and 72 hours after transfection and concentrated using a Centricon Plus-70 100000 MWCO column (Millipore). Lentiviral transduction was performed in the presence of Hexadimethrine bromide (final concentration 8 μg/ml) in the human myeloid cell line U937. Puromycin (2 μg/ml) was added to the cultures two days after infection. Resistant clones were selected and screened for down-regulation of the ecRNA by qRT-PCR. The short hairpins RNAs sequences were as follows:

SC:
(SEQ ID NO: 31)
5'-ATCTCGCTTGGGCGAGAGTAA-3';

```
Sh#1:
                                 (SEQ ID NO: 32)
5'-AATAAATAGCAGAGGACAAGG-3';

Sh#2:
                                 (SEQ ID NO: 33)
5'-CAGGCAAGACAAATAAATAGC-3';
and Sh#3:
                                 (SEQ ID NO: 34)
5'-GAAGAGGCCTCCAGTGGTAGG-3'.
```

Up-regulation of ecRNA: The 3' downstream region of C/EBPa ecRNA and an unrelated genomic region were cloned into the pBabe retrovirus vector harboring a puromycin selection marker (Addgene plasmid 1764). K562 cells were transfected with the Amaxa Cell Line Nucleofector® Kit V, Program T-003. Puromycin (2 µg/ml) was added to the cultures two days after transfection. Resistant clones were selected and screened for upregulation of ecRNA and the unrelated region (UR) by Northern Blot Analysis. The primers for amplification of 3' and 5' regions (R1 and R2) and the Unrelated Region (UR) of ecRNA were as follows:

```
R1:
                                 (SEQ ID NO: 35)
forward: 5'- ATG TCG GTGTCT TTT TAA AAC CAG -3'
and (SEQ ID NO: 36)
reverse: 5'- GCT AAG CTT CCA GAG TGT AAA AGG -3';

R2:
                                 (SEQ ID NO: 37)
forward: 5'- CCC GGC CCC AGA GTT AAG TTT GTC -3'
and (SEQ ID NO: 38)
reverse: 5'- CGG CCC AGCTTT TAT ACC CGG CAG -3';
and UR:
                                 (SEQ ID NO: 39)
forward: 5'- TA TAC AGC CAT GAA AGA AAC TTAC -3'
and (SEQ ID NO: 40)
reverse: 5'- AGT TTT ACT GTG GTG TGT TTG TTC -3'.
```

Bisulfite Treatment, Combined Bisulfite Restriction Analysis Assay (COBRA) and Bisulfite Sequencing: The methylation profile of the C/EBPa gene locus was performed by bisulfite sequencing as previously described. Briefly, 1 µg of genomic DNA was bisulfite converted by using EZ DNA Methylation kit (Zymo Research, Orange, Calif.). The primers and PCR conditions for bisulfite sequencing and combined bisulfite restriction analysis assay (COBRA) are summarized below. For COBRA, PCR products were purified and incubated with BstUI at 60° C. for 3 h. The digested DNA was then separated on a 3.5% agarose gel and stained with ethidium bromide. For bisulfite sequencing, PCR products were gel purified (Qiagen) and cloned into the pGEM®-T Easy Vector System (Promega). Sequencing results were analyzed using BiQ analyzer software. The sequences of primers for COBRA and bisulfite sequencing were as follows: C/EBPa-1.4 kb region-: forward: 5'-GGT GTT TTT AGT TGT GTT TTT TT-3' (SEQ ID NO:41) and reverse: 5'-AAA CCC TAA AAC CCC TTA-3' (SEQ ID NO:42); C/EBPa Distal Promoter: forward: 5'-TAG TTT YGTTAG TTT GGG GGG TTT-3' (SEQ ID NO:43) and reverse: 5'-TCT AAT CTC CAA ACT ACC CCT ATA-3' (SEQ ID NO:44); C/EBPa coding region: forward: 5'-AGG TTA AGG YGG TTG TGG GTT TTA-3' (SEQ ID NO:45) and reverse:5'-CCA ACT ACT TAA CTT CAT CCT CCT-3' (SEQ ID NO:46); C/EBPa 3'UTR: forward: 5'-AGG TTYGTG GTA GGA GGA GGG TTT A-3' (SEQ ID NO:47) and reverse: 5'-TAA CCC ACR ACC TAA CTT TCT AAT-3' (SEQ ID NO:48); TP73 promoter: forward: 5'-GTG GGY GGT TTY GTY GGG TTT TGT-3'(SEQ ID NO:49) and reverse: 5'-ACC CCT AAA CRA ATT ATA TAA A-3' (SEQ ID NO:50); and C/EBPy promoter:

```
forward:
                                 (SEQ ID NO: 51)
5'- GAA GTG AATTTT TTA AAA TGA TTT -3'
and reverse:
                                 (SEQ ID NO: 52)
5'- TTT TGT TTT AGT TTT TTA AGT AGT TGG GA-3'.
```

MassARRAY: Quantitative DNA methylation analysis using the MassARRAY technique was performed by Sequenom, Inc., as previously described (Frommer et al., Proc Natl Acad Sci USA 89: 1827-1831, 1992). Briefly, 1 µg of genomic DNA was converted with sodium bisulfite using the EZ DNA methylation kit (Zymo Research, Orange, Calif.), FCR amplified, in vitro transcribed, and then cleaved by RNase A. The samples were then quantitatively tested for their DNA methylation status using MALDI-TOF mass spectrometry. The samples were desalted and spotted on a 384-pad SpectroCHIP (Sequenom) using a MassARRAY nanodispenser (Samsung), followed by spectral acquisition on a MassARRAY Analyzer Compact MALDI-TOF MS (Sequenom). The resultant methylation calls were performed by the EpiTyper software v1.0 (Sequenom) to generate quantitative results for each CpG site or an aggregate of multiple CpG sites. The methylation levels of aggregated multiple CpGs were calculated as the mean of each CpGs methylation value and presented as percentage.

Nuclear RNA immunoprecipitation (nRIP): nRIP performed as described by Ebralidze et al. (Science 303:383-387, 2004) with some modifications. Crosslinked nuclei were collected as follows: About 60×10$^6$ HL-60 cells were crosslinked with 1% formaldehyde (formaldehyde solution, freshly made 50 mM HEPES-KOH; 100 mM NaCl; 1 mM EDTA; 0.5 mM EGTA; 11% formaldehyde) for 10 minutes at room temperature. Crosslinking was halted by adding 1/10th volume of 2.66 M Glycine, kept for 5 minutes at room temperature and 10 minutes on ice. Cell pellets were washed twice with ice-cold PBS (freshly supplemented with 1 mM PMSF) and then resuspended in cell lysis buffer (volume=4 mL, 1× Buffer of 10 mM Tris pH 7.4; 10 mM NaCl; 0.5% NP-40, freshly supplemented with protease inhibitors (protease inhibitors cocktail: Roche Applied Science, Cat. No. 1836153, 1 tablet with 375 µL H$_2$O; add as ×100), 1 mM PMSF, and 2 mM vanadyl complex (NEB)). Cells were incubated at 0° C. for 10-15 minutes and homogenized by Dounce (10 strokes pestle A and 40 strokes pestle B). Nuclei were recovered by centrifugation at 2,000 rpm for 10 minutes at 4° C. Nuclei were resuspended in 3 ml 1× Resuspension Buffer (50 mM HEPES-NaOH, pH 7.4; 10 mM MgCl$_2$) supplemented with 1 mM PMSF and 2 mM vanadyl complex. DNase treatment (250 U/ml) was performed for 30 minutes at 37° C., and EDTA (final concentration 20 mM) was added to halt the reaction. Resuspended nuclei were sonicated once for 20s (1 pulse every 3 seconds) at 30% amplitude (Branson Digital Sonifer, Danbury, Conn.).

Immunoprecipitation: Before preclearing, the sample was adjusted to 1% Triton X-100; 0.1% sodium deoxycholate; 0.01% SDS; 140 mM NaCl; Protease inhibitors; 2 mM vanadyl complex; and 1 mM PMSF to facilitate solubilization. In the preclearing step, ~50 ul magnetic beads (Protein A or G Magnetic Beads; #S1425S or #S143OS NEB) were added to the sample and incubation was carried out for 1 h on a rocking platform at 4° C. Beads were removed in a magnetic field. The sample was divided into three aliquots: (i) antibody of interest: DNMT1 antibody (Abcam cat #ab13537); (ii) preimmune serum: IgG (Sigma Aldrich); (iii) no antibody, no serum (input). About 5 μg antibody or preimmune serum was added to the respective aliquot and incubation performed on a rocking platform overnight at 4° C. Input was stored at −20° C. after addition of SDS to 2% final concentration. On Day II, About 200 μl of Protein A coated super-paramagnetic beads (enough to bind 8 μg IgG) were added to the samples and incubated on a rocking platform for 1 h at 4° C. Six washes were performed with immunoprecipitation buffer (150 mM NaCl; 10 mM Tris-HCl, pH 7.4; 1 mM EDTA; 1 mM EGTA pH 8.0; 1% Triton X-100; 0.5% NP-40 freshly supplemented with 0.2 mM vanadyl complex and 0.2 mM PMSF) in a magnetic field. Proteinase K treatment to release DNA/RNA into solution and to reverse HCHO crosslinking was performed in 200 μl of: 100 mM Tris-HCl, pH 7.4; 0.5% SDS for the immunoprecipitated samples and in parallel for the input; Proteinase K, 500 μg/ml at 56° C. overnight. On Day III, beads were removed in magnetic field. Phenol (pH 4.3) extraction was performed after addition of NaCl (0.2 M final concentration). EtOH precipitation (in the presence of glycogen) was conducted for 3 hours at −20° C. The pellet was dissolved in 180 μl $H_2O$, heated at 75° C. for 3 minutes, and immediately chilled on ice. Samples were treated with DNase I (250 U/ml) in the presence of RNase inhibitor 300 U/ml in ×1 buffer #2 (NEB) at 37° C. for 30 minutes. Phenol (pH 4.3) extraction and EtOH precipitation were repeated. The RNA pellet was dissolved in 50 μl $H_2O$.

Electrophoretic gel mobility shift assays (EMSAs) and Kd determination: DNA and RNA oligonucleotides (15 pmol) were end-labeled with [γ-32P] ATP (Perkin Elmer) and T4 polynucleotide kinase (New England Biolabs). Reactions were incubated at 37° C. for 1h and then passed through G-25 spin columns (GE Healthcare) according to the manufacturer's instructions to remove unincorporated radioactivity. Labeled samples were gel-purified on 10% polyacrylamide gels. Binding reactions were carried out in 10 μL volumes in the following buffer: 5 mM Tris pH 7.4, 5 mM $MgCl_2$, 1 mM DTT, 3% v/v glycerol, 100 mM NaCl. Various amounts of purified DNMT1 protein (BPS Bioscience Inc., 0.021-0.156 μM) were incubated with 1.1 nM of 32P-labeled dsDNA and ss/ds RNAs. In the competitive assay, a fixed amount of protein and increasing amounts of competitors (dsDNA or poly (dI-dC)) were used. All reactions were assembled on ice and then incubated at room temperature. Samples were loaded onto 6% native polyacrylamide gels (0.5×TBE) at 4° C. for 3 h at 140 V. Gels were dried and exposed to X-ray film and a PhosphorImager screen. Data were analyzed with ImageQuant software. For affinity assays, the percent shifted species was determined as follows: the migration of the labeled DNA in this reaction was defined as zero percent shifted and the ratio of the PhosphorImager counts in the area of the lane above this band to the total counts in the lane was defined as background and subtracted from all other lanes. This band represented total input. Subsequent lanes containing DNMT1-nucleic acid complexes were treated identically, and the percentage complex formation was calculated as follows: [Input-(free probe for each lane+background/input)]. All experiments contained a control reaction lacking DNMT1. The percentage complex formation was plotted as a function of DNMT1 concentration using nonlinear regression analysis using Prism 4.0a.

In vitro Transcription-Methylation Assay: The in vitro transcription-methylation assays were performed on hemimethylated DNA (FIG. 14H) in the presence or absence of 5 U of human DNMT1 (New England Biolabs) and 5 U of T7 RNA polymerase (Promega) or 5 U of *E. coli* RNA polymerase sigma-saturated holoenzyme (Epicentre). Reactions were performed in DNMT1 buffer according to the manufacturer's recommendations supplemented with rNTPs and 1.25 mM $MgCl_2$, including the "DNMT1 only" reaction. This predetermined concentration of $Mg^{2+}$ cations is high enough to sustain activity of RNA polymerases and low enough not to inhibit DNMT1 activity. The primers for the in vitro transcription/methylation assays were as follows: Forward: 5'-GGA AGG GCG ATC GGT GCG GGC CTC-3' (SEQ ID NO:53), reverse (biotinylated): 5'-Biotin-CAG CCC TCG AGG CCC GAA GCC ACC-3' (SEQ ID NO:54), and reverse (not-biotinylated): 5'-CAG CCCTCG AGG CCC GAA GCC ACC-3' (SEQ ID NO:55).

RNA immunoprecipitation sequencing (RIPseq): Total RNA immunoprecipitated with DNMT1 antibody (Abcam cat #ab13537) and IgG (Sigma Aldrich) was processed for sequencing as described by Mortazavi et al. with some modifications. Double stranded cDNA was synthesized using the Just cDNA Double-Stranded cDNA Synthesis Kit (Agilent Technology, Santa Clara, Calif.) according to the manufacturer's instructions. Illumina sequencing libraries were constructed from these cDNA using a ChIP-Seq sample preparation kit (cat #IP-102-1001, Illumina, San Diego, Calif.) with minor modifications. Illumina paired-end adaptor and PCR primers were used to replace the single read adaptor and primers in the kit. Constructed libraries were subjected to a final size-selection step on 10% Novex TBE gels (Invitrogen, Carlsbad). DNA fragments of 175-200 bp were excised from a SYBR-green-stained gel. DNA was recovered from the gel and quantified following Illumina's qPCR quantification protocol. Paired end sequencing of these libraries was then performed on an Illumina GA IIx to achieve 2×76 bp reads. Paired-End reads were trimmed to 50 bp and aligned to the reference genome hg19 using BWA59 with the following parameters: bwa aln −o 1 −l 25 −k 2; bwa sample −o 200. Then, the genome was divided into course bins (10 Kb) and reads were counted for DNMT1 RIP and IgG control in each bin. A linear regression was fitted across all non-zero bins and the slope of the regression was used as a scaling factor alpha to normalize the RIP and control. Overlapping reads in the DNMT1 RIP were aggregated into contiguous intervals. Each DNMT1 interval was tested for significance by comparing the number of reads within the interval the number of reads in the same region of the IgG control, multiplied by the scaling factor (exact binomial test, P=0.5). Multiple tests were corrected by Benjamini-Hochberg. 16,187 intervals (representing the start and end boundaries of peaks) were determined to be significantly enriched in the DNMT1 RIP as compared to the IgG control (P<0.0001; q<0.0001). A false discovery rate of 7.5% was determined by determining the number of significantly enriched intervals in the IgG immunoprecipitate using DNMT1 as a control. Significantly enriched DNMT1 intervals have a mean length of 347 bp and a median of 67 reads per interval. Every peak represents an interval with a 'height' value: the sum of all reads within an interval. All peaks were annotated with CEAS28 build on RefSeq hg19. A peak was considered belonging to a gene if located in the gene body or 3 kb up or downstream the gene (gene loci). Altogether, 6038 gene loci were covered by a least 1 significant RTPSeq peak.

Reduced representation bisulfite sequencing (RRBS): High quality genomic DNA was isolated from the myeloid cell line HL-60. DNA was digested with Msp1 (NEB), a methylation-insensitive enzyme that cuts C'CGG. Digested DNA was size selected on a 4% NuSieve 3:1 Agarosegel (Lonza). For each sample two slices containing DNA fragments of 40-120 bp and 120-220 bp, respectively, were excised from the unstained preparative portion of the gel. These two size fractions were kept apart throughout the procedure including the final sequencing. Pre-annealed Illumina adaptors containing 5'-methyl-cytosine instead of cytosine wereligated to size-selected MspI fragments. Adapter-ligated fragments were bisulfite-treated using the EZ DNA Methylation kit (Zymo Research, Orange, Calif.). The products were PCR amplified, size selected, and sequenced on the Illumina GA IIx at a reading length of 36 bp. Sequencing reads were mapped to the reference genome hg19 using RRBSmap61 allowing 2 mismatches. Reads from replicates were merged and processed using a custom computational pipeline. We considered only CpG located in regions with a depth of coverage greater than 3 reads. The β-score of CpG methylation in a given position is the ratio of methylated CpGs within the total number of CpGs through all reads. Levels of genes methylation is the mean of all CpG β-scores within −2 kb from the TSS to the end of first intron; for intronless genes the entire gene body was considered. Genes with less than 3 sequenced CpG in the promoter or less than 3 sequenced CpG in the first exon-intron were excluded.

RNA expression profiling: RNA isolated from HL-60 cells was employed for sample amplification and labeling using the Whole Transcriptome assay reagent kits from Affymetrix. 10 µg of labeled RNA was hybridized on Affymetrix GeneChip Human Gene 1.0 ST array. Hybridization, washing, staining, and scanning were carried out as recommended by the manufacturer. Each hybridization reaction was performed in triplicates. Washes and staining were performed through the Fluidics Station 400 and the GeneChip® Scanner 3000 (Affymetrix, Santa Clara, Calif., USA) was used to measure the fluorescence intensity emitted by the labeled target. Raw data processing was performed using the Affymetrix GeneChip® Operating Software (GCOS). Microarrays were RMA normalized using 'affy', a R-Bioconductor library. C/EBPa expression was used as a threshold to define expressing ($>\log_2$ (4)) and not expressing ($>\log_2$ (4)) genes for the further analysis.

Data integration: We used the RefSeq transcripts database built on hg19 (UCSC release) as a genome annotation reference for RipSeq, RRBS, and microarray expression experiments. We selected only the longest transcripts. Accordingly, the number of 40857 RefSeq Ids was reduced to 23250 transcript Ids. Then, we annotated all RIPSeq peaks against the gene loci which include exonic, intronic, and UTR regions plus 3 kb upstream of the TSS and 3 kb downstream of the Transcription End Site (TES) regions. We identified 6038 gene loci with DNMT1-RIPseq peaks and 17212 gene loci without DNMT1-RIPseq peaks. Finally, we focused our study on gene loci covered by the RRBS. We identified 4833 gene loci with DNMT1-RIPseq peaks and covered by RRBS and 10973 gene loci without DNMT1-RIPseq peaks and covered by RRBS.

Gene ontology (GO): GO analysis was performed with DAVID. We focused our analysis on biological process annotations. GO enrichment was scored using the Benjamini corrected p-value.

Statistical analysis: Methylation changes of clones analyzed by bisulfate sequencing were calculated using the Fisher's exact test (GraphPad Prism Software Inc.). Methylation changes assessed by MassARRAY were calculated using paired t-test (GraphPad Prism Software Inc.). The statistical evaluation of DNMT1-RNA interaction versus expression and methylation was estimated using the student t-test. For both populations: DNMT1-bound group and DNMT1-unbound group (box-plots; FIG. 15B), we measured the overrepresentation of genes which follow our hypothesis (clusters B and C) against the ones which do not (clusters A and D) using a 2-sample proportion test. P-values for t-test and 2-sample proportion test were calculated by the R functions "t.tcst" and "prop.test" respectively. Values of $P \leq 0.05$ were considered statistically significant. The mean±s.d. of two or more replicates is reported.

Data availability: Microarray expression, RIPseq and RRBS data are available on the gene omnibus database under the accession IDs GSE32153, GSE32162, and GSE32168 respectively.

The following examples are intended to illustrate, rather than limit the invention.

Example 1

Characterization of Extra-Coding RNAs of C/EBPa

We hypothesized that non-coding RNAs (ncRNAs) may function to regulate gene expression. To further test the universal character of the functionality of ncRNAs, we focused on the CCAAT enhancer binding protein alpha (C/EBPa) gene locus. C/EBPa is a master regulator in the hematopoietic system, and its expression is crucial during granulocytic differentiation. Impaired C/EBPa expression and/or function disrupts granulopoiesis and contributes to leukemogenesis, and the presence of C/EBPa mutations is now one of the criteria in the classification of human Acute Myelogenous Leukemia (AML). In consideration of its fundamental role in hematopoiesis, we decided to investigate the existence of ncRNAs within the C/EBPa gene locus and to assess their functional role in the gene expression.

Figure 1B:
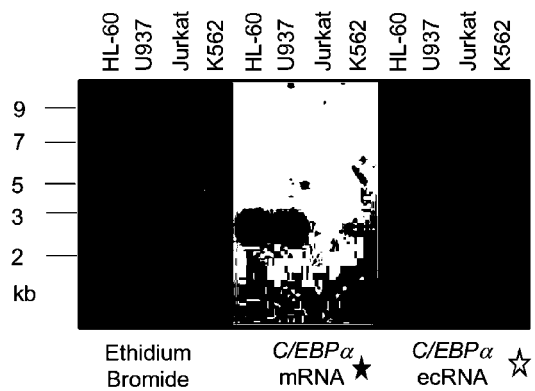
Figure 1C:
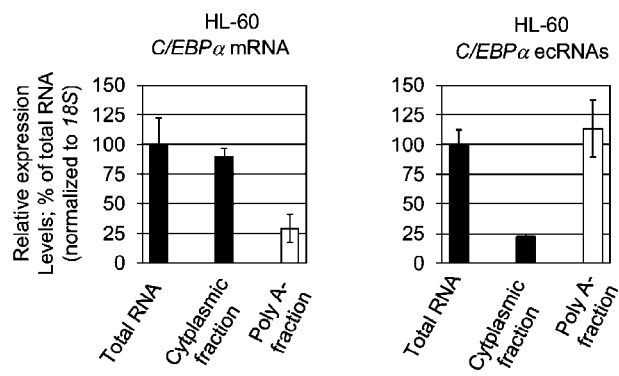
Figure 1D:
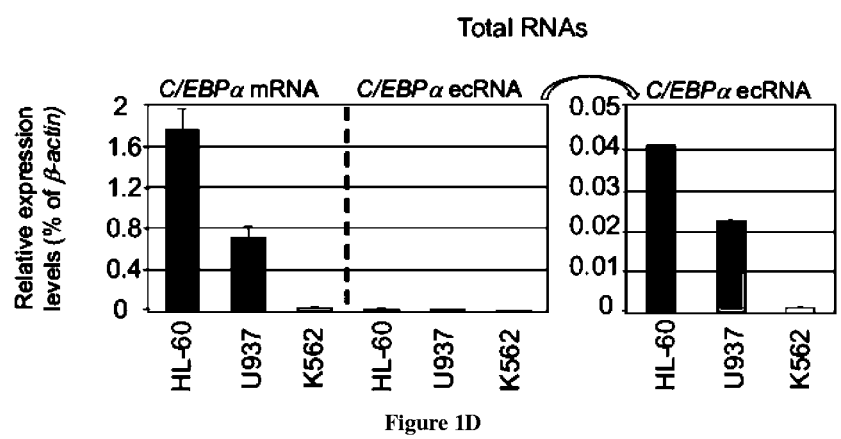
Figure 1E:
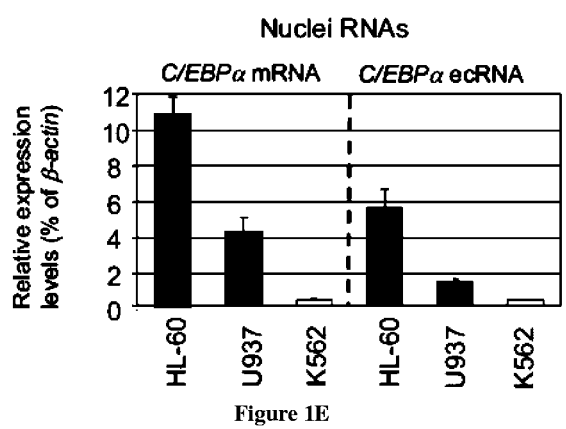
Figure 1F:
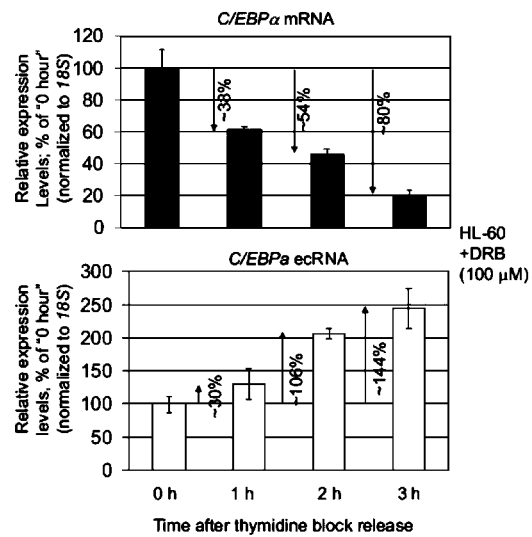
Figure 1G:
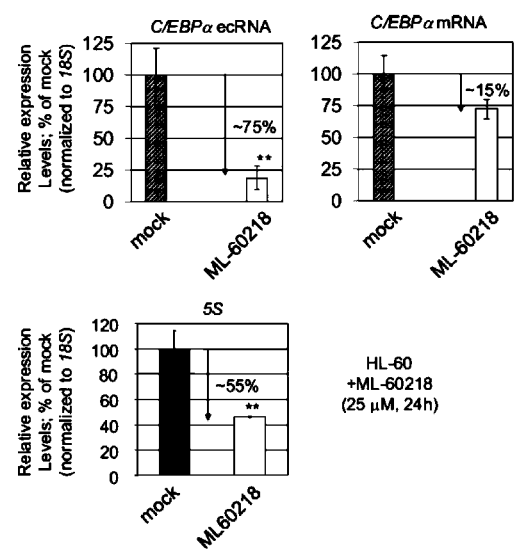
Figure 1H:
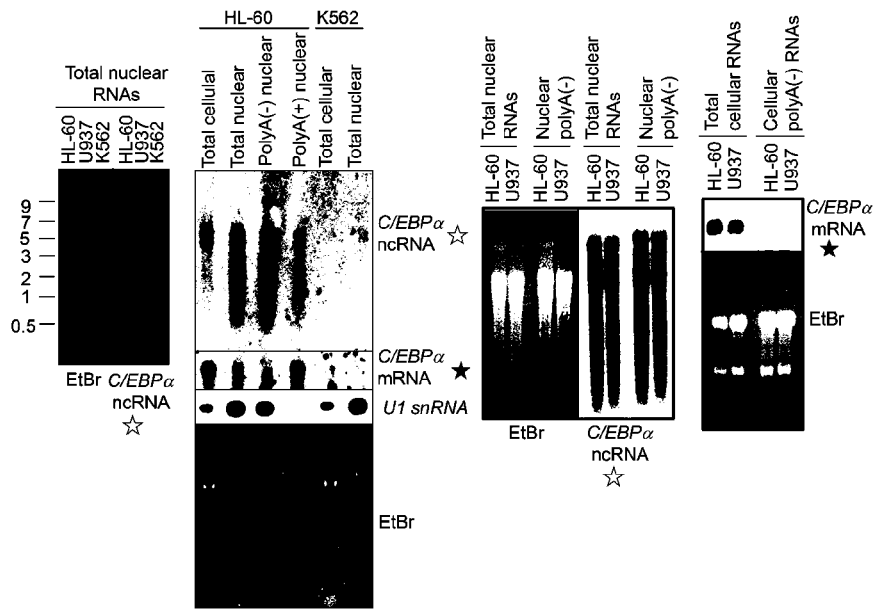
Figure 1I:
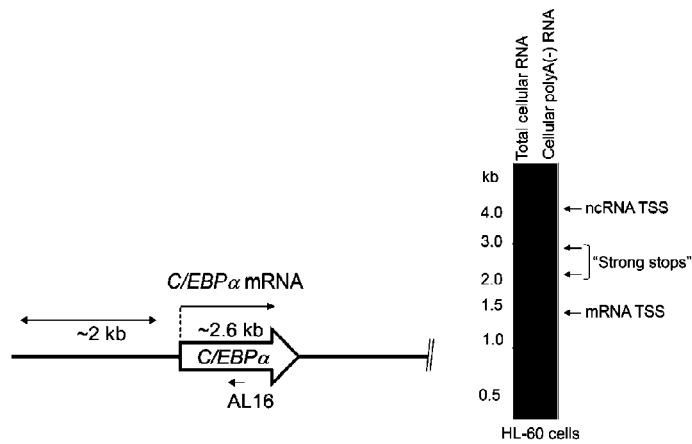
Figure 1J:
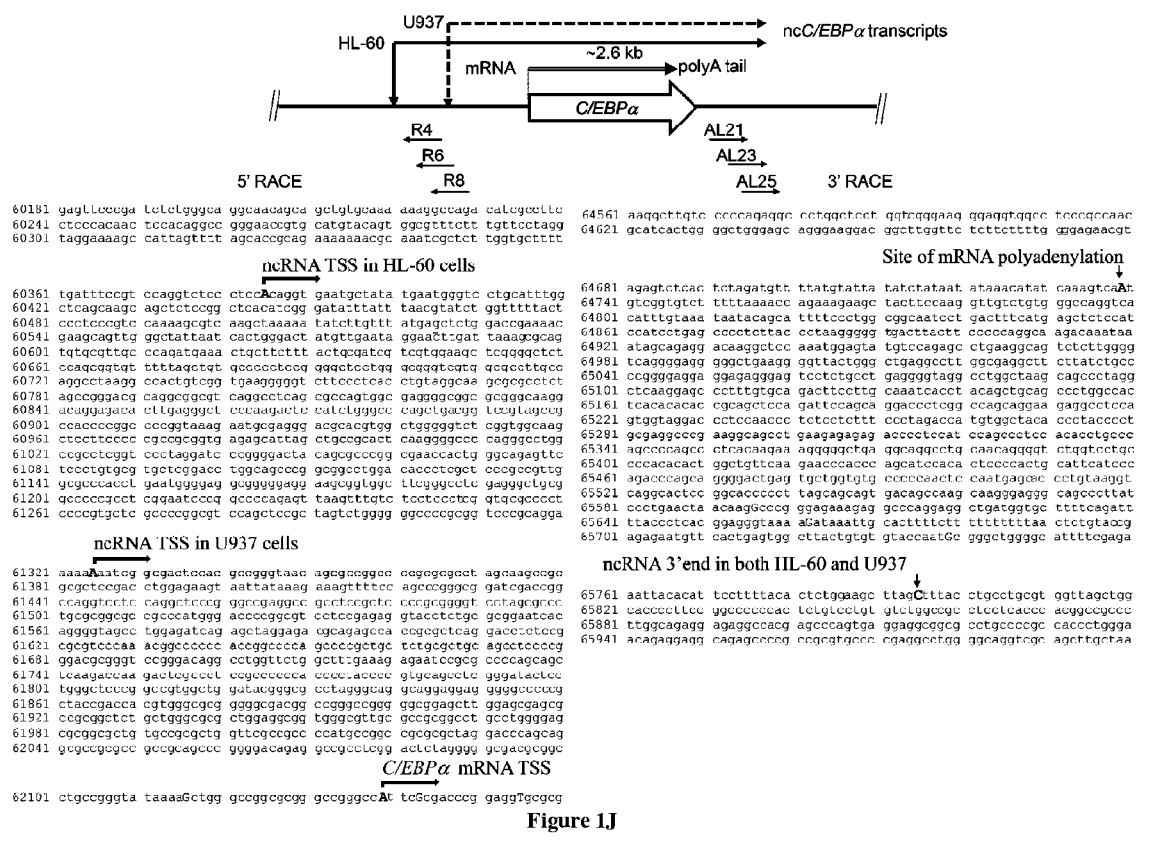

As expected, we observed extensive "extra-coding" transcription arising within the C/EBPa locus (FIGS. 1A-1C). Northern blot analysis of total RNA from four leukemic cell lines, probing the region immediately after the C/EBPa polyadenylation site, revealed the presence of a major band of ~5 kb in HL-60 and U937, but not in K562 or Jurkat cell lines (FIGS. 1A-1B). The identified transcript was distinct from the ~2.6 kb signal detected with a C/EBPa coding region probe, and correlated with C/EBPa mRNA expression. These non-polyadenylated transcripts were enriched in the nuclear fraction unlike polyadenylated C/EBPa mRNA (FIGS. 1C, 1H) suggesting that this RNA may have functional roles independent of protein coding potential. To map the entire length of these transcripts, we performed primer extension and 5', 3' RACE on total and polyA(−) RNAs isolated from HL-60 and U937 cells. That allowed us to identify the transcriptional start site (TSS) of these long ecRNAs, one at −1.4 kb and another at −0.8 kb upstream of the canonical C/EBPa mRNA TSS in HL-60 and U937 cell lines, respectively. Both novel transcripts terminated at +3.6 kb downstream from the C/EBPa TSS (FIGS. 1I, 1J). These transcript(s) are "extra-coding" rather than non-coding, since they overlap the single C/EBPa exon and could potentially encode C/EBPa protein. Theoretically, all regions of these extra-coding RNAs (ecRNAs) could potentially bind to DNMTs with high affinity. qRT-PCR analysis confirmed concordant expression mode between extra-coding and coding transcripts, in both cellular and nuclear RNAs (FIGS. 1D-1E).

Figure 1K:
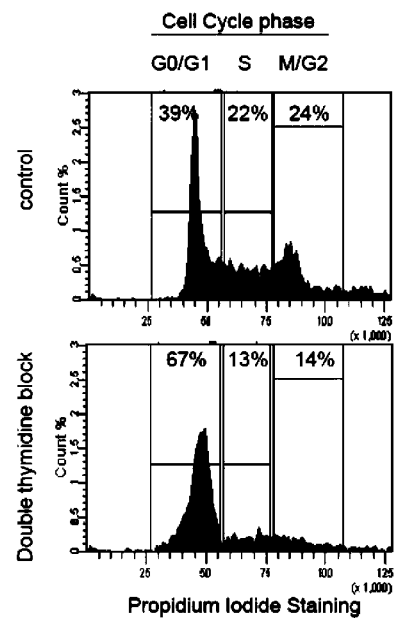
Figure 1L:
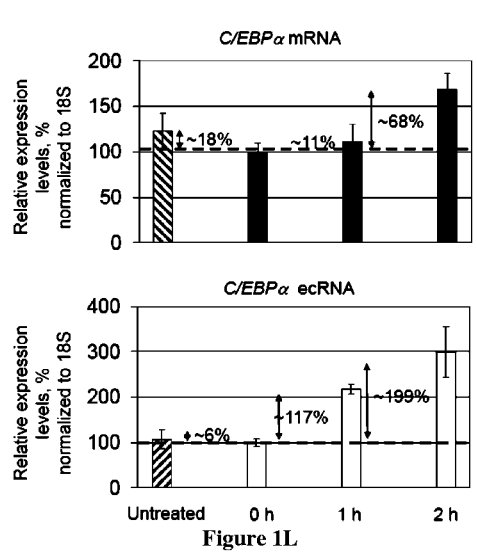

To exclude the possibility that these long transcripts are unspliced precursors of the intronless C/EBPa gene, we examined the time course of the RNA synthesis and the RNA polymerase type(s) responsible for the initiation of messenger and ecRNA. First, HL-60 cells synchronized by double thymidine block (thymidine arrests cells at the G0/G1 phase boundary) were analyzed upon release from the block (with ~85% of cells entering the G1/S phase; FIG. 1K). Induction of ecRNA was observed immediately after the block release, at marked contrast to significantly lower levels of C/EBPa mRNA at this time point (FIG. 1L). Thus, we stipulated that C/EBPa ecRNA synthesis precedes the expression of its overlapping mRNA. Next, synchronized HL-60 cells were analyzed after treatment with the RNA polymerase II (Pol II) inhibitor DRB at different time points. In the presence of DRB, we observed strong down-regulation of mRNA but no decrease in ecRNA expression levels (FIG. 1F), suggesting that the ecRNA transcription is mediated by a different RNA polymerase than Pol II. To determine the effect of polymerase on ecRNA synthesis, we employed a specific RNA polymerase III (Pol III) inhibitor, ML-60218. Treatment with ML-60218 resulted in marked down-regulation of ecRNA, with little effect on C/EBPa mRNA (FIG. 1G). Collectively, these findings identify a novel Pol III-regulated RNA (i.e., ecRNA) overlapping the C/EBPa locus and preceding C/EBPa mRNA expression in S phase.

Example 2

Functional Role of ecRNAs on mRNA Expression and DNA Methylation for C/EBPa

Figure 2A:
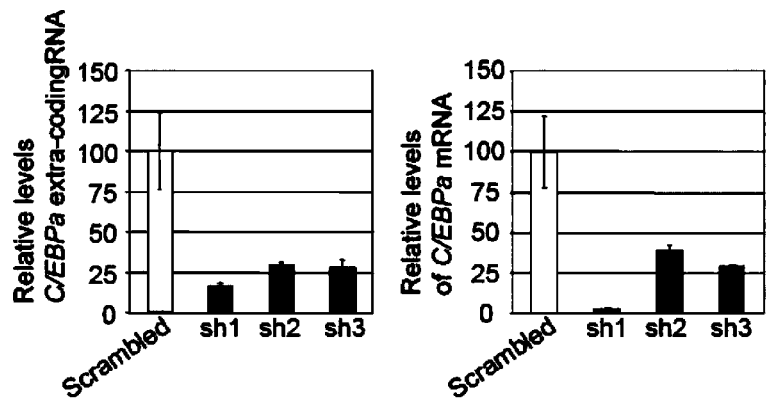
FIGS. 2A-2C show that down-regulation of C/EBPa extra-coding RNAs leads to down-regulation of C/EBPa mRNA expression and increased methylation of the C/EBPa promoter region.
Figure 2B:
Figure 2C:
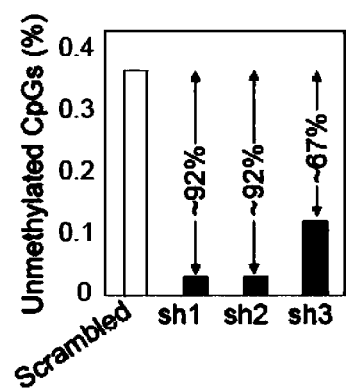

We also interrogated the functional role of ecRNAs for C/EBPa. Lentiviral shRNA-mediated down-regulation of ecRNAs led to significant down-regulation of the mRNA (FIG. 2A). Furthermore, down-regulation of ecRNAs also affected the methylation status within the C/EBPa locus. When transcription of ecRNAs was reduced by shRNAs, DNA methylation levels within the upstream promoter region were significantly increased (FIGS. 2B-2C). As shown in FIG. 2C, down-regulation of C/EBPa ecRNAs resulted in about 67%-92% increased methylation of CpG islands compared to control with scrambled shRNA. C/EBPa expression can be highly susceptible to methylation control, and hypermethylation in the CpG island within the upstream promoter region of the C/EBPa gene has been shown in a subclass of leukemia patients in the absence of other known genetic mutations. Based on these results, CROs can be used to target ecRNA and decrease methylation of tumor suppressor genes, such as C/EBPa.

Figure 3:
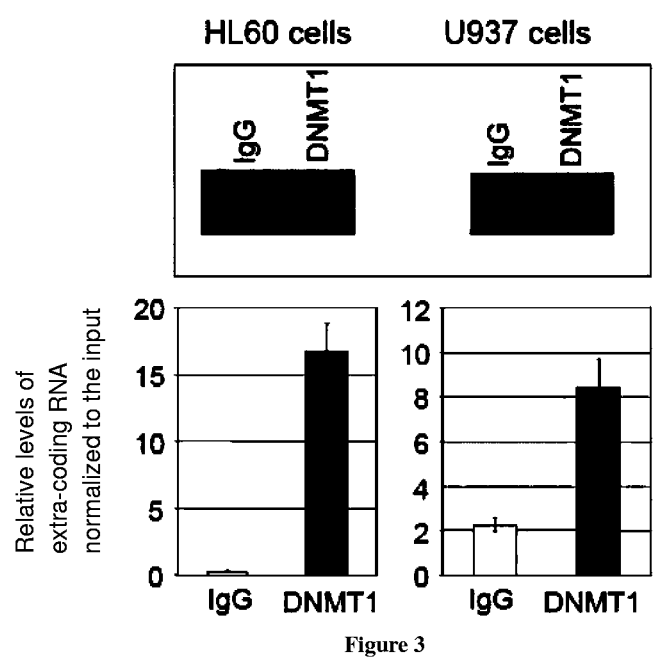
FIG. 3 shows immunoprecipitation of C/EBPa extra-coding RNAs with antibodies against DNA methyltransferase 1 (DNMT1) and with control (IgG). The upper panel shows the end-point of RT-PCR, and the bottom panel shows graphs having quantitated results from real time qRT-PCR.

In order to unveil the mechanistic aspects behind the control of DNA methylation by transcription, we performed in vivo RNA immunoprecipitation (RNA IP) with ChIP-grade antibodies against DNA methyltransferase 1 (DNMT1). We repeatedly observed a significant enrichment of C/EBPa ecRNAs in the immunoprecipitated RNA fraction (FIG. 3).

We also observed enrichment of other transcripts (e.g., extra-coding RNAs found in the PU.1 gene locus) and immunoprecipitation of other RNAs with DNMT1 antibody. Since RNA-DNMT1 binding appears not to be sequence-specific, these complexes can be formed not only with C/EBPa transcripts but with other RNAs as well. Previous studies have shown that downregulation of PU.1, by deletion of an upstream regulatory element (URE), induced acute myeloid leukemia, T-cell lymphoma, and chronic lymphocytic leukemia-like disease in a murine model (see Rosenbauer et al., Nat. Genet. 36:624-630, 2004; and Rosenbauer et al., Nat. Genet. 38:27-37, 2006). Similarly, downregulation of PU.1 has been observed in myeloma cell lines and in a subset of freshly isolated myeloma cells. The 17-kb 5' upstream enhancer (URE) and the promoter region of the PU.1 gene were highly methylated in human myeloma cell lines. Both sequences correspond to genomic regions giving rise to different ecRNAs (Ebralidze et al., Genes Dev. 22:2085-2092, 2008). Following 5-aza-2'-deoxycytidine treatment, upregulation of PU.1 expression and correspondent growth arrest of myeloma cells have been observed (Tatetsu et al., Cancer Res. 67:5328-5336, 2007). The demethylating effect of CROs can be tested by its ability to restore PU.1 expression by correcting the aberrant methylation pattern in the URE and promoter region of myeloma cells. FIG. 9 shows exemplary extra-coding RNAs (SEQ ID NOs:2-5) for use in generating CROs that can target SPI1 and reduce PU.1 methylation.

Example 3

Binding Interactions Between ecRNAs for C/EBPa and DNMT

To test the binding ability of DNMT1 to C/EBPa ecRNAs, we performed RNA electrophoretic mobility shift assays (REMSA). We observed strong binding of DNMT1 to folded RNAs comparable to that of double-stranded DNAs with the same primary sequence (FIGS. 4A-4E). Importantly, single-stranded RNA of the same primary sequence had almost undetectable binding to DNMT1 (FIG. 4E). Thus, single-stranded CROs bound to its target sequence will bind DNMT, but unbound single-stranded CROs will not bind (i.e., inactivate) DNMT. In this manner, gene-specific demethylation is obtained.

Next, we compared REMSAs with fully folded and RNase T3 digested 250 transcripts corresponding to CG-rich regions of the C/EBPa extra-coding RNA and the luciferase gene (FIG. 4F). A very similar pattern was obtained for these two non-homologous sequences, strongly suggesting the non-sequence-specific nature of the interaction between DNMT1 and RNA. Thus, the mechanism discovered for C/EBPa, as described herein, could be applicable to other genes.

Figure 5A:
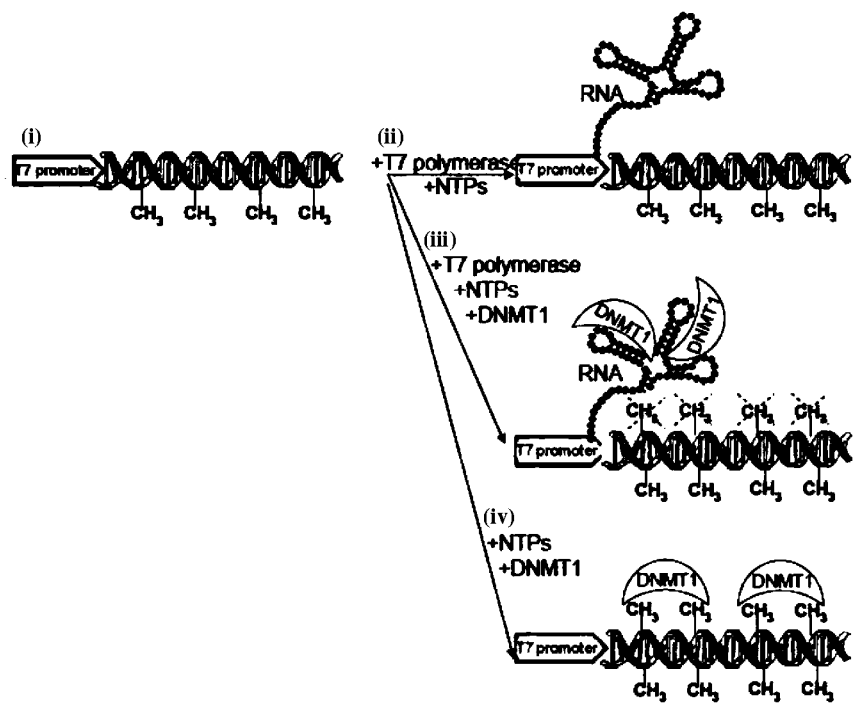
FIGS. 5A-5B show that transcription interferes with DNA methylation using an in vitro assay.
Figure 5B:

Finally, we tested the role of active transcription on DNMT1's ability to methylate DNA. Using in vivo methylation assays, we determined the methylation status of hemi-methylated DNA in the presence or absence of transcription. FIG. 5A(i)-(iv) shows various in vitro assays to determine the effect of transcription on methylation status, where a parallel assay including polymerase and DNMT1 can be used to determine methylation status during transcription (FIG. 5A(iii)) and another assay including DNMT1 can be used to determine methylation status in the absence of transcription (FIG. 5A(iv)). Using combined bisulfite restriction analysis (COBRA), methylated sites were converted into restriction sites that can be digested by BstUI. FIG. 5B shows that digested products are absent when both DNMT1 and T7 polymerase are present, but digested products are present only when DNMT1 is present (black arrow). Thus, these data demonstrate that DNMT1 enzymatic activity occurs in the absence of transcription and that RNAs can be used to prevent or reduce DNA methylation. Based on the experiments described herein, interactions between ecRNAs and other DNMTs, such as DNMT3a or DNMT3b, can also be tested.

Example 4

Screening for ecRNAs Having Target Site Specificity

To obtain transcripts having target site specificity, we performed genomic database searches and Northern blot hybridization assays for ecRNAs that hybridize exclusively with the targeted genomic site (gene locus) but not to any other genomic site (gene loci).

Using the BLAST genomic database, we searched for potential hybridization sites for regions R1 and R2 within C/EBPa ecRNA (FIG. 1). R1 and R2 were assessed using the following BLAST parameters: −E: 10, −B: 100, filter: dust, −W: 8, −M: 1, −N: −1, −Q: 2, and −R: 1). Search results are provided for R2 (FIG. 7B) and R1 (FIG. 7C). Whereas R2 hybridized to 1,732 candidates, R1 hybridized to only one. Accordingly, R1 but not R2 will likely bind with target site specificity.

Using Northern blot hybridization, we manually assessed whether R1 and/or R2 would hybridize exclusively to one genomic site. As shown in FIG. 7D, probes corresponding to regions R1 and R2 were hybridized with total RNAs extracted from cells that express C/EBPa (i.e., HL-60 and U937 cell lines) and cells that lack C/EBPa (i.e., HEK293 and K562 cell lines). The probe corresponding to R2 provided non-specific hybridization to all four cell lines. In contrast, the probe corresponding to R1 provided specific hybridization to C/EBPa-expressing cell lines HL-60 and U937.

Based on the results of these two methods, region R1 of C/EBPa would be appropriate for ssCRO design. Accordingly, these methods could be used to determine other candidate transcripts having "target site specificity" for a targeted genomic site, such as one or more sites in SPI1 (spleen focus forming virus (SFFV) proviral integration oncogene spi1), RXRA (retinoid X receptor, alpha), RARB (retinoic acid receptor, beta), or any other gene described herein.

Example 5

Functional Studies of the ecRNA Regulating C/EBPa Expression

Figure 13A:
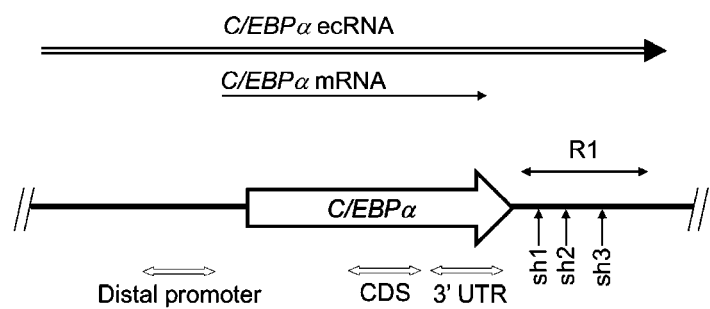
FIGS. 13A-13P show the loss- and gain-of-function studies demonstrating that ecRNA maintains C/EBPa expression by regulating methylation of the C/EBPa locus.
Figure 13B:
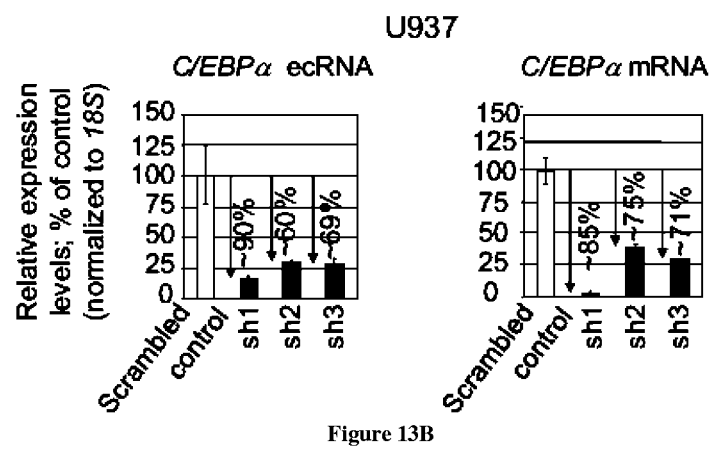
FIGS. 13B-13D show results of ecRNA loss-of-function, in which C/EBPa is expressed.
Figure 13C:
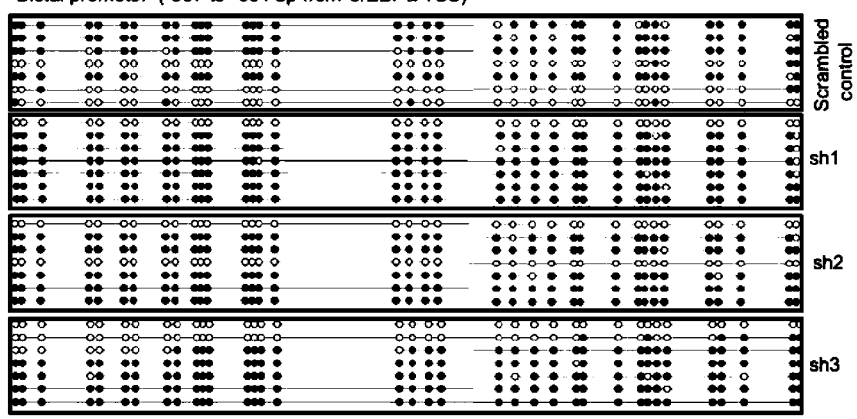
Figure 13D:
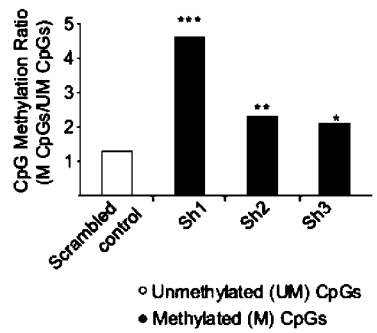

Further to Example 2 and to examine the functional role of the ecRNA in regulation of C/EBPa transcription on the C/EBPa locus, we performed RNA interference-mediated loss-of-function and overexpression-mediated gain-of-function experiments. Efficient knock-down of the ecRNA (~4-fold decrease) achieved by small hairpin (sh) RNAs targeting the 3' end of the ecRNA (but not including the C/EBPa mRNA) led to a decrease of C/EBPa mRNA expression of similar magnitude (FIGS. 13A-13B), suggesting that ecRNA may regulate C/EBPa expression. In view of the observations that increased methylation of C/EBPa gene promoter sequences has been implicated in leukemia and lung cancer, we set out to examine if there was a connection between C/EBPa ecRNA and methylation of the C/EBPa locus. We analyzed methylation changes within the distal promoter (located at −0.8-0.6 kb from the C/EBPa transcription start site) by bisulfite sequencing (FIG. 13A). Intriguingly, ecRNA knockdown led to a significant increase in DNA methylation levels, compared to the non-targeting control (FIGS. 13C-13D).

Figure 13E:
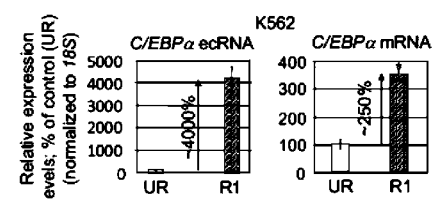
FIGS. 13E-13K show the results of ecRNA gain-of-function studies in K562 cells, in which C/EBPa is methylated and silenced.
Figure 13F:
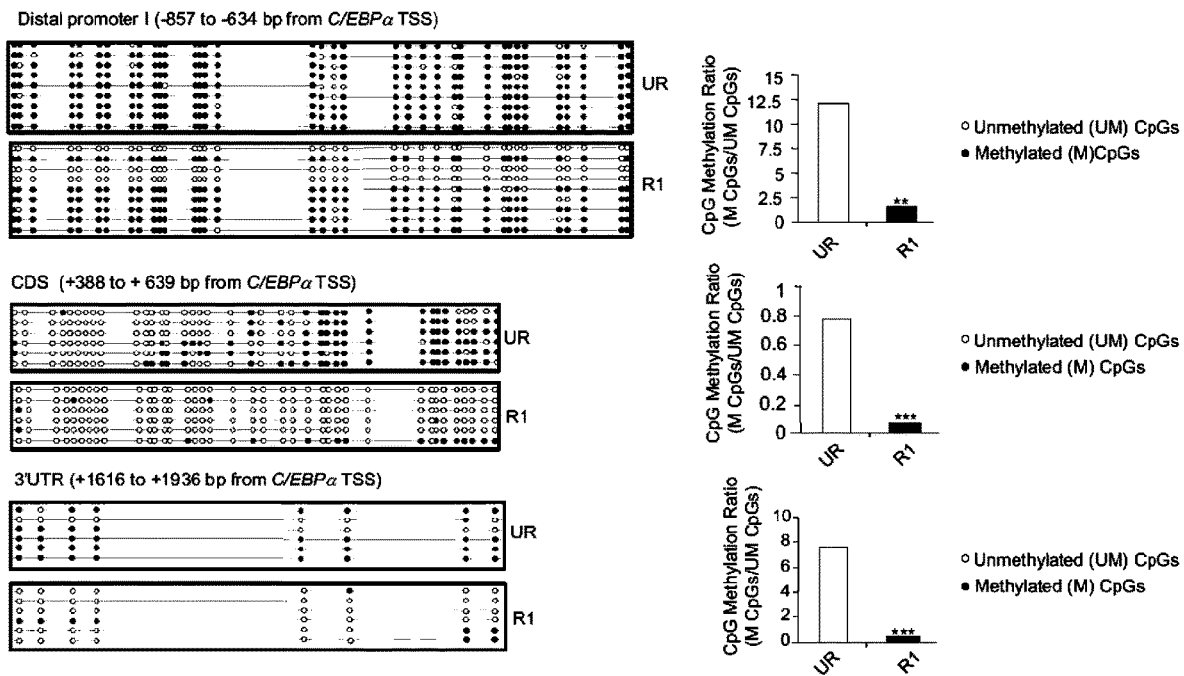
Figure 13G:
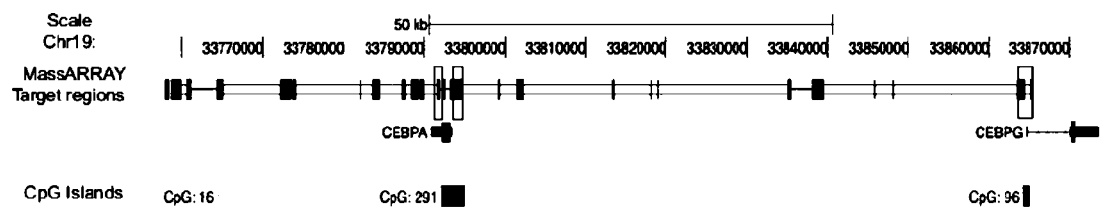
Figures 13H, 13I:
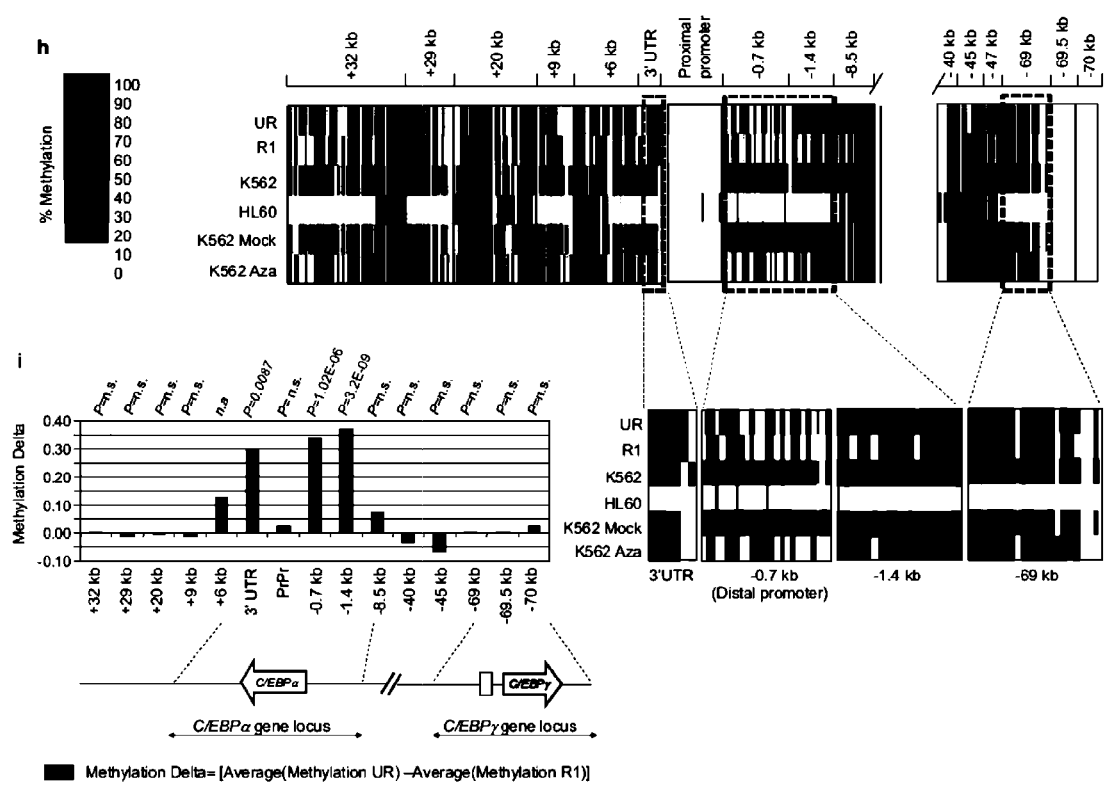
Figures 13J, 13K:
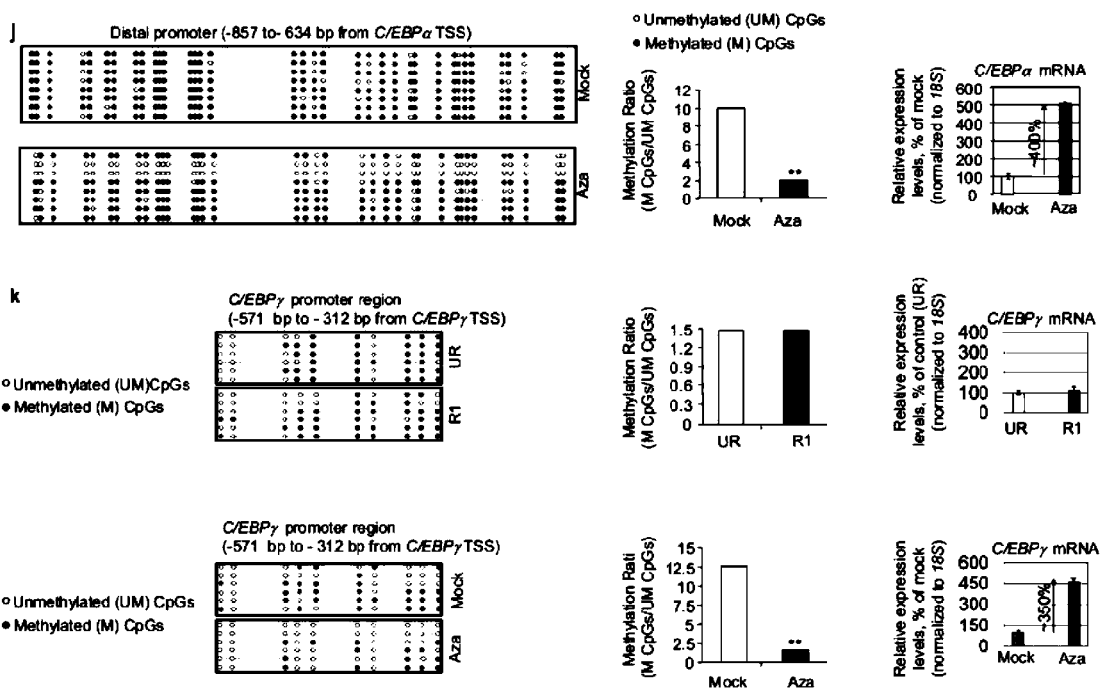
Figure 13L:
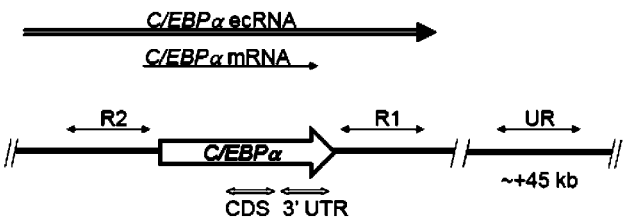
FIG. 13L is a diagram indicating the position of regions of the ecRNA employed for overexpression (R2 and R1) and unrelated regions (UR), and regions of C/EBPa gene analyzed for changes in DNA methylation (CDs and 3'UTR).
Figure 13M:
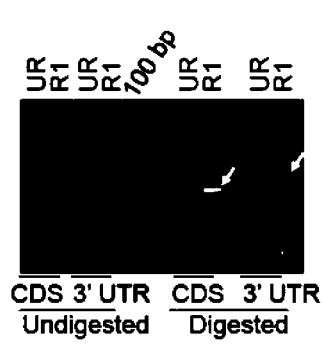
FIG. 13M is a Northern blot analysis of untransfected K562 and K562 stably transfected with constructs R1, UR, and EV (empty vector) demonstrating uniformity of overexpression levels of R1 and UR constructs.
Figure 13N:
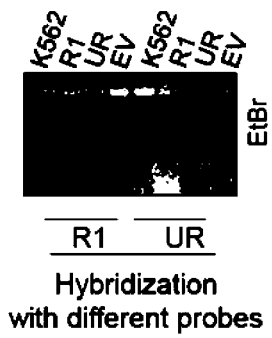
FIG. 13N shows the effect of ecRNA upregulation on methylation of the C/EBPa locus by COBRA analysis of the coding and 3' UTR regions of C/EBPa gene. Black arrows indicate incompletely digested PCR products of bisulfite converted genomic DNAs isolated from cells stably transfected with R1 and UR constructs.
Figure 13O:
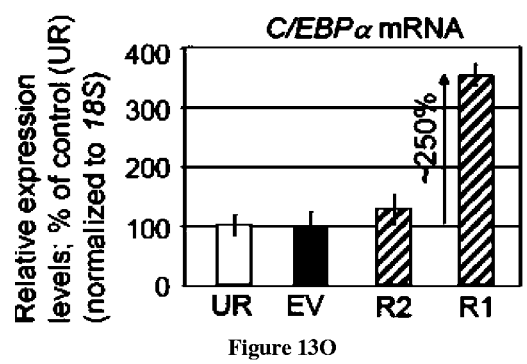
FIG. 13O shows the effect of ecRNA upregulation on levels of C/EBPa mRNA, where overexpression of R1 led to significant upregulation of ecRNA.

To investigate whether enforced expression of the ecRNA was sufficient to inhibit methylation, the downstream region of the ecRNA (R1) and an unrelated region (UR; located 45 kb downstream of the gene) were overexpressed in K562 cells, which express ecRNA and C/EBPa mRNA at low levels (FIGS. 13L-13M). Ectopic expression of the downstream region of ecRNA resulted in significant increase in mRNA expression (FIG. 13E) and concomitant decrease of DNA methylation in all three tested regions within the C/EBPa gene: the distal promoter, the C/EBPa coding region, and the C/EBPa 3' UTR. This effect was specific to the ecRNA as we did not observe changes in DNA methylation following overexpression of the unrelated region (UR) (FIG. 13F, 13N). Ectopic expression of the upstream region R2 of ecRNA did not affect C/EBPa expression, suggesting a modular character of the ecRNA (FIG. 13O). Indeed, analysis of the 3' part (R2) demonstrated its unique homology to the C/EBPa locus, whereas the 5' region (R1) shared sequence homology with thousands of genomic loci (FIGS. 7A-7D). Together, these loss- and gain-of-function experiments demonstrate that the presence of ecRNA prevents C/EBPa locus specific DNA methylation.

Figure 13P:
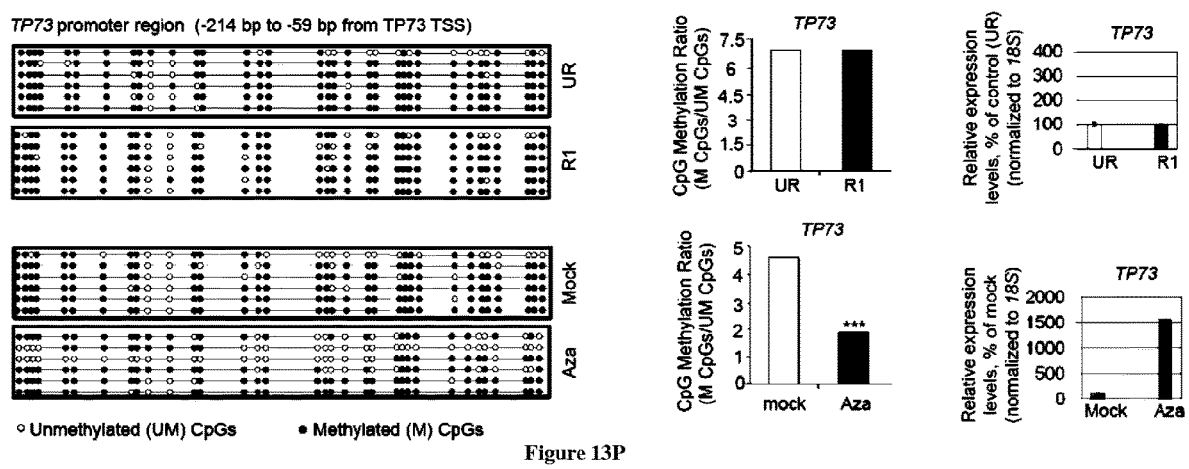

To assess the specificity of the ecRNA overexpression, we tested whether the effect was confined to the C/EBPa locus. We compared expression levels with DNA methylation changes resulting from ecRNA overexpression to that induced by the well-characterized hypomethylating agent 5'-azacytidine (5-Aza-CR). We applied a high-throughput methylation analysis of the C/EBPa locus using both a customized platform for massARRAY technology and direct bisulfite sequencing. Some 100 kb spanning both C/EBPa and the neighboring C/EBPg (C/EBP gamma, HGNC:1837, NCBI: NP_001797.1, NM_001806.2) gene were analyzed for both treatments (FIGS. 13G-13H). We did not observe major changes in methylation status outside the C/EBPa locus resulting from ecRNA overexpression (FIG. 13I). 5-Aza-CR treatment led to the expected increase of C/EBPa mRNA levels and reduced levels of DNA methylation of the C/EBPa locus (FIG. 13J). In contrast, increased mRNA expression within the neighboring C/EBPg gene and changes in methylation status were achieved only after 5-Aza-CR treatment (FIGS. 13J-13K) and not after R1 overexpression. In addition, to rule out off target effects on other chromosomes, we analyzed the expression and methylation profile of the TP73 gene promoter, located on chr1p36, methylated and not expressed in K562, before and after the two treatments. We detected expression and methylation changes exclusively after 5-Aza-CR treatment (FIG. 13P). These results demonstrate that this ecRNA inhibits DNA methylation at the C/EBPa locus, with no discernible effects on DNA methylation at other tested loci.

Collectively, these results confirm the inverse link between ecRNA and C/EBPa methylation, and highlight the gene-specific, highly localized effect, supporting a specific cis regulatory role of the ecRNA on C/EBPa expression. Accordingly, these experiments can be used to determine the effect of ecRNAs on the methylation status of other candidate transcripts, as well as to determine what regions of ecRNAs are most appropriate for CRO design for selectively or specifically targeting any of the genes described herein.

Example 6

Transcription Interferes with DNMT1 Methylation of DNA

Figure 14C:
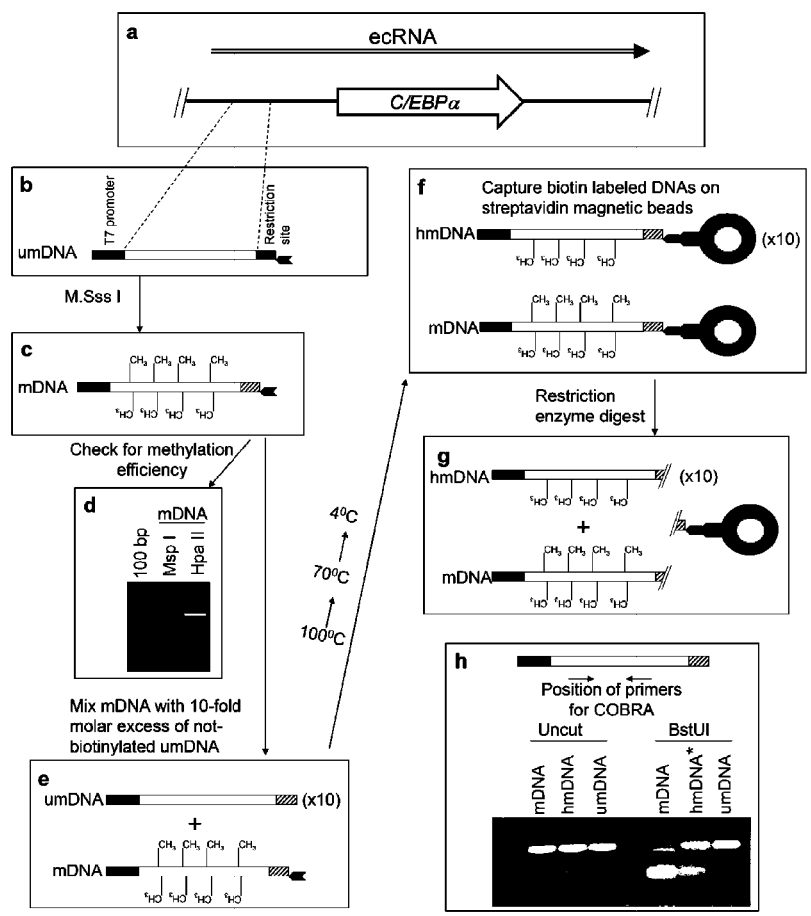

To examine whether the act of transcription itself could interfere with the ability of DNMT1 to methylate hemimethylated DNA, we performed a combined in vitro transcription and DNA methylation assay. A hemimethylated DNA segment (bottom strand methylated) corresponding to the 5' end of the ecRNA (located at −1.4-0.5 kb from the C/EBPa TSS) was engineered downstream of a T7 RNA polymerase promoter, and DNMT1 methylase activity was monitored in the presence and absence of active transcription (FIGS. 5A, 14C). In the absence of polymerase, there was as expected a dramatic increase in DNA methylation of the upper strand mediated by DNMT1 (FIGS. 5A, 14A-14B). In contrast, no changes in methylation were observed in the presence of both polymerase and DNMT1 (FIGS. 5A-5B, 14B). These findings expand on previous studies that have shown the ability of RNA to modulate DNMTs enzymatic activity in vitro and strongly suggest that RNAs arising from methylation-sensitive genes and their promoters can regulate corresponding gene expression by interfering with DNA methylation.

Example 7

DNMT1 Binds to ecRNA with Greater Affinity than to DNA

We next sought to investigate the mechanism behind the observation that the C/EBPa methylation pattern is mediated by altered ecRNA levels. DNMT1 expression and enzymatic activity peaks during S phase. Intriguingly, increased ecRNA expression also occurs during the S phase. We therefore asked whether the presence of ecRNA during the S phase set the stage for ecRNA interference with DNMT1 activity. To this aim, we tested the in vivo binding of DNMT1 to ecRNA by using RNA Immunoprecipitation (RIP) with an anti-DNMT1 antibody.

Figure 15A:
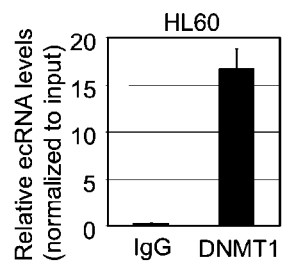
Figure 15B:
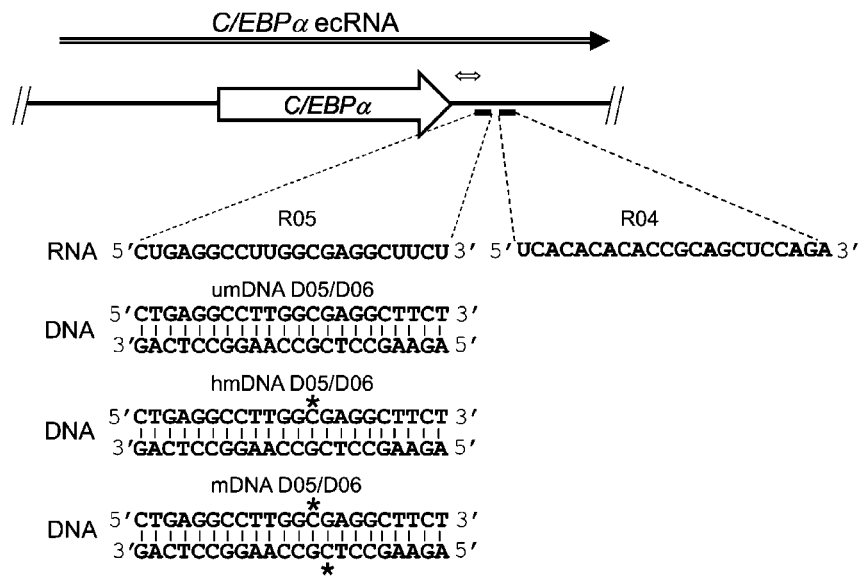
Figure 15C:
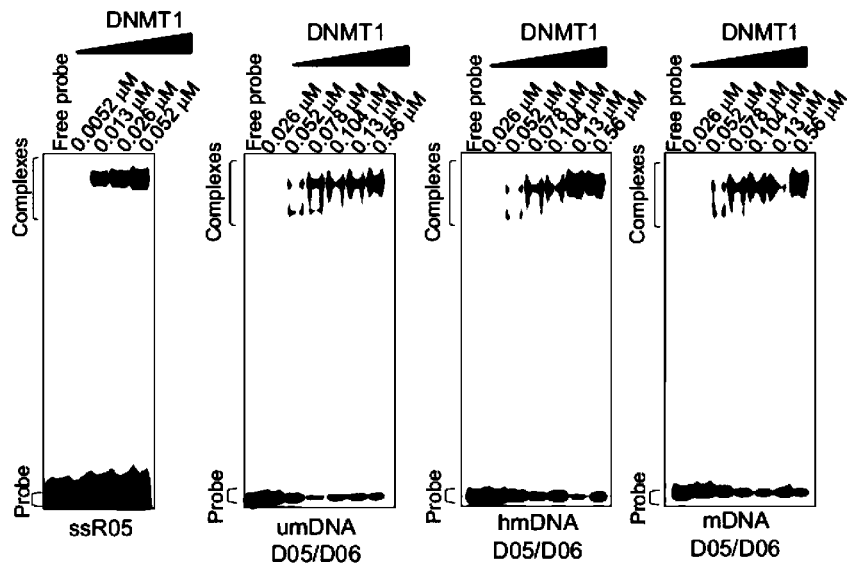
Figure 15D:
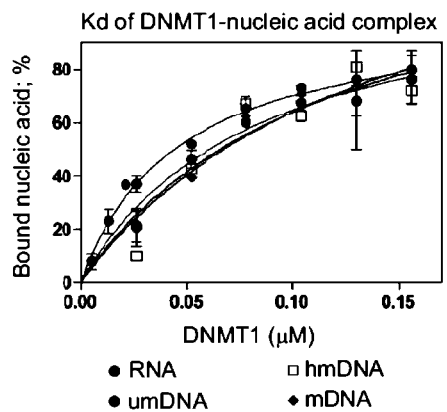
Figure 15I:
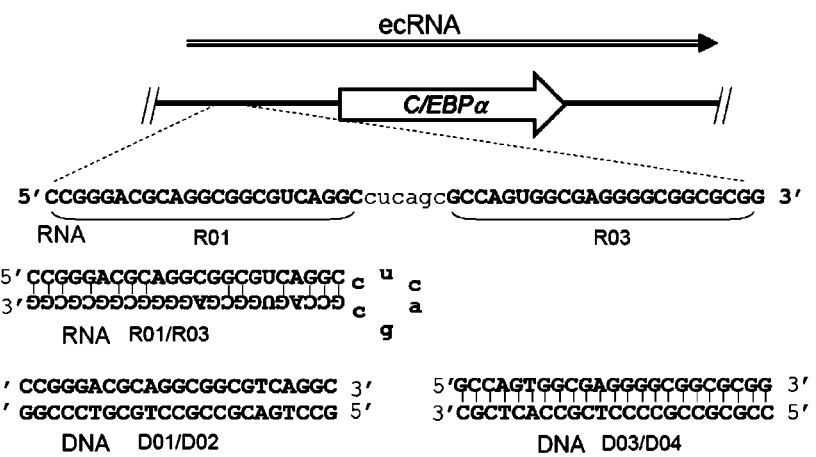

We observed ecRNA enrichment (>60-fold in HL-60 cells) in DNMT1-RNA precipitates, as compared to the IgG control, demonstrating a physical interaction between ecRNA and DNMT1 (FIG. 15A). Similar results were obtained in U937 cells (FIG. 15G). Analysis of polyA(+)/(−) fractions in DNMT1-RNA precipitates revealed enrichment of C/EBPa transcripts in the polyA(−) fraction (FIG. 15H), suggesting that the major component of C/EBPa transcripts in DNMT1-RNA precipitates was ecRNA. Next, we tested in vitro the ecRNA-DNMT1 interaction by performing RNA electrophoresis mobility shift assays (REMSA) with regions corresponding to the 5' and 3' end of the ecRNA (ssRNA: R05, corresponding to positions 4627-4648 of SEQ ID NO:8, and R04, corresponding to positions 4777-4798 of SEQ ID NO:8) (FIGS. 15B, 15I).

Figure 15J:
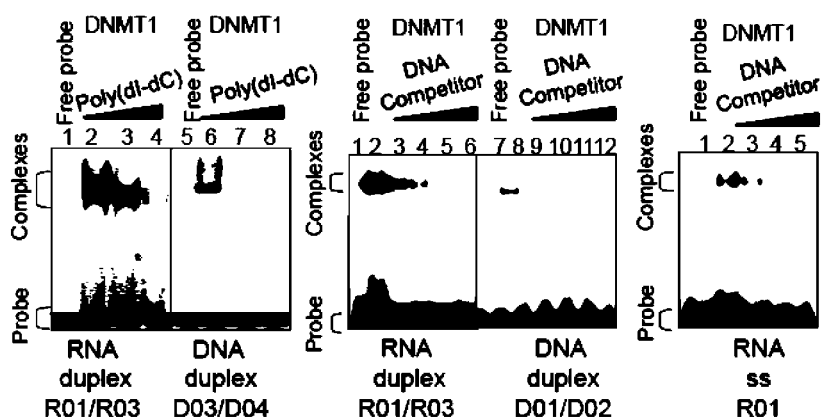

First, to compare DNMT1 binding capacity of mismatched double-stranded (ds;R01/R03) and folded single-stranded (ss;R01, R04, and R05) RNAs to dsDNAs (with the same primary sequence as the RNA oligonucleotides), we performed competitive binding assay. We observed strong binding for both ds- and ssRNA in the presence of poly (dI-dC) (non-specific competitor) and dsDNA oligos (specific competitor) (FIGS. 15J, 15C).

Second, to investigate whether DNMT1 affinity for RNA was dependent on the presence of CpG dinucleotides, we replaced the cytidine within CpG dinucleotides to uridine in the ssRNA oligonucleotide (R01: the substitution being neutral with regards to the predicted secondary structures, according to RNAfold (FIG. 15K). The mutations did not disrupt the RNA-protein complexes (FIG. 15L) unlike what has previously been shown for DNA. Further, to test if the ecRNA-DNMT1 binary complex was a case of trivial charge-charge interactions, we performed REMSA in the presence of increasing concentrations of spermine, a molecule with four positive charges at high density. Only a thousand-fold molar excess of spermine began to moderately affect the binding (FIG. 15M), suggesting a strong element of structural recognition indicate that the ecRNA can physically associate with DNMT1. This interaction is not contingent upon the presence of CpG dinucleotides, is not charge dependent, and requires certain RNA structural components.

Further to Example 3, we interrogated whether ecRNA displays higher affinity for DNMT1 than DNA. We quantitatively compared the DNMT1 binding affinity for ssRNA capable of forming secondary structures, unmethylated DNA (umDNA), hemimethylated DNA (hmDNA), and fully methylated DNA (mDNA). RNA and DNA oligonucleotides at a constant molar concentration were titrated with an increasing range of DNMT1 enzyme concentrations using EMSA. An initial complex between enzyme and RNA was formed with <0.013 μM DNMT1, whereas DNA began complexing at >0.026 μM DNMT1 (FIG. 15C). The dissociation constant (Kd) for RNA was 0.045 (±0.004) μM, whereas for DNA was between 0.082 and 0.11 μM (umDNA 0.082 (±0.03); hmDNA 0.14 (±0.11), and mDNA 0.11 (±0.06) μM)) (FIG. 15D). Remarkably, the DNMT1 complex with RNA was 2-fold stronger compared to umDNA and 3-fold stronger than hmDNA and mDNA. Importantly, RNA lacking stem-and-loop-like structures (R04; FIG. 15E) did not display the same binding affinity as folded RNA (FIG. 15F), demonstrating the effect of RNA secondary structure on RNA-DNMT1 complex formation.

In summary, these findings demonstrate that DNMT1 binds folded ecRNA with higher affinity than DNA. Based on the experiments, regions of the ecRNA in other candidate genes described herein, that can interact with DNMT1 and other DNMTs such as DNMT3a or DNMT3b, can be predicted based on whether the particular region has a propensity to form a stable RNA secondary structure. Further, knowing the effect of RNA secondary structure on RNA-DNMT1 complex formation will aid in the design of CROs to target particular regions of the ecRNA, such as by testing the secondary structure and binding stability of CRO-ecRNA complexes.

Example 8

Mapping the DNMT1 Epitranscriptome

Our observations described above suggested an inverse correlation between RNA-DNMT1 complexes and the methylation of the C/EBPa locus. Thus, we sought to explore whether this phenomenon mirrored a more global mechanism of control of genomic methylation.

Figure 16A:
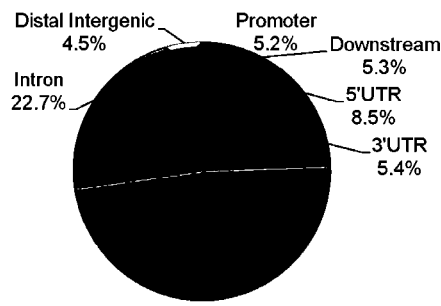
FIGS. 16A-16H show the DNMT1 epitranscriptome analysis.

We applied a comparative genome-scale approach to identify and correlate gene expression, association with DNMT1, and methylation status. cDNA libraries made of RNAs that co-immunoprecipitated with anti-DNMT1 antibody (DNMT1 library) and IgG (control library) were first assessed for C/EBPa ecRNA enrichment (FIG. 16E) and subsequently analyzed by massively parallel sequencing. Using 76-base paired-end sequencing, we produced a total of 30.25 and 26.95 million pair reads for DNMT1 and control libraries, respectively. All significant DNMT1 peaks were annotated with CEAS build on RefSeq hg19 (a total of 16,176; P<0.0001; false discovery rate of 7.5%). These peaks were aligned against the hg19 genome using locations scattered throughout the RefSeq genome annotation as follows: exonic 48%; intronic 23%; distal intergenic 5%; 5' UTR 9%; 3' UTR 5%; and upstream promoter and downstream gene (assigned as 3 kb regions flanking the annotated genes) 10% (FIG. 16A).

We focused on the genomic regions encompassing 3 kb upstream and downstream of the annotated genes ("gene loci") and identified 6,042 gene loci covered by the DNMT1 library. To assess the linkage between genomic loci giving rise to DNMT1-bound RNAs and the levels of genomic methylation and expression of the corresponding nearby genes, we applied a genome-scale methylation screening (reduced representation bisulfite sequencing, RRBS) and gene expression microarray analysis. DNMT1 library and gene expression microarray database were aligned with the RRBS library.

Figure 16B:
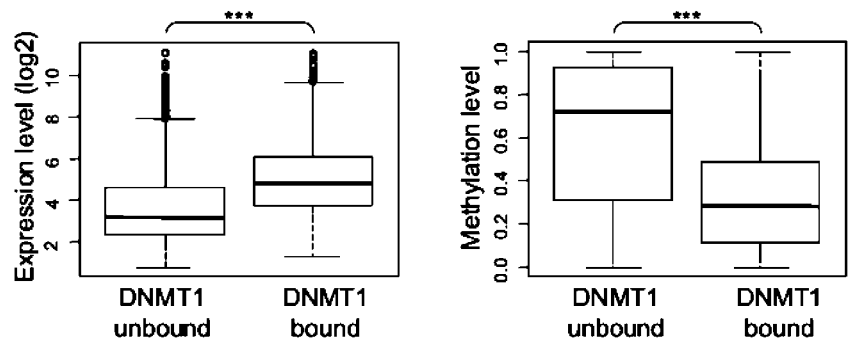
Figure 16C:
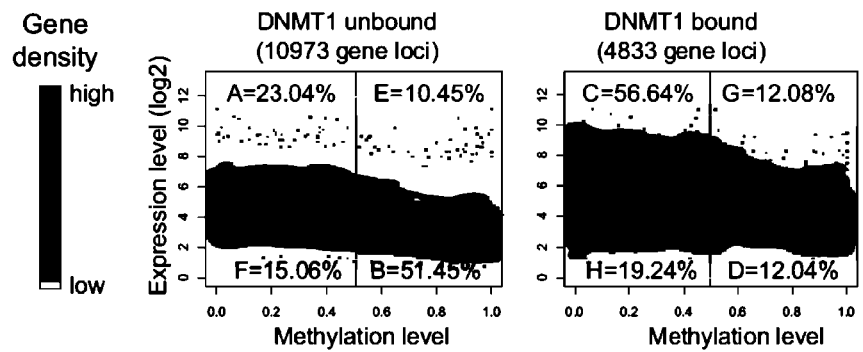
Figure 16D:
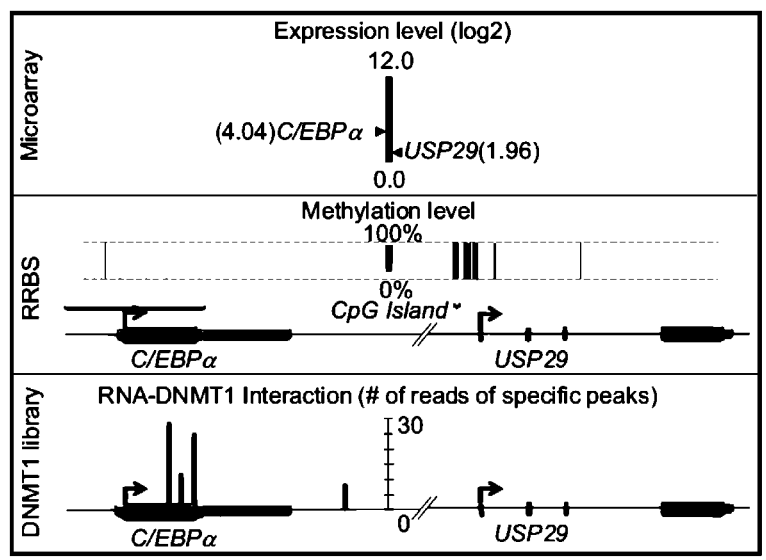
Figure 16E:
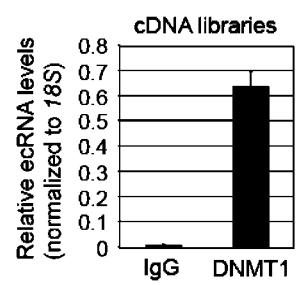
Figure 16F:
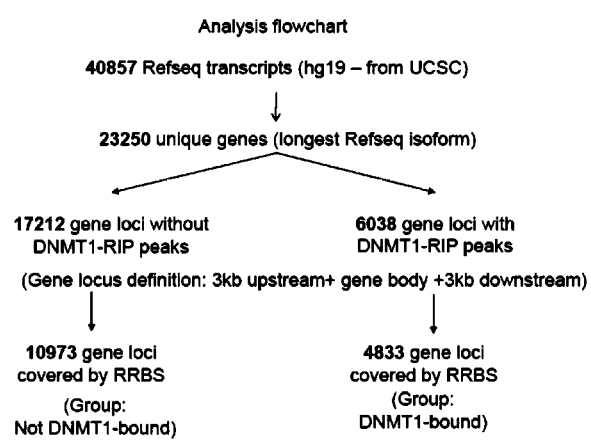

Within 15,794 RRBS-covered loci, 4,897 gene loci overlapped with the DNMT1-boudn library, and 10,897 gene loci did not (FIG. 16F). Within both groups, DNMT1-bound and not bound, genes were stratified according to expression and methylation levels (FIG. 16B). We observed that genes belonging to the DNMT1-bound group had significantly higher levels of expression than genes belonging to the DNMT1 unbound group. An opposite trend was observed for methylation levels: genes belonging to the DNMT1-bound group had significantly lower levels of methylation than genes belonging to the DNMT1 unbound group. Thus, globally, DNMT1-RNA association is negatively correlated with gene locus methylation status. Next, we clustered genes within both groups according to levels of expression and methylation (FIG. 16C). We defined genes as "expressed" and "low or not expressed" above and below the score of $\log_2 (4)=2$, respectively; and "hypomethylated" and "methylated" as genes with mean of all CpG scores below and above 50%, respectively. Interestingly, a predominant number of genes (i.e., more than 50%) were either in cluster B (i.e., DNMT1 unbound, methylation above 50%, and low expression level below $\log_2 (4)=2$) or in cluster C (i.e., DNMT1 bound, methylation below 50%, and expression levels above or slightly below $\log_2 (4)=2$). For example, 51.45% in the DNMT1 unbound group were in cluster B (lower right quadrant of FIG. 16C) and 56.64% in the DNMT1 bound group cluster C (mid-lower and upper left quadrants of FIG. 16C), in agreement with the proposed hypothesis that these interactions prevent DNMT1 dependent DNA methylation. An attractive feature of the epitranscriptome is its dual applicability: (1) as a tool for basic and clinical oncology and stem cell research; and (2) as a guide for gene specific therapeutic approaches.

Figure 16G:
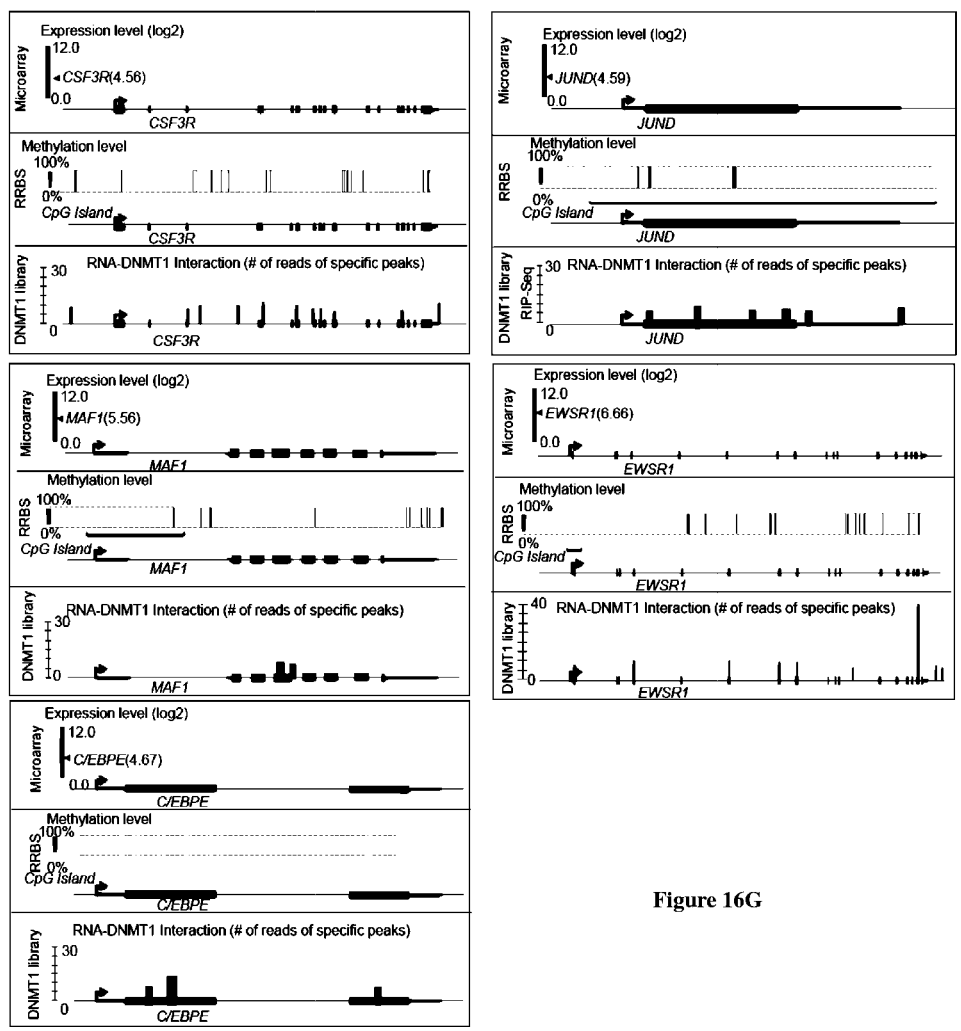
Figure 16H:
Figure 17:
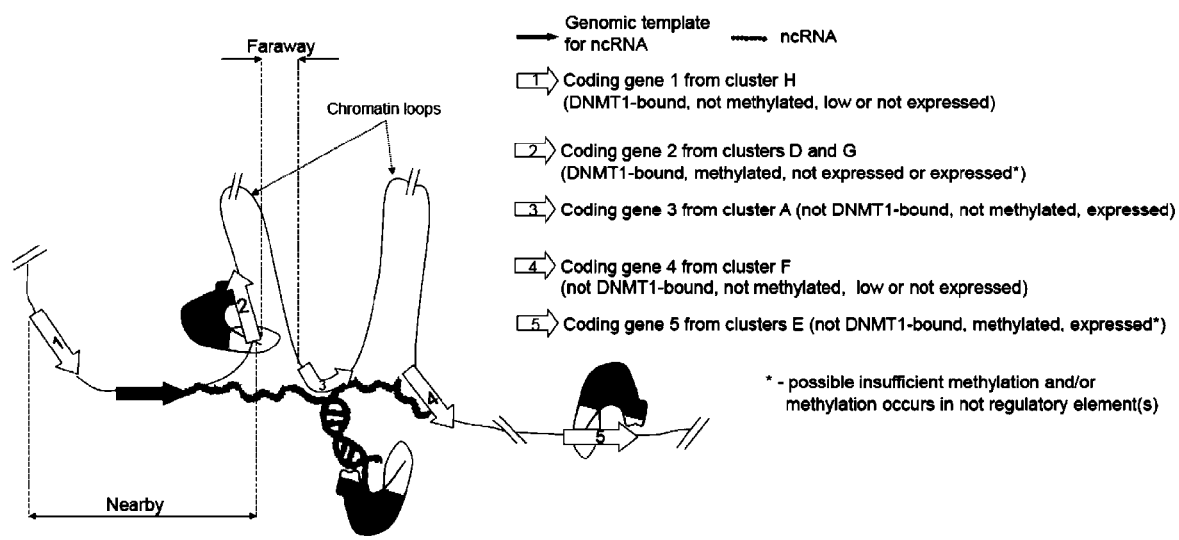
FIG. 17 is a non-limiting model of putative long-distance DNMT1 sequestration by ecRNA. Without being limited by theory, this model proposes that ecRNA is transcribed from remote genomic template (located nearby to coding genes 1 and 2) and maintain close physical proximity with coding genes 3 and 4 by chromatin looping. This ecRNA, being identified by RIPseq, will likely be aligned to the respective "Coding genes 1 and 2 loci" and not to the remote coding genes 3- and 4-corresponding loci. The coding gene 5 belongs to cluster E, where its expression may be less likely to be affected by methylation (as detected by RRBS).
Figure 18:
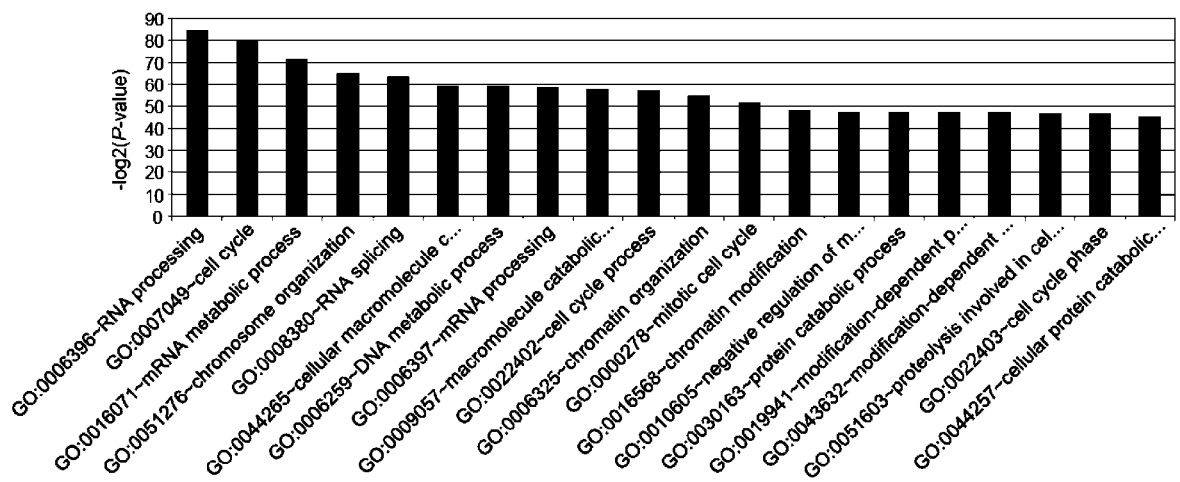
FIG. 18 is a gene ontology (GO) chart of exemplary genes within cluster C. Enrichment is shown for the first 20 GO's biological process annotations, where enrichment was determined by using Benjamini corrected P-values and $-\log_2$ (P-value) are provided.

Moreover, the numbers of genes in clusters B and C were significantly higher than numbers of genes in clusters A, F, E and G, H, D, respectively (P-value<0.0001). Examples of genes from clusters B and C are presented in FIGS. 16D, 16G, 16H. Grouping of genes in clusters A, F, E, G, H, and D may be the results of the technical limitation of RRBS, contingent upon the genomic location of the restriction sites and the DNA library size-selection, or these genes may be governed by yet another mechanism of transcriptional control. Another interesting possibility is that genes in clusters A, F, G, H, and D might be under long-distance methylation control. It has recently been shown that the ncRNA HOTTIP can exert regulatory function on distal genes via chromosomal looping, while being anchored to its own site of transcription. Without wishing to be limited by mechanism, it is possible that some of the DNMT1-bound RNAs identified by RIPseq will align to sites of transcription and the respective local genes, and not to the gene loci where the actual DNMT1-binding event takes place (FIG. 17). Interestingly, gene ontology analysis showed that genes in DNMT1-bound cluster C belong to multiple families of biological processes suggesting a general character of the DNMT1 sequestration throughout the genome (FIG. 18).

In conclusion, we have generated the first "DNMT1-centered epitranscriptome", a comprehensive map cross-referencing DNMT1-interacting transcripts to (i) DNA methylation and (ii) gene expression. These data support the notion that RNA transcripts act as a shield sequestering DNMT1 and thus modulating DNA genomic methylation. The data also provide a wider scope for applications of CROs to target a variety of DNMT1-interacting RNA transcripts listed herein.

OTHER EMBODIMENTS

All publications, patent applications, and patents mentioned in this specification are herein incorporated by reference.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, pharmacology, or related fields are intended to be within the scope of the invention.

What is claimed is:

1. A single-stranded synthesized RNA oligonucleotide consisting of a nucleotide sequence corresponding to positions 4627-4648 of SEQ ID NO:8, wherein said synthesized RNA oligonucleotide is covalently or non-covalently linked to a targeting moiety or a carrier, wherein the carrier is a condensing agent, a fusogenic agent, a protein, a lipid, a lipopolysaccharide, a carbohydrate, a dendrimer, a nanoparticle, a synthetic polymer, a vitamin, a cofactor, a cytoskeletal disrupting drug, or a cationic moiety.

2. A composition comprising the synthesized RNA oligonucleotide of claim 1 and an excipient.

3. The oligonucleotide of claim 1, wherein said oligonucleotide further comprises a label selected from the group consisting of an isotope, a radioimaging agent or a radiolabel, a fluorescent label, a nuclear magnetic resonance active label, a luminescent label, a chromophore label, a chemiluminescence label, an enzymatic label, a reporter molecule, an antibody, and an antibody fragment.

4. The oligonucleotide of claim 1, wherein at least one nucleotide of said oligonucleotide is a modified nucleotide selected from the group consisting of 5-azacytidine, 5-aza-2'-deoxycytidine, cytarabine, fludarabine, gemcitabine, clofarabine, azathioprine, 5-fluorouracil, floxuridine, mercaptopurine, thioguanine, pentostatin, and cladribine.

5. The oligonucleotide of claim 1, wherein the targeting moiety is a cell-penetrating peptide.

6. The oligonucleotide of claim 1, wherein
the carrier is said protein and the protein targets a cell or tissue or is a serum protein.

7. The oligonucleotide of claim 1, wherein the condensing agent is a liposome or a lipid micelle.

8. The oligonucleotide of claim 1, wherein said synthesized RNA oligonucleotide binds to DNA methyltransferase 1 (DNMT1).

9. The oligonucleotide of claim 1, wherein the carrier is said lipid and the lipid is a cholesterol.

10. The oligonucleotide of claim 1, wherein the carrier is said carbohydrate and the carbohydrate is a polysaccharide or a multivalent sugar.

\* \* \* \* \*